(12) United States Patent
Wu et al.

(10) Patent No.: US 11,046,679 B2
(45) Date of Patent: Jun. 29, 2021

(54) INDOLEAMINE 2,3-DIOXYGENASE INHIBITOR AND APPLICATION

(71) Applicant: Nanjing TransThera Biosciences Co. Ltd., Jiangsu (CN)

(72) Inventors: Frank Wu, Nanjing (CN); Lin Li, Nanjing (CN)

(73) Assignee: Nanjing TransThera Biosciences Co. Ltd., Nanjing (CN)

( * ) Notice: Subject to any disclaimer, the term of this patent is extended or adjusted under 35 U.S.C. 154(b) by 0 days.

(21) Appl. No.: 16/607,827

(22) PCT Filed: Apr. 24, 2018

(86) PCT No.: PCT/CN2018/084267
§ 371 (c)(1),
(2) Date: Oct. 24, 2019

(87) PCT Pub. No.: WO2018/196747
PCT Pub. Date: Nov. 1, 2018

(65) Prior Publication Data
US 2020/0181131 A1    Jun. 11, 2020

(30) Foreign Application Priority Data

Apr. 24, 2017  (CN) .......................... 201710270704.4
Jul. 5, 2017   (CN) .......................... 201710543401.5
Dec. 29, 2017  (CN) .......................... 201711478213.5

(51) Int. Cl.
C07D 413/12    (2006.01)
C07D 493/08    (2006.01)

(52) U.S. Cl.
CPC ......... *C07D 413/12* (2013.01); *C07D 493/08* (2013.01)

(58) Field of Classification Search
CPC .......................... C07D 413/12; C07D 493/08
See application file for complete search history.

(56) References Cited

U.S. PATENT DOCUMENTS

2020/0231606 A1*  7/2020  Liu ..................... C07F 7/0836

FOREIGN PATENT DOCUMENTS

| CN | 101212967 A    |   | 7/2008  |
|----|----------------|---|---------|
| CN | 105481789 A    |   | 4/2016  |
| CN | 105646389 A    |   | 6/2016  |
| CN | 106883194 A    | * | 6/2017  |
| CN | 106883194 A    |   | 6/2017  |
| CN | 107304191 A    |   | 10/2017 |
| WO | 2008/058178 A1 |   | 5/2008  |
| WO | 2018/184585 A1 |   | 10/2018 |

OTHER PUBLICATIONS

Foster et al. Trends In Pharmacological Sciences 1984, 5, p. 524-527 (Year: 1984).*
International Search Report and Written Opinion for Application No. PCT/CN2018/084267, dated Jul. 23, 2018, 15 pages.
European Office Action for Application No. 18792247.1, dated Jan. 3, 2020, 7 pages.

* cited by examiner

*Primary Examiner* — Matthew P Coughlin
(74) *Attorney, Agent, or Firm* — McCarter & English, LLP; Steven G. Davis; Wei Song

(57) ABSTRACT

The present invention belongs to the field of medical technology. Particularly, the present invention relates to a compound shown in formula (I), a pharmaceutically acceptable salt thereof, and a stereoisomer of the same. X, Y, Z, $R^1$, $R^2$, $R^3$, $R^{1a}$, $R^{2a}$, m, and n are as defined in the specification. The present invention also relates to pharmaceutical preparations and pharmaceutical compositions of these compounds and a use thereof in preparing a drug for treating a related disease mediated by abnormal indoleamine 2,3-dioxygenase (IDO).

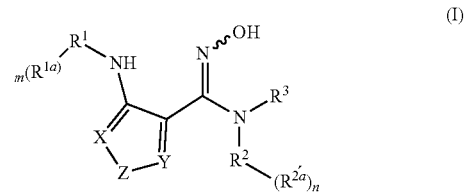

20 Claims, 1 Drawing Sheet

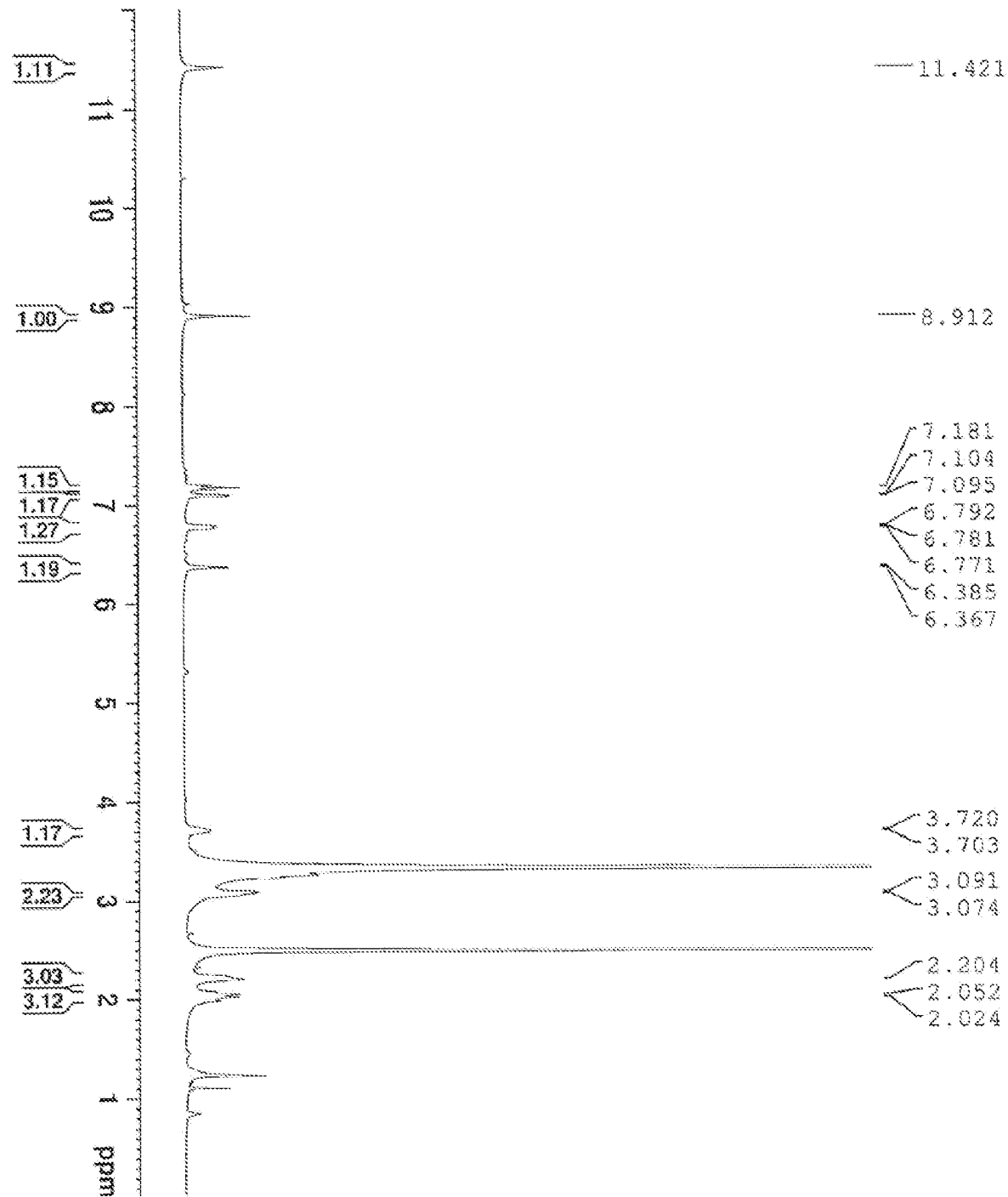

INDOLEAMINE 2,3-DIOXYGENASE INHIBITOR AND APPLICATION

CROSS-REFERENCE TO RELATED APPLICATIONS

This application is a U.S. national stage filing, under 35 U.S.C. § 371(c), of International Application No. PCT/CN2018/084267, filed Apr. 24, 2018, which claims priority to Chinese Patent Application No. 201710270704.4, filed Apr. 24, 2017; Chinese Patent Application No. 201710543401.5, filed Jul. 5, 2017; and Chinese Patent Application No. 201711478213.5, filed Dec. 29, 2017.

FIELD OF THE INVENTION

The invention belongs to the field of medical technology, relates to a compound of indoleamine 2,3-dioxygenase (IDO) inhibitor, a pharmaceutically acceptable salt and a stereoisomer thereof, a pharmaceutical formulation and a composition of the same, and use thereof in the manufacture of a medicament for treating a disease mediated by indoleamine 2,3-dioxygenase (IDO) abnormality.

BACKGROUND OF THE INVENTION

Tryptophan (Trp) is an essential amino-acid in vivo, and is used to biosynthesize protein, niacin and neurotransmitter of 5-hydroxytryptamine (serotonin) in vivo. Indoleamine 2,3-dioxygenase (IDO) is a intracellular monomeric enzyme containing ferroheme, and is widely distributed in many tissues and cells of human and animals. IDO can catalyze the first step of oxidative splitting of indole ring in L-tryptophan to produce kynurenine, which is a crucial step for the rate of splitting reaction. IDO is expressed at a low level in a normal state, and an abnormally high expression of IDO can be detected in a disease state of a living body. IDO plays a crucial role in the pathogenesis of a nervous system disease (particularly in Alzheimer's disease and depression). IDO has a further function of immune tolerance. IDO on a tumour cell or an antigen presenting cell can induce immune tolerance of T-cell to the tumour antigen. In addition, IDO is also involved in the pathogenesis of chronic infection, HIV-infection, AIDS, an autoimmune disease and the like. As a result, IDO has been verified as an important target for drug discovery, and the development of IDO inhibitor is needed urgently.

IDO affects brain functions, thereby leading to occurrence of a nervous system disease, mainly by following two mechanisms, (1) during inflammatory response, tryptophan metabolism leads to a reduced concentration of cycled tryptophan, thus to a reduced 5-hydroxytryptamine, and finally to occurrence of depression; (2) catalyzing tryptophan metabolism through kynurenine pathway leads to accumulation of kynurenine and neurotoxic quinolinic acid, thereby resulting in occurrence of a nervous system disease. Therefore, IDO inhibitor has a broad prospect in treating a nervous system disease such as Alzheimer's disease and depression.

IDO has become a very important small molecular regulatory target in antitumor immunotherapy. IDO regulates the immune system mainly in: (1) local tryptophan depletion may occur in cells due to the high expression of IDO, and T-cell proliferation will stay at G1 stage under a reduced concentration of tryptophan, since T-cell is very sensitive to tryptophan depletion; (2) tryptophan degradation depending on IDO results in an increased kynurenine, which induces T-cell apoptosis mediated by an oxygen radical; (3) up-regulation of IDO expression in a dendritic cell enhances local regulatory T-cell (Treg)-mediated immunosuppression by degrading local tryptophan and promotes the body's peripheral immune tolerance to tumor-specific antigens.

At present, a series of IDO small molecule inhibitors have been developed at home and abroad to treat or prevent IDO-related diseases. For example, WO99/29310 reported the use of IDO inhibitors 1-methyl-DL-tryptophan, 4-(3-benzofuran)-DL-alanine, 4-(3-benzothiophen)-DL-alanine and 6-nitro-L-tryptophan, to alter T-cell mediated immunity, including altering the concentration of local extracellular tryptophan and tryptophan metabolites.

Some specific compounds with IDO inhibit effect are also reported in WO2004/094409. In US2004/0234623, it reported a kind of IDO inhibitor, which is used to treat cancer and infection.

However, the existing indoleamine 2,3-dioxygenase (IDO) inhibitors generally have a low inhibiting potency, and no indoleamine 2,3-dioxygenase (IDO) inhibitor drugs have been available. Among the drugs in development, the representative IDO inhibitors are Epacadostat (II, Under Active Development) and NLG-919 (I, Under Active Development). Their structural formulae are as follows:

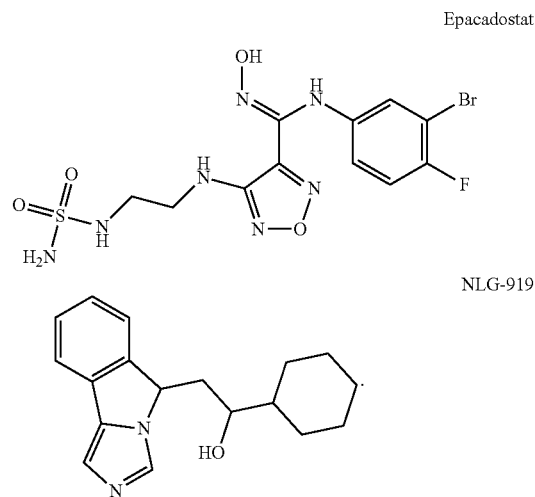

The invention aims to study a series of novel and highly effective IDO inhibitors, which have good drug-forming properties and can be used to prepare drugs for preventing and/or treating Alzheimer's disease, cataract, cellular immune activation-related infections, autoimmune diseases, AIDS, cancers, depression or abnormal tryptophan metabolism.

SUMMARY OF THE INVENTION

The technical problem to be solved by the present invention is to provide a novel IDO inhibitor which has excellent inhibitory activity against IDO and can be used for treating diseases mediated by IDO abnormalities.

The present invention provides the following technical solution:

1. A compound of formula I, a pharmaceutically acceptable salt and a stereoisomer thereof:

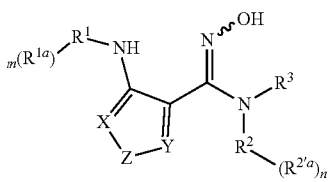

I wherein, ⁓ represents a cis-isomer, a trans-isomer or a mixture of cis- and trans-isomers;

X and Y are independently of each other CH or N;

Z is O or S;

$R^1$ is selected from the group consisting of cycloalkyl, heterocyclyl and heteroaryl, which is optionally substituted with $R^{1a}$, wherein $R^{1a}$ is selected from the group consisting of hydrogen, halogen, $C_{1-6}$ alkyl, $C_{2-6}$ alkenyl, $C_{2-6}$ alkynyl, halogenated $C_{1-6}$ alkyl, —CN, —$NO_2$, —$OR^b$, —C(O)$R^c$, —C(O)$OR^b$, —OC(O)$R^c$, —C(O)$NR^eR^f$, —OC(O)$NR^eR^f$, —$NR^eR^f$, —$NR^dC(O)R^c$, —$NR^dC(O)NR^eR^f$, —$NR^dC(O)OR^b$, —$SR^b$, —S(O)$R^c$, —S(O)$NR^eR^f$, —S(O)$_2R^c$, —S(O)$_2NR^eR^f$, cycloalkyl, heterocyclyl, heteroaryl and aryl;

$R^2$ is selected from the group consisting of cycloalkyl, heterocyclyl, heteroaryl and aryl, which is optionally substituted with $R^{2a}$, wherein $R^{2a}$ is selected from the group consisting of hydrogen, halogen, $C_{1-6}$ alkyl, $C_{2-6}$ alkenyl, $C_{2-6}$ alkynyl, halogenated $C_{1-6}$ alkyl, —CN, —$NO_2$, —$OR^b$, —C(O)$R^c$, —C(O)$OR^b$, —OC(O)$R^c$, —C(O)$NR^eR^f$, —OC(O)$NR^eR^f$, —$NR^eR^f$, —$NR^dC(O)R^c$, —$NR^dC(O)NR^eR^f$, —$NR^dC(O)OR^b$, —$SR^b$, —S(O)$R^c$, —S(O)$NR^eR^f$, —S(O)$_2R^c$, —S(O)$_2NR^eR^f$, cycloalkyl, heterocyclyl, heteroaryl and aryl;

$R^3$ is selected from the group consisting of hydrogen, $C_{1-6}$ alkyl and cycloalkyl;

$R^b$ is selected from the group consisting of hydrogen, $C_{1-6}$ alkyl, halogenated $C_{1-6}$ alkyl, $C_{1-6}$ alkoxy $C_{1-6}$ alkyl, cycloalkyl, heterocyclyl, heteroaryl and aryl;

$R^c$ is selected from the group consisting of hydrogen, $C_{1-6}$ alkyl, halogenated $C_{1-6}$ alkyl, $C_{1-6}$ alkoxy, cycloalkyl, heterocyclyl, heteroaryl and aryl;

$R^d$, $R^e$, and $R^f$ are independently of each other selected from the group consisting of hydrogen, $C_{1-6}$ alkyl, halogenated $C_{1-6}$ alkyl, cycloalkyl, heterocyclyl, heteroaryl and aryl;

m is 0, 1, 2, 3, 4 or 5; and n is 0, 1, 2, 3, 4 or 5.

2. The compound, the pharmaceutically acceptable salt and the stereoisomer thereof according to embodiment 1:

wherein, ⁓ represents a cis-isomer, a trans-isomer or a mixture of cis- and trans-isomers;

X and Y are independently of each other CH or N;

Z is O or S;

$R^1$ is selected from the group consisting of 3-14 membered cycloalkyl, 3-14 membered heterocyclyl and 5-14 membered heteroaryl, which is optionally substituted with $R^{1a}$, wherein $R^{1a}$ is selected from the group consisting of hydrogen, halogen, $C_{1-6}$ alkyl, $C_{2-6}$ alkenyl, $C_{2-6}$ alkynyl, halogenated $C_{1-6}$ alkyl, —CN, —$NO_2$, —$OR^b$, —C(O)$R^c$, —C(O)$OR^b$, —OC(O)$R^c$, —C(O)$NR^eR^f$, —OC(O)$NR^eR^f$, —$NR^eR^f$, —$NR^dC(O)R^c$, —$NR^dC(O)NR^eR^f$, —$NR^dC(O)OR^b$, —$SR^b$, —S(O)$R^c$, —S(O)$NR^eR^f$, —S(O)$_2R^c$, —S(O)$_2NR^eR^f$, 3-8 membered cycloalkyl, 3-8 membered heterocyclyl, 5-8 membered heteroaryl and 6-14 membered aryl;

$R^2$ is selected from the group consisting of 3-8 membered cycloalkyl, 3-14 membered heterocyclyl, 5-14 membered heteroaryl and 6-14 membered aryl, which is optionally substituted with $R^{2a}$, wherein $R^{2a}$ is selected from the group consisting of hydrogen, halogen, $C_{1-6}$ alkyl, $C_{2-6}$ alkenyl, $C_{2-6}$ alkynyl, halogenated $C_{1-6}$ alkyl, —CN, —$NO_2$, —$OR^b$, —C(O)$R^c$, —C(O)$OR^b$, —OC(O)$R^c$, —C(O)$NR^eR^f$, —OC(O)$NR^eR^f$, —$NR^eR^f$, —$NR^dC(O)R^c$, —$NR^dC(O)NR^eR^f$, —$NR^dC(O)OR^b$, —$SR^b$, —S(O)$R^c$, —S(O)$NR^eR^f$, —S(O)$_2R^c$, —S(O)$_2NR^eR^f$, 3-8 membered cycloalkyl, 3-8 membered heterocyclyl, 5-8 membered heteroaryl and 6-14 membered aryl;

$R^3$ is selected from the group consisting of hydrogen, $C_{1-6}$ alkyl and 3-8 membered cycloalkyl;

$R^b$ is selected from the group consisting of hydrogen, $C_{1-6}$ alkyl, halogenated $C_{1-6}$ alkyl, $C_{1-6}$ alkoxy $C_{1-6}$ alkyl, 3-8 membered cycloalkyl, 3-8 membered heterocyclyl, 5-8 membered heteroaryl and 6-14 membered aryl;

$R^c$ is selected from the group consisting of hydrogen, $C_{1-6}$ alkyl, halogenated $C_{1-6}$ alkyl, $C_{1-6}$ alkoxy, 3-8 membered cycloalkyl, 3-8 membered heterocyclyl, 5-8 membered heteroaryl and 6-14 membered aryl;

$R^d$, $R^e$ and $R^f$ are independently of each other selected from the group consisting of hydrogen, $C_{1-6}$ alkyl, halogenated $C_{1-6}$ alkyl, 3-8 membered cycloalkyl, 3-8 membered heterocyclyl, 5-8 membered heteroaryl and 6-14 membered aryl;

m is 0, 1, 2, 3, 4 or 5; and n is 0, 1, 2, 3, 4 or 5.

3. The compound, the pharmaceutically acceptable salt and the stereoisomer thereof according to embodiment 2, having the following structure of formula II:

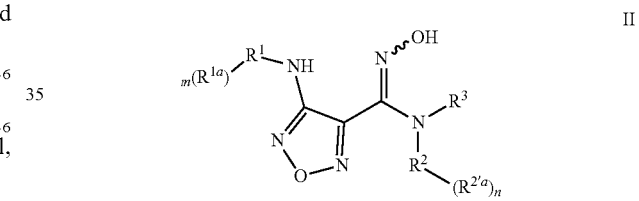

II wherein, ⁓ represents a cis-isomer, a trans-isomer or a mixture of cis- and trans-isomers;

$R^1$ is selected from the group consisting of 3-12 membered heterocyclyl and 5-12 membered heteroaryl, which is optionally substituted with $R^{1a}$, wherein $R^{1a}$ is selected from the group consisting of hydrogen, halogen, $C_{1-6}$ alkyl, $C_{2-6}$ alkenyl, $C_{2-6}$ alkynyl, halogenated $C_{1-6}$ alkyl, —CN, —$NO_2$, —$OR^b$, —C(O)$R^c$, —C(O)$OR^b$, —OC(O)$R^c$, —C(O)$NR^eR^f$, —OC(O)$NR^eR^f$, —$NR^eR^f$, —$NR^dC(O)R^c$, —$NR^dC(O)NR^eR^f$, —$NR^dC(O)OR^b$, —$SR^b$, —S(O)$R^c$, —S(O)$NR^eR^f$, —S(O)$_2R^c$, —S(O)$_2NR^eR^f$, 3-8 membered cycloalkyl, 3-8 membered heterocyclyl, 5-8 membered heteroaryl and 6-14 membered aryl;

$R^2$ is selected from the group consisting of 6-14 membered aryl and 5-12 membered heteroaryl, which is optionally substituted with $R^{2a}$, wherein $R^{2a}$ is selected from the group consisting of hydrogen, halogen, $C_{1-6}$ alkyl, $C_{2-6}$ alkenyl, $C_{2-6}$ alkynyl, halogenated $C_{1-6}$ alkyl, —CN, —$NO_2$, —$OR^b$, —C(O)$R^c$, —C(O)$OR^b$, —OC(O)$R^c$, —C(O)$NR^eR^f$, —OC(O)$NR^eR^f$, —$NR^eR^f$, —$NR^dC(O)R^c$, —$NR^dC(O)NR^eR^f$, —$NR^dC(O)OR^b$, —$SR^b$, —S(O)$R^c$, —S(O)$NR^eR^f$, —S(O)$_2R^c$, —S(O)$_2NR^eR^f$, 3-8 membered cycloalkyl, 3-8 membered heterocyclyl, 5-8 membered heteroaryl and 6-14 membered aryl;

$R^3$ is hydrogen or $C_{1-6}$ alkyl;

$R^b$ is selected from the group consisting of hydrogen, $C_{1-6}$ alkyl, halogenated $C_{1-6}$ alkyl and $C_{1-6}$ alkoxy $C_{1-6}$ alkyl;

$R^c$ is selected from the group consisting of hydrogen, $C_{1-6}$ alkyl, halogenated $C_{1-6}$ alkyl and $C_{1-6}$ alkoxy;

$R^d$, $R^e$ and $R^f$ are independently of each other selected from the group consisting of hydrogen, $C_{1-6}$ alkyl and halogenated $C_{1-6}$ alkyl;

m is 0, 1, 2 or 3; and n is 0, 1, 2 or 3.

$R^1$ is further preferably selected from the group consisting of 3-8 membered heterocyclyl, 5-6 membered heteroaryl, 6-12 membered ortho-heterocyclyl, 6-12 membered bridged heterocyclyl and 6-12 membered spiro-heterocyclyl, which is optionally substituted with $R^{1a}$, wherein $R^{1a}$ is as defined above.

$R^1$ is further preferably selected from the group consisting of 4-6 membered saturated heterocyclyl, 8 membered saturated ortho-heterocyclyl and 7-8 membered saturated bridged heterocyclyl and 7 membered saturated spiro-heterocyclyl, which is optionally substituted with $R^{1a}$, wherein $R^{1a}$ is selected from the group consisting of hydrogen, halogen, $C_{1-6}$ alkyl, $C_{2-6}$ alkenyl, $C_{2-6}$ alkynyl, halogenated $C_{1-6}$ alkyl, —CN, —NO$_2$, —OR$^b$, —C(O)R$^c$, —C(O)OR$^b$, —OC(O)R$^c$, —C(O)NR$^e$R$^f$, —OC(O)NR$^e$R$^f$, —NR$^e$R$^f$, —NR$^d$C(O)R$^c$, —NR$^d$C(O)NR$^e$R$^f$, —NR$^d$C(O)OR$^b$, —SR$^b$, —S(O)R$^c$, —S(O)NR$^e$R$^f$, —S(O)$_2$R$^c$ and —S(O)$_2$NR$^e$R$^f$;

$R^b$ is selected from the group consisting of hydrogen, $C_{1-6}$ alkyl, halogenated $C_{1-6}$ alkyl and $C_{1-6}$ alkoxy $C_{1-6}$ alkyl;

$R^c$ is selected from the group consisting of hydrogen, $C_{1-6}$ alkyl, halogenated $C_{1-6}$ alkyl and $C_{1-6}$ alkoxy; and $R^d$, $R^e$ and $R^f$ are independently of each other selected from the group consisting of hydrogen, $C_{1-6}$ alkyl and halogenated $C_{1-6}$ alkyl.

Preferably, $R^1$ is

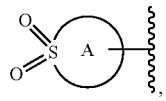

ring A is 3-12 membered mono-, ortho-, spiro-, or bridged heterocyclyl; and $R^2$ is 6-14 membered aryl.

Preferably, $R^1$ is

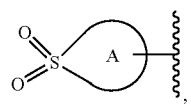

ring A is selected from the group consisting of 3-8 membered mono-heterocyclyl, 6-12 membered ortho-heterocyclyl, 6-12 membered bridged heterocyclyl and 6-12 membered spiro-heterocyclyl; and $R^2$ is phenyl.

Preferably, $R^1$ is

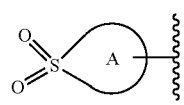

ring A is selected from the group consisting of 4-6 membered saturated heterocyclyl, 8 membered saturated ortho-heterocyclyl, 7-8 membered saturated bridged heterocyclyl and 7 membered saturated spiro-heterocyclyl; and $R^2$ is phenyl.

4. The compound, the pharmaceutically acceptable salt and the stereoisomer thereof according to embodiment 3:

wherein, $R^1$ is

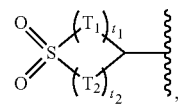

$T_1$ and $T_2$ are independently of each other selected from the group consisting of $CR^4R^{4\prime}$, $NR^4$ or O, $t_1$ and $t_2$ are independently of each other 0, 1, 2 or 3, and $t_1$ and $t_2$ are not equal to 0 at the same time; $R^1$ is optionally substituted with $R^{1a}$, wherein $R^{1a}$ is selected from the group consisting of hydrogen, halogen, $C_{1-6}$ alkyl, $C_{2-6}$ alkenyl, $C_{2-6}$ alkynyl, halogenated $C_{1-6}$ alkyl, —CN, —NO$_2$, —OR$^b$, —C(O)R$^c$, —C(O)OR$^b$, —OC(O)R$^c$, —C(O)NR$^e$R$^f$, —OC(O)NR$^e$R$^f$, —NR$^e$R$^f$, —NR$^d$C(O)R$^c$, —NR$^d$C(O)NR$^e$R$^f$, —NR$^d$C(O)OR$^b$, —SR$^b$, —S(O)R$^c$, —S(O)NR$^e$R$^f$, —S(O)$_2$R$^c$, —S(O)$_2$NR$^e$R$^f$, 5-7 membered cycloalkyl, 5-7 membered heterocyclyl, 5-7 membered heteroaryl and phenyl; and $R^4$ and $R^{4\prime}$ are independently of each other hydrogen or $C_{1-6}$ alkyl;

$R^2$ is phenyl, optionally substituted with $R^{2a}$, wherein $R^{2a}$ is selected from the group consisting of hydrogen, halogen and $C_{1-6}$ alkyl;

$R^b$ is selected from the group consisting of hydrogen, $C_{1-6}$ alkyl, halogenated $C_{1-6}$ alkyl and $C_{1-6}$ alkoxy $C_{1-6}$ alkyl;

$R^c$ is selected from the group consisting of hydrogen, $C_{1-6}$ alkyl, halogenated $C_{1-6}$ alkyl and $C_{1-6}$ alkoxy; and $R^d$, $R^e$ and $R^f$ are independently of each other selected from the group consisting of hydrogen, $C_{1-6}$ alkyl and halogenated $C_{1-6}$ alkyl.

5. The compound, the pharmaceutically acceptable salt and the stereoisomer thereof according to embodiment 4:

wherein, $R^1$ is

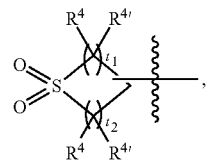

$t_1$ and $t_2$ are independently of each other 0, 1, 2 or 3, and $t_1$ and $t_2$ are not equal to 0 at the same time; $R^1$ is optionally substituted with $R^{1a}$, wherein $R^{1a}$ is selected from the group consisting of hydrogen, halogen, $C_{1-6}$ alkyl, $C_{2-6}$ alkenyl, $C_{2-6}$ alkynyl, halogenated $C_{1-6}$ alkyl, —CN, —NO$_2$, —OR$^b$, —C(O)R$^c$, —C(O)OR$^b$, —OC(O)R$^c$, —C(O)NR$^e$R$^f$, —OC(O)NR$^e$R$^f$, —NR$^e$R$^f$, —NR$^d$C(O)R$^c$, —NR$^d$C(O)NR$^e$R$^f$, —NR$^d$C(O)OR$^b$, —SR$^b$, —S(O)R$^c$, —S(O)NR$^e$R$^f$, —S(O)$_2$R$^c$ and —S(O)$_2$NR$^e$R$^f$, and $R^4$ and $R^{4\prime}$ are independently of each other hydrogen or $C_{1-6}$ alkyl;

$R^b$ is selected from the group consisting of hydrogen, $C_{1-6}$ alkyl, halogenated $C_{1-6}$ alkyl and $C_{1-6}$ alkoxy $C_{1-6}$ alkyl;

$R^c$ is selected from the group consisting of hydrogen, $C_{1-6}$ alkyl, halogenated $C_{1-6}$ alkyl and $C_{1-6}$ alkoxy; and $R^d$, $R^e$ and $R^f$ are independently of each other selected from the group consisting of hydrogen, $C_{1-6}$ alkyl and halogenated $C_{1-6}$ alkyl.

Preferably, $R^1$ is

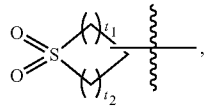

$t_1$ and $t_2$ are independently of each other 0, 1, 2 or 3, and $t_1$ and $t_2$ are not equal to 0 at the same time; $R^1$ is optionally substituted with $R^{1a}$, wherein $R^{1a}$ is selected from the group consisting of hydrogen, halogen and $C_{1-6}$ alkyl;

$R^2$ is phenyl, which is optionally substituted with $R^{2a}$, wherein $R^{2a}$ is selected from the group consisting of hydrogen, halogen and $C_{1-6}$ alkyl;

$R^3$ is hydrogen or $C_{1-6}$ alkyl;

m is 0, 1 or 2; and n is 0, 1, 2, 3, 4 or 5.

6. The compound, the pharmaceutically acceptable salt and the stereoisomer thereof according to embodiment 3: wherein, $R^1$ is

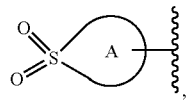

ring A is selected from the group consisting of 6-12 membered ortho-heterocyclyl, 6-12 membered bridged heterocyclyl and 6-12 membered spiro-heterocyclyl; which is optionally substituted with $R^{1a}$, wherein $R^{1a}$ is selected from the group consisting of hydrogen, halogen, $C_{1-6}$ alkyl, $C_{2-6}$ alkenyl, $C_{2-6}$ alkynyl, halogenated $C_{1-6}$ alkyl, —CN, —NO$_2$, —OR$^b$, —C(O)R$^c$, —C(O)OR$^b$, —OC(O)R$^c$, —C(O)NR$^e$R$^f$, —OC(O)NR$^e$R$^f$, —NR$^e$R$^f$, —NR$^d$C(O)R$^c$, —NR$^d$C(O)NR$^e$R$^f$, —NR$^d$C(O)OR$^b$, —SR$^b$, —S(O)R$^c$, —S(O)NR$^e$R$^f$, —S(O)$_2$R$^c$, —S(O)$_2$NR$^e$R$^f$, 5-7 membered cycloalkyl, 5-7 membered heterocyclyl, 5-7 membered heteroaryl and phenyl;

$R^2$ is phenyl, which is optionally substituted with $R^{2a}$, wherein $R^{2a}$ is selected from the group consisting of hydrogen, halogen and $C_{1-6}$ alkyl;

$R^b$ is selected from the group consisting of hydrogen, $C_{1-6}$ alkyl, halogenated $C_{1-6}$ alkyl and $C_{1-6}$ alkoxy $C_{1-6}$ alkyl;

$R^c$ is selected from the group consisting of hydrogen, $C_{1-6}$ alkyl, halogenated $C_{1-6}$ alkyl and $C_{1-6}$ alkoxy; and $R^d$, $R^e$ and $R^f$ are independently of each other selected from the group consisting of hydrogen, $C_{1-6}$ alkyl and halogenated $C_{1-6}$ alkyl.

7. The compound, the pharmaceutically acceptable salt and the stereoisomer thereof according to embodiment 6: wherein, $R^1$ is

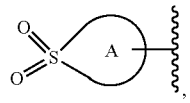

ring A is selected from the group consisting of 6-12 membered saturated ortho-heterocyclyl, 6-12 membered saturated bridged heterocyclyl and 6-12 membered saturated spiro-heterocyclyl, which is optionally substituted with $R^{1a}$, wherein $R^{1a}$ is selected from the group consisting of hydrogen, halogen, $C_{1-6}$ alkyl, $C_{2-6}$ alkenyl, $C_{2-6}$ alkynyl, halogenated $C_{1-6}$ alkyl, —CN, —NO$_2$, —OR$^b$, —C(O)R$^c$, —C(O)OR$^b$, —OC(O)R$^c$, —C(O)NR$^e$R$^f$, —OC(O)NR$^e$R$^f$, —NR$^e$R$^f$, —NR$^d$C(O)R$^c$, —NR$^d$C(O)NR$^e$R$^f$, —NR$^d$C(O)OR$^b$, —SR$^b$, —S(O)R$^c$, —S(O)NR$^e$R$^f$, —S(O)$_2$R$^c$ and —S(O)$_2$NR$^e$R$^f$;

$R^b$ is selected from the group consisting of hydrogen, $C_{1-6}$ alkyl, halogenated $C_{1-6}$ alkyl and $C_{1-6}$ alkoxy $C_{1-6}$ alkyl;

$R^c$ is selected from the group consisting of hydrogen, $C_{1-6}$ alkyl, halogenated $C_{1-6}$ alkyl and $C_{1-6}$ alkoxy; and $R^d$, $R^e$ and $R^f$ are independently of each other selected from the group consisting of hydrogen, $C_{1-6}$ alkyl and halogenated $C_{1-6}$ alkyl.

8. The compound, the pharmaceutically acceptable salt and the stereoisomer thereof according to embodiment 3: wherein, $R^1$ is 5-6 membered heteroaryl, which is optionally substituted with $R^{1a}$, wherein $R^{1a}$ is selected from the group consisting of hydrogen, halogen, $C_{1-6}$ alkyl, $C_{2-6}$ alkenyl, $C_{2-6}$ alkynyl, halogenated $C_{1-6}$ alkyl, —CN, —NO$_2$, —OR$^b$, —C(O)R$^c$, —C(O)OR$^b$, —OC(O)R$^c$, —C(O)NR$^e$R$^f$, —OC(O)NR$^e$R$^f$, —NR$^e$R$^f$, —NR$^d$C(O)R$^c$, —NR$^d$C(O)NR$^e$R$^f$, —NR$^d$C(O)OR$^b$, —SR$^b$, —S(O)R$^c$, —S(O)NR$^e$R$^f$, —S(O)$_2$R$^c$, —S(O)$_2$NR$^e$R$^f$, 5-7 membered cycloalkyl, 5-7 membered heterocyclyl, 5-7 membered heteroaryl and phenyl;

$R^2$ is phenyl, which is optionally substituted with $R^{2a}$, wherein $R^{2a}$ is selected from the group consisting of hydrogen, halogen and $C_{1-6}$ alkyl;

$R^b$ is selected from the group consisting of hydrogen, $C_{1-6}$ alkyl, halogenated $C_{1-6}$ alkyl and $C_{1-6}$ alkoxy $C_{1-6}$ alkyl;

$R^c$ is selected from the group consisting of hydrogen, $C_{1-6}$ alkyl, halogenated $C_{1-6}$ alkyl and $C_{1-6}$ alkoxy; and $R^d$, $R^e$ and $R^f$ are independently of each other selected from the group consisting of hydrogen, $C_{1-6}$ alkyl and halogenated $C_{1-6}$ alkyl.

9. The compound, the pharmaceutically acceptable salt and the stereoisomer thereof according to embodiment 3: wherein, $R^1$ is selected from the group consisting of

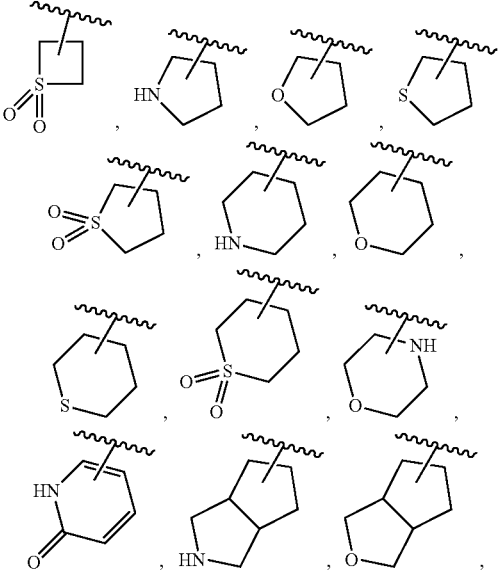

-continued

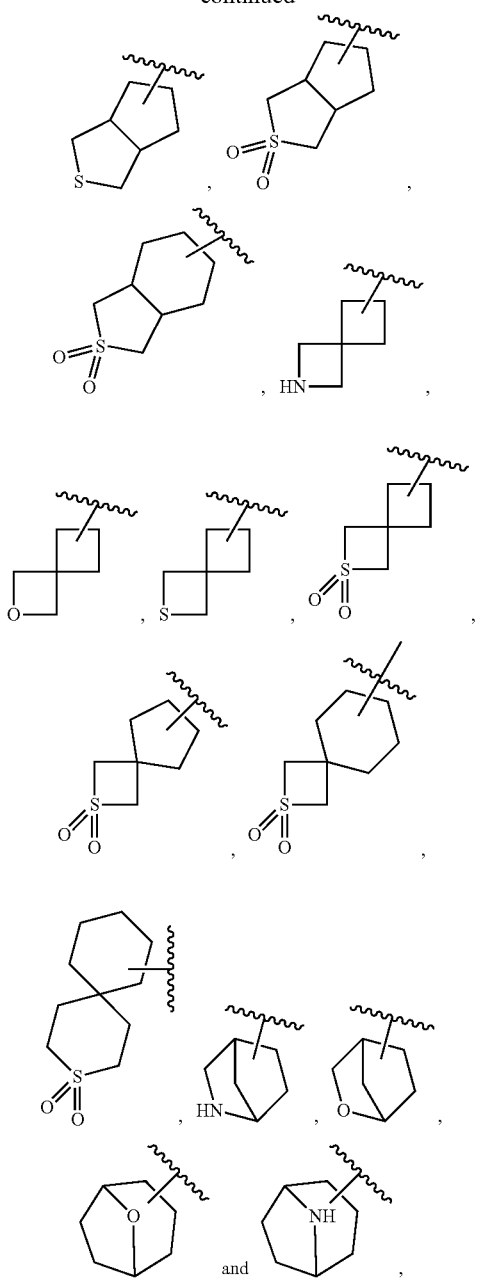

which is optionally substituted with $R^{1a}$, wherein $R^{1a}$ is selected from the group consisting of hydrogen, halogen, $C_{1-4}$ alkyl, halogenated $C_{1-4}$ alkyl, —CN, —NO$_2$, —OR$^b$, —C(O)R$^c$, —C(O)OR$^b$, —OC(O)R$^c$, —C(O)NR$^e$R$^f$, —OC(O)NR$^e$R$^f$, —NR$^e$R$^f$, —NR$^d$C(O)R$^c$, —NR$^d$C(O)NR$^e$R$^f$, —NR$^d$C(O)OR$^b$, —S(O)$_2$R$^c$ and —S(O)$_2$NR$^e$R$^f$;

$R^2$ is phenyl, which is optionally substituted with $R^{2a}$, wherein $R^{2a}$ is selected from the group consisting of hydrogen, halogen and $C_{1-4}$ alkyl;

$R^3$ is hydrogen or $C_{1-4}$ alkyl;

$R^b$, $R^c$, $R^d$, $R^e$ and $R^f$ are independently of each other hydrogen or $C_{1-4}$ alkyl;

m is 0, 1, 2 or 3; and n is 0, 1, 2 or 3.

$R^1$ is preferably selected from the group consisting of

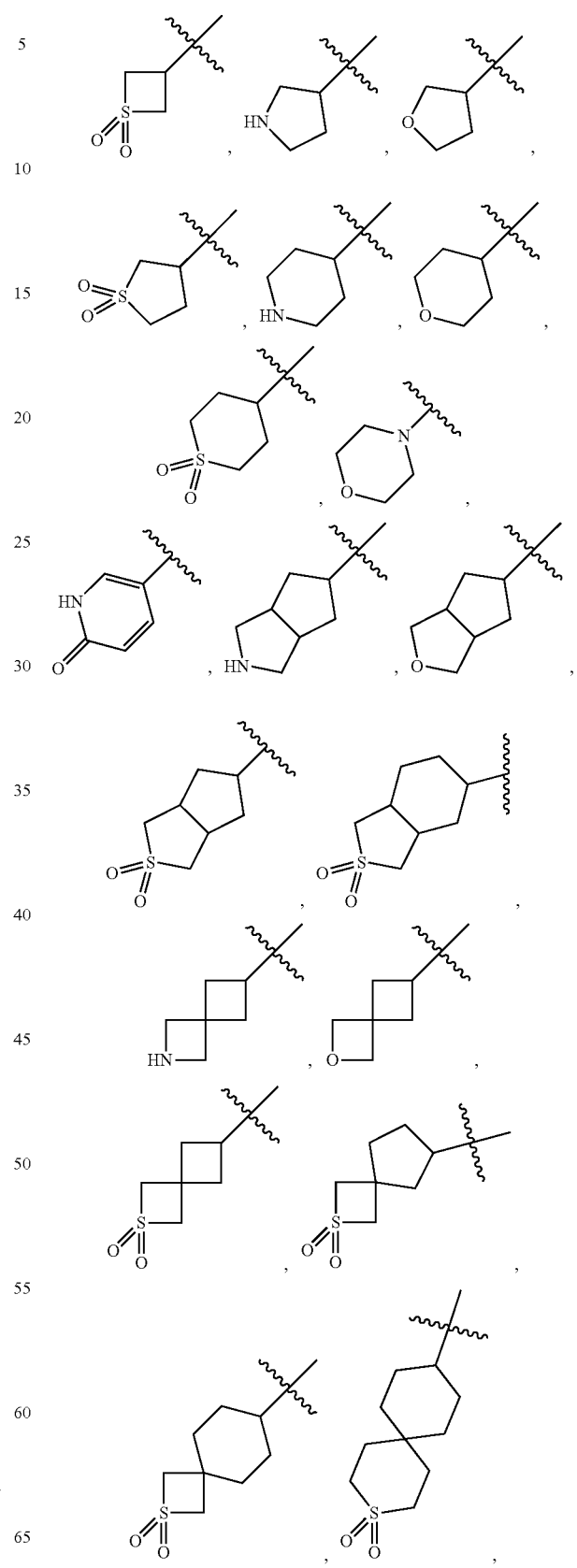

-continued

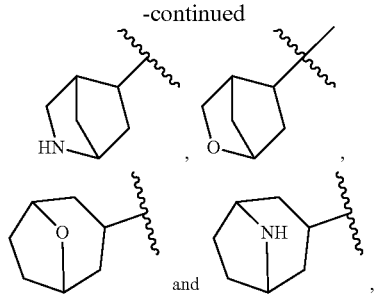

which is optionally substituted with $R^{1a}$, wherein $R^{1a}$ is selected from the group consisting of hydrogen, halogen, $C_{1-4}$ alkyl, halogenated $C_{1-4}$ alkyl, —CN, —NO$_2$, —OR$^b$, —C(O)R$^c$, —C(O)OR$^b$, —OC(O)R$^c$, —C(O)NR$^e$R$^f$, —NR$^e$R$^f$, —NR$^d$C(O)R$^c$, —S(O)$_2$R$^c$ and —S(O)$_2$NR$^e$R$^f$, and $R^b$, $R^c$, $R^d$, $R^e$ and $R^f$ are independently of each other hydrogen or $C_{1-4}$ alkyl.

Preferably, $R^1$ is selected from the group consisting of

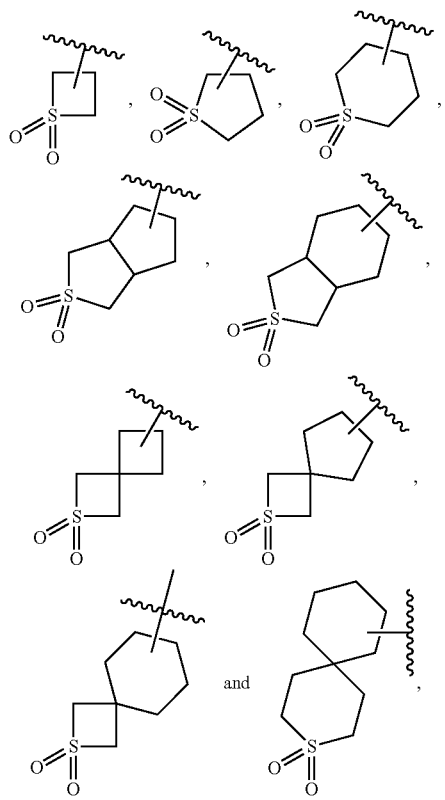

which is optionally substituted with $R^{1a}$, wherein $R^{1a}$ is selected from the group consisting of hydrogen, halogen and $C_{1-4}$ alkyl.

Preferably, $R^1$ is selected from the group consisting of

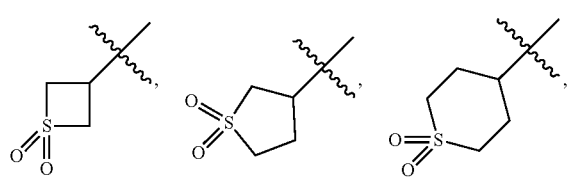

-continued

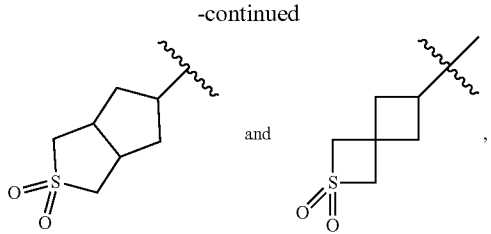

which is optionally substituted with $R^{1a}$, wherein $R^{1a}$ is selected from the group consisting of hydrogen, halogen and $C_{1-4}$ alkyl.

The following compound, a pharmaceutically acceptable salt and a stereoisomer thereof are provided in the present application:

| No. | Structure Formula |
|---|---|
| 1 | ![structure 1] |
| 2 | ![structure 2] |
| 3 | ![structure 3] |
| 4 | ![structure 4] |

| No. | Structure Formula |
|---|---|
| 5 | |
| 6 | |
| 7 | |
| 8 | |
| 9 | |
| 10 | |
| 11 | |
| 12 | |
| 13 | |
| 14 | |
| 15 | |

| No. | Structure Formula |
|---|---|
| 16 | (structure) |
| 17 | (structure) |
| 18 | (structure) |
| 19 | (structure) |
| 20 | (structure) |
| 21 | (structure) |
| 22 | (structure) |
| 23 | (structure) |
| 24 | (structure) |
| 25 | (structure) |
| 26 | (structure) |

Another technical solution of the present invention provides a pharmaceutical composition comprising a compound of Formula I and Formula II, a pharmaceutically acceptable salt thereof, and a stereoisomer thereof, which may optionally comprise one or more pharmaceutically acceptable carriers, and may be made into any pharmaceutically acceptable dosage form. The pharmaceutical composition can be administered to a patient or subject in need of such treatment by any suitable mode of administration, such as oral, parenteral, rectal or pulmonary administration. For oral administration, the pharmaceutical composition can be prepared into a conventional solid preparation such as a tablet, a capsule, a pill, a granule, and the like; or an oral liquid preparation such as an oral solution or an oral suspension, a syrup, and the like. When an oral preparation is prepared, a suitable filler, a binder, a disintegrant, a lubricant, and the like may be added. For parenteral administration, the pharmaceutical composition can be prepared as an injection, including an injection liquid, a sterile powder for injection, and a concentrated solution for injection. When the injection is prepared, it can be produced by a conventional method in the prior art. The injection may be prepared without an additional agent, or with a suitable additive depending on the properties of the drug. For rectal administration, the pharmaceutical composition can be formulated as a suppository and the like. For pulmonary administration, the pharmaceutical composition can be formulated as an inhalant or a spray, and the like.

Another technical solution of the present invention provides use of a compound of Formula I and Formula II, a pharmaceutically acceptable salt, and a stereoisomer thereof in the manufacture of a medicament for treating a disease mediated by IDO abnormality, particularly cancer-associated tumor-specific immunosuppression.

The disease mediated by IDO abnormality is an infectious disease, a nervous system disease, a cancer or a non-cancerous proliferative disease. The infectious disease includes those caused by the infection of influenza virus, hepatitis C virus (HCV), human papillomavirus (HPV), cytomegalovirus (CMV), E-B virus (EBV), poliovirus, varicella zoster virus, Coxsackie virus or human immunodeficiency virus (HIV); the nervous system disease includes: Alzheimer's disease, depression; the cancer includes lung cancer, squamous cell carcinoma, bladder cancer, gastric cancer, ovarian cancer, peritoneal cancer, breast cancer, ductal carcinoma of the breast, head and neck cancer, endometrial cancer, uterine body cancer, rectal cancer, liver cancer, kidney cancer, renal pelvic cancer, esophageal cancer, esophageal adenocarcinoma, glioma, prostate cancer, thyroid cancer, female reproductive system cancer, carcinoma in situ, lymphoma, neurofibromatosis, bone cancer, skin cancer, brain cancer, colon cancer, testicular cancer, gastrointestinal stromal tumor, oral cancer, pharyngeal cancer, multiple myeloma, leukemia, non-Hodgkin's lymphoma, large intestine villus adenoma, melanoma, cell tumor, and sarcoma; the non-cancerous proliferative disease refers to those caused by abnormal hyperplasia of immune organs, immune tissues or immune cells (including benign or malignant), exhibiting immune dysfunction or elevated immunoglobulin levels, for example, myeloproliferative disorders and lymphoproliferative diseases.

BRIEF DESCRIPTION OF THE DRAWING

FIG. 1 shows the $^1$H NMR spectrum of Compound 2.

DETAILED DESCRIPTION OF THE INVENTION

The "halogen" as used in the present invention refers to fluorine, chlorine, bromine, iodine and the like, preferably fluorine atom or chlorine atom.

As used herein, "halogenated" means that any carbon atom in the substituent may be substituted by one or more of the same or different halogens. "Halogen" is as defined above.

The "$C_{1-6}$ alkyl" as used in the present invention refers to a linear or branched alkyl derived by removing one or more hydrogen atom from a alkane moiety having 1 to 6 carbon atoms, such as methyl, ethyl, n-propyl or isopropyl, n-butyl, isobutyl, sec-butyl, tert-butyl, n-pentyl, isopentyl, 2-methylbutyl, neopentyl, 1-ethylpropyl, n-hexyl, isohexyl, 4-methylpentyl, 3-methylpentyl, 2-methylpentyl, 1-methylpentyl, 3,3-dimethylbutyl, 2,2-dimethylbutyl, 1,1-dimethylbutyl, 1,2-dimethylbutyl, 1,3-dimethylbutyl, 2,3-dimethylbutyl, 2-ethylbutyl and 1-methyl-2-methylpropyl and the like. The "$C_{1-4}$ alkyl" means the above examples containing 1 to 4 carbon atoms.

The "$C_{2-6}$ alkenyl" as used in the present invention refers to a linear or branched alkenyl derived by removing one or more hydrogen atom from an olefin moiety having 2 to 6 carbon atoms containing at least one carbon-carbon double bond, such as vinyl, 1-propenyl, 2-propenyl, 1-butenyl, 2-butenyl, 1,3-butadienyl, 1-pentenyl, 2-pentenyl, 3-pentenyl, 1,3-pentadienyl, 1,4-pentadienyl, 1-hexenyl, 1,4-hexadienyl, and the like.

The "$C_{2-6}$ alkynyl" as used in the present invention refers to a linear or branched alkynyl derived by removing one or more hydrogen atom from an alkyne moiety having 2 to 6 carbon atoms containing at least one carbon-carbon triple bond, such as ethynyl, propynyl, 2-butynyl, 2-pentynyl, 3-pentynyl, 4-methyl-2-pentynyl, 2-hexynyl, 3-hexynyl and the like.

The "$C_{1-6}$ alkoxy" as used in the present invention refers to a group in which "$C_{1-6}$ alkyl" as defined above is bonded to a parent molecular moiety through an oxygen atom, that is, a "$C_{1-6}$ alkyl-O—" group, such as methoxy, ethoxy, propoxy, isopropoxy, n-butoxy, tert-butoxy, n-pentyloxy, neopentyloxy and n-hexyloxy. The "$C_{1-4}$ alkoxy" refers to the above-mentioned example having 1 to 4 carbon atoms, that is, a "$C_{1-4}$ alkyl-O—" group.

The "fused ring" as used in the present invention refers to a polycyclic ring structure formed by joining two or more cyclic structures connected by an ortho-, spiro- or bridged linkage. The ortho-cyclic structure refers to a fused ring structure formed by two or more ring structures sharing two adjacent ring atoms with each other (i.e., sharing one bond). The bridged cyclic structure refers to a fused ring structure formed by two or more ring-shaped structures sharing two non-adjacent ring atoms with each other. The spiro-cyclic structure refers to a fused ring structure formed by two or more ring structures sharing one ring atom with each other.

The "cycloalkyl" of the present invention may be a 3-14 membered cycloalkyl group, including a monocyclic cycloalkyl group or a fused cycloalkyl group, which may be saturated, partially saturated or unsaturated, but not aromatic. The monocyclic cycloalkyl group may be a 3-8 membered cycloalkyl group or a 5-7 membered cycloalkyl group, and examples thereof include, but are not limited to, cyclopropyl, cyclobutyl, cyclopentyl, cyclohexyl, cycloheptyl, cyclooctyl, cyclobutenyl, cyclopentenyl, cyclohexenyl, 1,4-cyclohexadienyl, cycloheptenyl, 1,4-cycloheptadienyl, cyclooctenyl, 1,5-cyclooctadienyl and the like. The fused cycloalkyl group includes an ortho-cycloalkyl group, a bridged cycloalkyl group, a spirocycloalkyl group, and may be saturated, partially saturated or unsaturated, but not aromatic.

The ortho-cycloalkyl group may be a 6-12 membered ortho-cycloalkyl group, a 7-10 membered ortho-cycloalkyl group, and examples thereof include, but are not limited to, bicyclo[3.1.1] heptyl, bicyclo[2.2.1] heptyl, bicyclo[2.2.2] octyl, bicyclo[3.2.2]nonanyl, bicyclo[3.3.1]nonanyl and bicyclo[4.2.1]nonanyl.

The spiro-cyclic group may be a 6-12 membered spiro-cyclic group, a 7-11 membered spiro-cyclic group, and examples thereof include, but are not limited to,

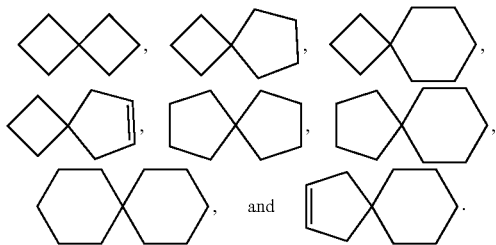

The bridged cyclic group may be a 6-12 membered bridged cyclic group, a 7-11 membered bridged cyclic group, and examples thereof include, but are not limited to,

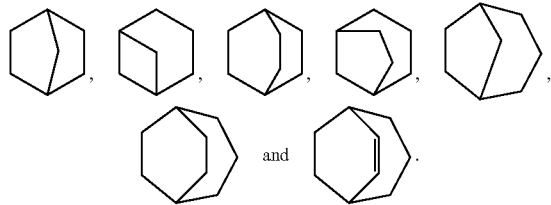

The "heterocyclyl" or "heterocyclyl" as used in the present invention means a non-aromatic cyclic group in which at least one ring carbon atom is replaced by a hetero atom selected from O, S and N, preferably containing 1-3 hetero atoms, including the case where a carbon atom or a sulfur atom is substituted by oxo, for example, a carbon atom is replaced by C(O), S(O) or S(O)$_2$.

The "heterocyclyl" may be a 3-14 membered heterocyclyl or a 3-12 membered heterocyclyl, and includes a monoheterocyclyl or a fused heterocyclyl. The monoheterocyclyl may be a 3-8 membered heterocyclyl, a 3-8 membered saturated heterocyclyl, a 3-6 membered heterocyclyl, a 4-6 membered heterocyclyl, a 5-7 membered heterocyclyl, a 5-6 membered heterocyclyl, a 5-6 membered oxygen-containing heterocyclyl, a 5-6 membered nitrogen-containing heterocyclyl, a 5-6 membered saturated heterocyclyl, a 5-7 membered saturated heterocyclyl and the like. Examples thereof include, but are not limited to, aziridinyl, 2H-aziridinyl, diaziridinyl, 3H-diazirinyl, azetidinyl, 1,4-dioxanyl, 1,3-dioxanyl, 1,3-dioxolyl, 1,4-dioxadienyl, tetrahydrofuranyl, dihydropyrrolyl, pyrrolidinyl, imidazolidinyl, 4,5-dihydroimidazolyl, pyrazolidinyl, 4,5-dihydropyrazolyl, 2,5-dihydrothienyl, tetrahydrothiophenyl, 4,5-dihydrothiazolyl, piperidinyl, piperazinyl, morpholinyl, hexahydropyrimidinyl, hexahydropyridazinyl, 4,5-dihydrooxazolyl, 4,5-dihydroisoxazolyl, 2,3-dihydroisoxazolyl, 2H-1,2-oxazinyl, 6H-1,3-oxazinyl, 4H-1,3-thiazinyl, 6H-1,3-thiazinyl, 2H-pyranyl, 2H-pyran-2-one, 3,4-dihydro-2H-pyranyl, 1,1-dioxotetrahydrothiopyranyl, 1,1-dioxotetrahydrothiophenyl, thietane 1,1-dioxide, etc.

The fused heterocyclyl includes an ortho-heterocyclyl, a spiro-heterocyclyl, a bridged heterocyclyl, and may be saturated, partially saturated or unsaturated, but not aromatic.

The ortho-heterocyclyl may be a 6-12 membered ortho-heterocyclyl, a 7-10 membered ortho-heterocyclyl, a 6-12 membered saturated ortho-heterocyclyl, a 7-8 membered saturated ortho-heterocyclyl, and an 8-membered saturated ortho-heterocyclyl, and examples thereof include, but are not limited to, 3-azabicyclo[3.1.0]hexyl, 3,6-diazabicyclo[3.2.0]heptyl, 3,8-diazabicyclo[4.2.0]octyl, 3,7-diazabicyclo[4.2.0]octyl, octahydropyrrolo[3,4-c]pyrrolyl, octahydropyrrolo[3,4-b]pyrrolyl, octahydropyrrolo[3,4-b][1,4]oxazinyl, octahydro-1H-pyrrolo[3,4-c]pyridinyl, 2,3-dihydrobenzofuran-2-yl, 2,3-dihydrobenzofuran-3-yl, indolin-1-yl, indolin-2-yl, indolin-3-yl, 2,3-dihydrobenzothien-2-yl, octahydro-1H-indolyl, octahydrobenzofuranyl, octahydrocyclopenta[c]pyrrolyl, hexahydrocyclopenta[c]furanyl, 2,2-dioxo hexahydrocyclopenta[c]thienyl.

The spiro-heterocyclyl may be a 6-12 membered spiro-heterocyclyl, a 7-11 membered spiro-heterocyclyl, a 6-12 membered saturated spiro-heterocyclyl, a 7 membered saturated spiro-heterocyclyl, examples thereof include but not Limited to:

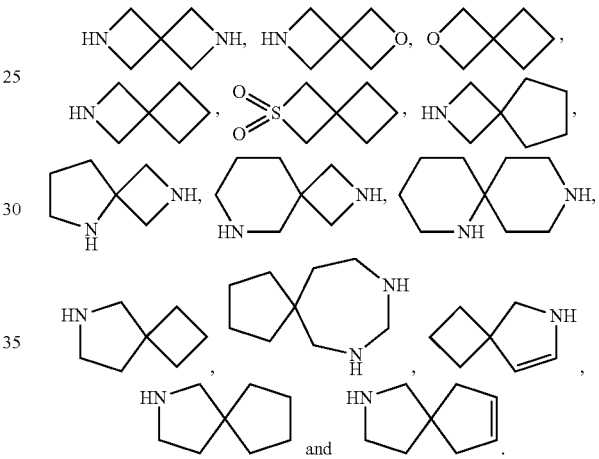

The bridged heterocyclyl may be a 6-12 membered bridged heterocyclyl, a 7-11 membered bridged heterocyclyl, a 6-12 membered saturated bridged cyclic group, and a 7-8 membered saturated bridged cyclic group, examples thereof include but are not limited to:

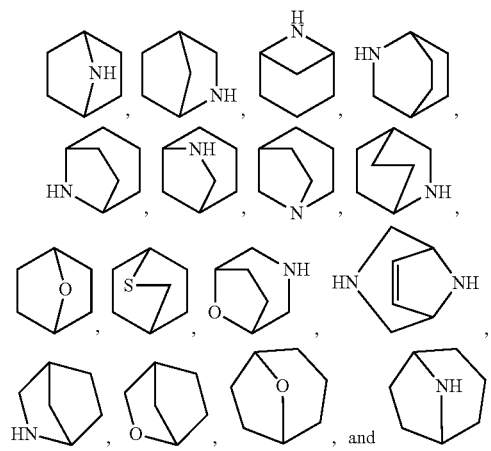

The aryl group means an aromatic carbocyclic group including a 6-8 membered monocyclic aryl group and an 8-14 membered fused aryl group. A 6-8 membered monocyclic aryl group is for example phenyl, cyclooctatetraenyl and the like. An 8-14 membered fused aryl group is for example naphthalene, phenanthrene and the like.

The "heteroaryl" as used in the present invention may be a 5-14 membered heteroaryl, and means an aromatic cyclic group in which at least one ring carbon atom is replaced by a hetero atom selected from O, S, N, preferably containing 1-3 heteroatoms, including the case where a carbon atom or a sulfur atom is oxidized, for example, a carbon atom is replaced by C(O), S(O), or S(O)2. A heteroaryl group includes monoheteroaryl and fused heteroaryl. The monoheteroaryl group may be a 5-7 membered heteroaryl group, a 5-6 membered heteroaryl group, and the examples thereof include, but are not limited to, furyl, imidazolyl, isoxazolyl, thiazolyl, isothiazolyl, oxadiazolyl, oxazolyl, isoxazolyl, pyridyl, pyridinonyl, pyridazinyl, pyrimidinyl, pyrazinyl, pyrazolyl, pyrrolyl, tetrazolyl, thiadiazolyl, thiazolyl, thienyl, triazolyl and triazinyl. The fused heteroaryl group may be a 8-12 membered ortho-heteroaryl group, a 9-10 membered ortho-heteroaryl group, and examples thereof include, but are not limited to, benzimidazolyl, benzofuranyl, benzothienyl, benzothiophenyl, benzooxadiazolyl, benzothiazolyl, cinnolinyl, oxazolyl, indolyl, isoquinolyl, naphthyridinyl, purinyl and quinolyl.

A "pharmaceutically acceptable salt" as used herein refers to an addition salt of a pharmaceutically acceptable acid and base of a compound of Formula I or Formula II. In the case where an acidic functional group (such as —COOH, —OH, —SO₃H, etc.) is present in the compound, a "pharmaceutically acceptable salt" includes a salt formed with an appropriate inorganic or organic cation (alkali), including a salt formed with an alkali metal or an alkaline earth metal, an ammonium salt, and a salt formed with a nitrogen-containing organic alkali. In the case where an alkali functional group (such as —NH₂ etc.) is present in the compound, a "pharmaceutically acceptable salt" includes a salt formed with an appropriate inorganic or organic anion (acid), including a salt formed with an inorganic or organic acid. Such a "pharmaceutically acceptable salt" include, but are not limited to, a salt derived from an acid such as hydrochloric acid, phosphoric acid, hydrobromic acid, sulfuric acid, sulfurous acid, formic acid, toluenesulfonic acid, methanesulfonic acid, nitric acid, benzoic acid, citric acid, tartaric acid, maleic acid, hydroiodic acid, alkanoic acid (such as acetic acid, HOOC—(CH₂)ₙ—COOH (where n is 0 to 4)), etc.; a salt derived from a base such as sodium, potassium, calcium, ammonium, and the like.

The term "stereoisomer" as used in the present invention means that an enantiomer can be produced due to an asymmetric carbon atom in the compound of formula I or formula II; a cis-trans isomer can be produced due to a carbon-carbon double bond or a cyclic structure in the compound; a tautomer can be produced due to a ketone or oxime in the compound. All of the enantiomer, diastereomer, racemic isomer, cis-trans isomer, tautomers, geometric isomers and epimers of the compound of Formula I or Formula II, and mixtures thereof are included within the scope of the invention.

For example,

In the case where

is present,

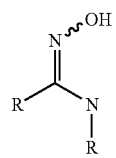

may be produced.

In the case where

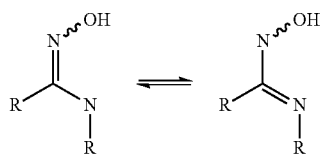

is present,

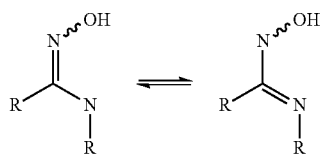

may be produced.

Embodiments

EA: ethyl acetate

PE: petroleum ether

DMA: N,N-dimethylacetamide

THF: tetrahydrofuran

DCM: dichloromethane

TEA: triethanolamine

TFA: trifluoroacetic acid

Preparation Example 1: Synthesis of 4-amino-N-(3-bromo-4-fluorophenyl)-N'-hydroxy-1,2,5-oxadiazol-3-formamidine

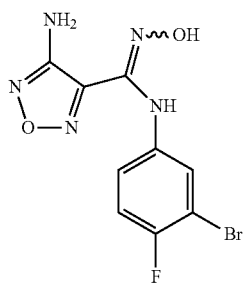 [SMILES: Nc1nonc1C(=NO)Nc1ccc(F)c(Br)c1]

Step 1: Synthesis of 4-amino-N'-hydroxy-1,2,5-oxadiazol-3-formamidine

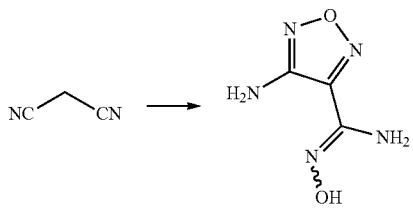 [SMILES: N#CCC#N ; NC(=NO)c1nonc1N]

The raw material malononitrile (50.0 g, 0.76 mol, 1.0 eq) was added to a four-necked bottle, dissolved by heating (about 50° C.), added with water (0.5 L), and cooled to about 10° C. in the ice water bath. Sodium nitrite was added in portions (57.72 g, 0.83 mol, 1.1 eq). After addition, hydrochloric acid (6N, 8.5 mL) was added dropwise at 10° C. or lower, and then the mixture was stirred for 0.5 h until the temperature was constant in the ice water bath. The above reaction solution was designated as A. $H_2NOH \cdot HCl$ (158.4 g, 2.28 mol, 3.0 eq) was dissolved in water (255 mL), and the aqueous solution (255 mL) of potassium hydroxide (127.9 g, 2.28 mol, 3.0 eq) was added thereto. After addition, the mixture was stirred at room temperature (25° C.) for 10 min, and the above reaction solution was designated as B. The reaction solution A was cooled to 0° C.-10° C. with the ice water bath, and the reaction solution B was added dropwise to the reaction solution A. After the dropwise addition, the mixture was stirred for 0.5 h in the ice water bath until the temperature was constant, the ice water bath was removed, and the mixture was heated to reflux for 12 hours. After the reaction was completed, hydrochloric acid (6N, 120 mL) was added dropwise in the ice water bath (0° C.), the pH was adjusted to 7, the stirring was continued for 40 min, then the reaction solution was subjected to suction filtration, the filter cake was washed with water and dried under vacuum to obtain the target compound (101 g, yield: 93.5%).

Step 2: Synthesis of 4-amino-N-hydroxy-1,2,5-oxadiazol-3-methylimidoyl chloride

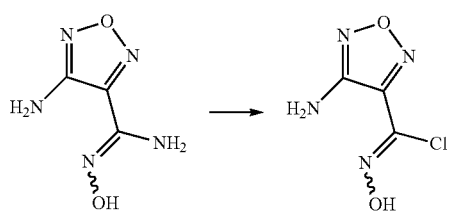 [SMILES: NC(=NO)c1nonc1N ; Nc1nonc1C(Cl)=NO]

4-amino-N'-hydroxy-1,2,5-oxadiazol-3-formamidine (101 g, 0.71 mol, 1.0 eq) was added to the reaction flask, stirred with water (1.4 L), added with HCl (6N, 350 mL) and AcOH (710 mL) with stirring and heated (42° C.-45° C.), stirring until the solution was clarified, added with NaCl (124.5 g, 2.13 mol, 3.0 eq), and dropwise added with an aqueous solution (168 mL) of $NaNO_2$ (48.3 g, 0.70 mol, 0.98 eq) under ice-water bath with stirring over 3.5 h. The mixture was then stirred in ice water bath for 1.5 h, slowly warmed to room temperature (25° C.) with stirring for about 1 h. The reaction solution was subjected to suction filtration. The filter cake was washed with water and dried under vacuum to give 4-amino-N-hydroxy-1,2,5-oxadiazol-3-methylimidoyl chloride (crude 36.78 g, yield: 32%).

Step 3: Synthesis of 4-amino-N-(3-bromo-4-fluorophenyl)-N'-hydroxy-1,2,5-oxadiazol-3-formamidine

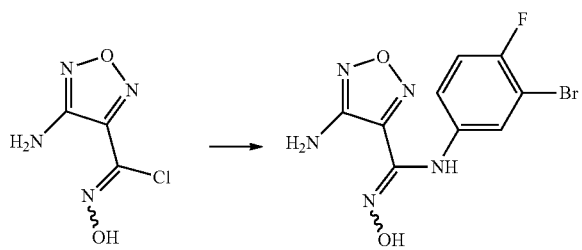 [SMILES: Nc1nonc1C(Cl)=NO ; Nc1nonc1C(=NO)Nc1ccc(F)c(Br)c1]

4-amino-N-hydroxy-1,2,5-oxadiazol-3-methylimidoyl chloride (36.78 g, 0.23 mol, 1.0 eq) was dissolved in water (318 mL) and heated with stirring to 60° C. 3-bromo-4-fluoroaniline (47.50 g, 0.25 mol, 1.1 eq) was added at 60° C. with stirring for about 10 min. The aqueous solution (318 mL) of $NaHCO_3$ (29.40 g, 0.35 mmol, 1.5 eq) was added dropwise over 20 min. After the addition was completed, the mixture was stirred at 60° C. for 30 min, cooled to room temperature, the reaction solution was subjected to suction filtration, the filter cake was washed with water, dried under vacuum, slurried with water overnight, and suction filtration on next day to obtain a gray solid, which was dried to obtain the target product. (61.21 g, yield: 84.2%).

$^1$HNMR (400 MHz, $d_6$-DMSO) δ (ppm): 11.44 (s, 1H), 8.88 (s, 1H), 7.17-7.21 (t, 1H), 7.09-7.12 (d, 1H), 6.75-6.79 (m, 1H), 6.26 (s, 2H).

Molecular Formula: $C_9H_7BrFN_5O_2$, Molecular weight: 316.09, LC-MS (Neg, m/z)=314.0 [M-H$^+$].

Preparation Example 2: Synthesis of 4-(3-bromo-4-fluorophenyl)-3-(4-nitro-1,2,5-oxadiazol-3-yl)-1,2,4-oxadiazol-5(4H)-one

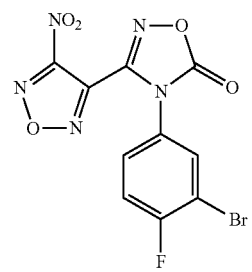 [SMILES: O=c1onc(-c2nonc2[N+](=O)[O-])n1-c1ccc(F)c(Br)c1]

Step 1: Synthesis of 3-(4-amino-1,2,5-oxadiazol-3-yl)-4-(3-bromo-4-fluorophenyl)-1,2,4-oxadiazol-5(4H)-one

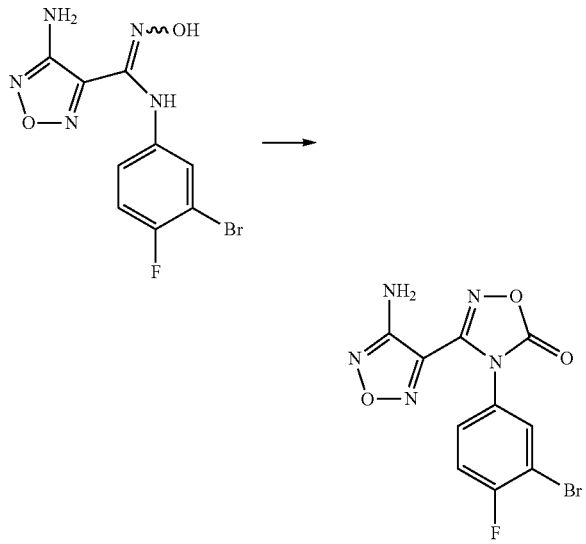

4-amino-N-(3-bromo-4-fluorophenyl)-N'-hydroxy-1,2,5-oxadiazol-3-formamidine (5.0 g, 15.8 mmol, 1.0 eq) was dissolved in ethyl acetate (65 mL), added with carbonyldiimidazole (3.85 g, 23.7 mmol, 1.5 eq), and the mixture was heated at 60° C. and reacted for 0.5 h. The reaction was monitored by TLC until it was complete. The reaction solution was cooled to room temperature and washed with 1 mol/L hydrochloric acid (65 mL×2), the organic phase was combined, separated, concentrated to dry. The resulting crude product was slurried with methyl tert-butyl ether and suction filtration to give 3-(4-amino-1,2,5-oxadiazol-3-yl)-4-(3-bromo-4-fluorophenyl)-1,2,4-oxadiazol-5(4H)-one (3.53 g, yield: 65%).

Step 2: Synthesis of 4-(3-bromo-4-fluorophenyl)-3-(4-nitro-1,2,5-oxadiazol-3-yl)-1,2,4-oxadiazol-5(4H)-one

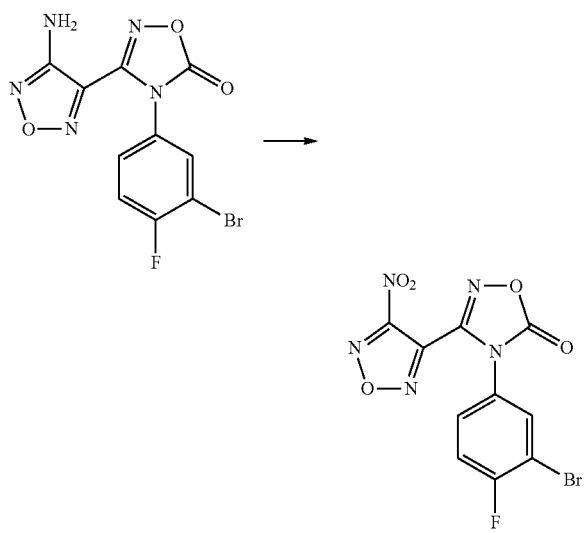

3-(4-amino-1,2,5-oxadiazol-3-yl)-4-(3-bromo-4-fluorophenyl)-1,2,4-oxadiazol-5(4H)-one (264 mg, 0.8 mmol, 1.0 eq) was dissolved in trifluoroacetic acid (5 mL), added with hydrogen peroxide (3 mL, 30%), and reacted at 45° C. for 18 h. The reaction was monitored by TLC until it was complete. The reaction solution was cooled to room temperature and added with saturated sodium bicarbonate solution with ice water bath until no more bubble occurred, and added with EA (3×30 mL) for extraction. The resulting mixture was dried over anhydrous sodium sulfate, suction filtration, the filtrate was concentrated to obtain a crude material, which was purified by silica gel column chromatography (PE:EA=10:1 to 2:1), to give 4-(3-bromo-4-fluorophenyl)-3-(4-nitro-1,2,5-oxadiazol-3-yl)-1,2,4-oxadiazol-5(4H)one (189.9 mg, yield: 66%).

$^1$HNMR (400 MHz, DMSO-d$_6$): 8.06-8.04 (m, 1H), 7.69-7.65 (m, 1H), 7.60-7.55 (m, 1H).

4-(3-bromo-4-fluorophenyl)-3-(4-nitro-1,2,5-oxadiazol-3-yl)-1,2,4-oxadiazol-5(4H)-one prepared in the preparation example can be used in the following examples.

Example 1: Synthesis of N-(3-bromo-4-fluorophenyl)-N'-hydroxy-4-((tetrahydro-2H-pyran-4-yl)amino)-1,2,5-oxadiazol-3-formamidine (Compound 1)

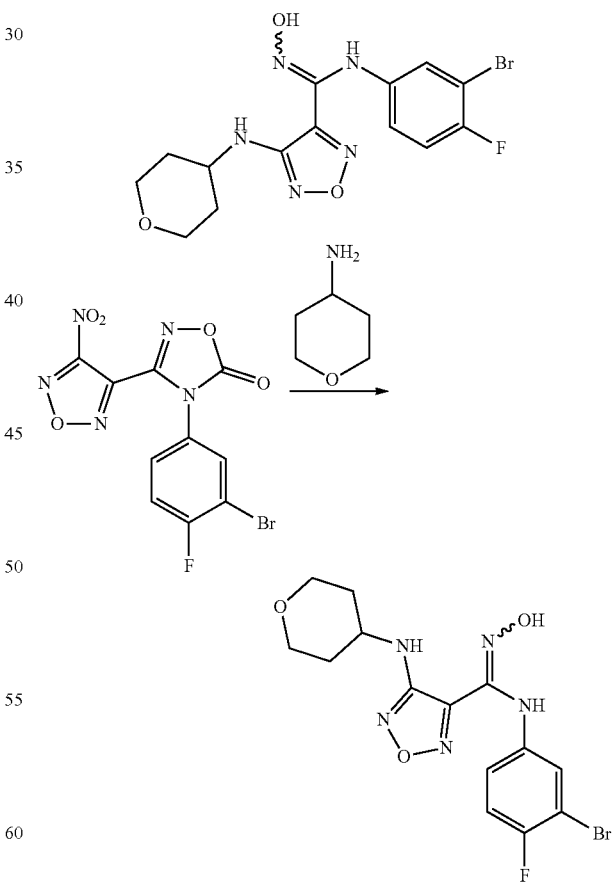

4-(3-bromo-4-fluorophenyl)-3-(4-nitro-1,2,5-oxadiazol-3-yl)-1,2,4-oxadiazol-5(4H)-one (189.9 mg, 0.51 mmol, 1.0 eq) was dissolved in THF (15 mL), added with tetrahydro-2H-pyran-4-amine (103.2 mg, 1.02 mmol, 2.0 eq) and 2 mol/L sodium hydroxide solution (1.5 mL), and stirred for 30 min. The reaction was monitored by TLC until it was complete. The solution was adjusted to a pH of 2-3 with 1 mol/L hydrochloric acid solution, added with EA (3×20 mL) for extraction, and the resulting organic phase was combined. The resulting mixture was dried over anhydrous magnesium sulfate, filtered, concentrated to obtain a crude product, which was subjected to silica gel column chromatography (PE:EA=10: 1-1:1) to give N-(3-bromo-4-fluorophenyl)-N'-hydroxy-4-((tetrahydro-2H-pyran-4-yl)amino)-1,2,5-oxadiazol-3-formamidine (61.3 mg, yield: 30%).

¹HNMR (400 MHz, DMSO-d₆) δ (ppm): 11.47 (s, 1H), 8.89 (s, 1H), 7.11-7.19 (m, 2H), 6.79 (s, 1H), 6.15-6.16 (m, 1H), 3.42 (m, 1H), 3.32-3.39 (m, 2H) 1.91-19.4 (m, 1H), 1.46-1.49 (m, 2H).

Molecular Formula: $C_{14}H_{15}BrFN_5O_3$ Molecular weight: 400.21 LC-MS (Neg, m/z)=400.0 [M–H⁺].

Example 2: Synthesis of N-(3-bromo-4-fluorophenyl)-4-((1,1-dioxotetrahydro-2H-thiopyran-4-yl)amino)-N'-hydroxy-1,2,5-oxadiazol-3-formamidine (Compound 2)

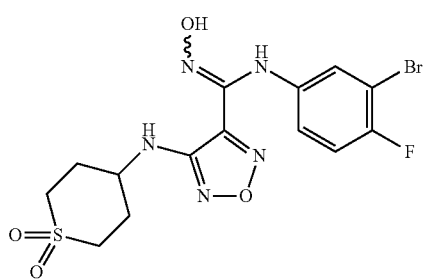 [SMILES: O=S1(=O)CCC(Nc2nonc2C(=NO)Nc2ccc(F)c(Br)c2)CC1]

Step 1: Synthesis of 4-(3-bromo-4-fluorophenyl)-3-(4-((1,1-dioxotetrahydro-2H-thiopyran-4-yl)amino)-1,2,5-oxadiazol-3-yl)-1,2,4-oxadiazol-5 (4H)one

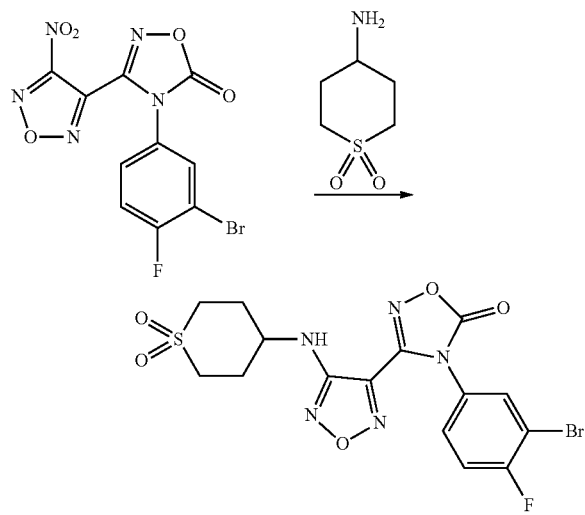

4-(3-bromo-4-fluorophenyl)-3-(4-nitro-1,2,5-oxadiazol-3-yl)-1,2,4-oxadiazol-5(4H)-one (250.4 mg, 0.67 mmol, 1.0 eq) was dissolved in DMA (4 mL), and added with 4-aminotetrahydro-2H-thiopyran-1,1-dioxide (200.8 mg, 1.35 mmol, 2.0 eq), reacted with stirring for 1 h in an ice-bath. The reaction was monitored by TLC until it was complete. The resulting mixture was added with water (30 mL), and EA (3×30 mL) for extraction, and the resulting organic phase was combined. The resulting mixture was dried over anhydrous magnesium sulfate, filtered, concentrated to obtain a crude product, which was subjected to silica gel column chromatography (PE:EA=10:1 to 1:1) to give 4-(3-bromo-4-fluorophenyl)-3-(4-((1,1-dioxotetrahydro-2H-thiopyran-4-yl)amino)-1,2,5-oxadiazol-3-yl)-1,2,4-oxadiazol-5(4H)one (78.9 mg, yield: 25%).

Step 2: Synthesis of N-(3-bromo-4-fluorophenyl)-4-((1,1-dioxotetrahydro-2H-thiopyran-4-yl)amino)-N'-hydroxy-1,2,5-oxadiazol-3-formamidine

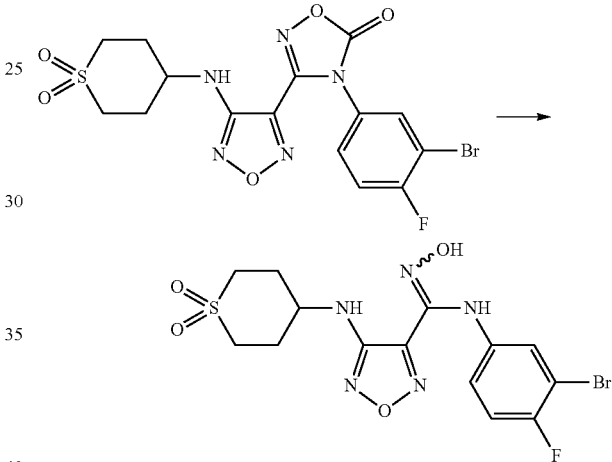

4-(3-bromo-4-fluorophenyl)-3-(4-((1,1-dioxotetrahydro-2H-thiopyran-4-yl)amino)-1,2,5-oxadiazol-3-yl)-1,2,4-oxadiazol-5(4H)one (78.9 mg, 0.17 mmol, 1.0 eq) was dissolved in THF (10 mL), added with 2 mol/L sodium hydroxide solution (2 mL), and reacted with stirring for 30 min. The reaction was monitored by TLC until it was complete. The solution was adjusted to a pH of 2-3 with 1 mol/L hydrochloric acid solution, added with EA (3×20 mL) for extraction, and the resulting organic phase was combined. The resulting mixture was dried over anhydrous magnesium sulfate, filtered, concentrated to obtain a crude product, which was subjected to silica gel column chromatography (PE:EA=10: 1-1:1) to give N-(3-bromo-4-fluorophenyl)-4-((1,1-dioxotetrahydro-2H-thiopyran-4-yl)amino)-N'-hydroxy-1,2,5-oxadiazol-3-formamidine (26 mg, yield: 35%).

¹HNMR (400 MHz, DMSO-d₆) δ (ppm): 11.42 (s, 1H), 8.91 (s, 1H), 7.18 (m, 1H), 7.09-7.10 (m, 1H), 6.77-6.79 (m, 1H), 6.37-6.39 (m, 1H), 3.70-3.72 (m 1H), 3.07-3.07 (m, 2H), 2.20 (3, 3H), 2.02-2.05 (m, 3H).

Molecular Formula: $C_{14}H_{15}BrFN_5O_4S$ Molecular weight: 448.27 LC-MS (m/z)=448.0 [M–H⁺].

Example 3: Synthesis of N-(3-bromo-4-fluorophenyl)-N'-hydroxy-4-((1-(methylsulfonyl)piperidin-4-yl)amino)-1,2,5-oxadiazol-3-formamidine (Compound 3)

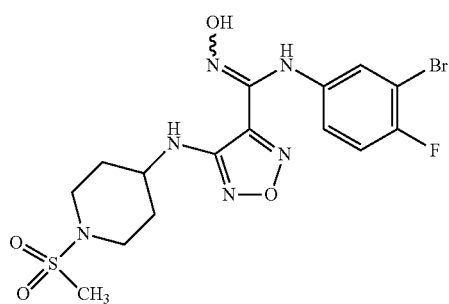 [SMILES: CS(=O)(=O)N1CCC(Nc2nonc2C(=NO)Nc2ccc(F)c(Br)c2)CC1]

Step 1: Synthesis of 4-(3-bromo-4-fluorophenyl)-3-(4-((1-(methylsulfonyl)piperidin-4-yl)amino)-1,2,5-oxadiazole-3-yl)-1,2,4-oxadiazol-5 (4H)-one

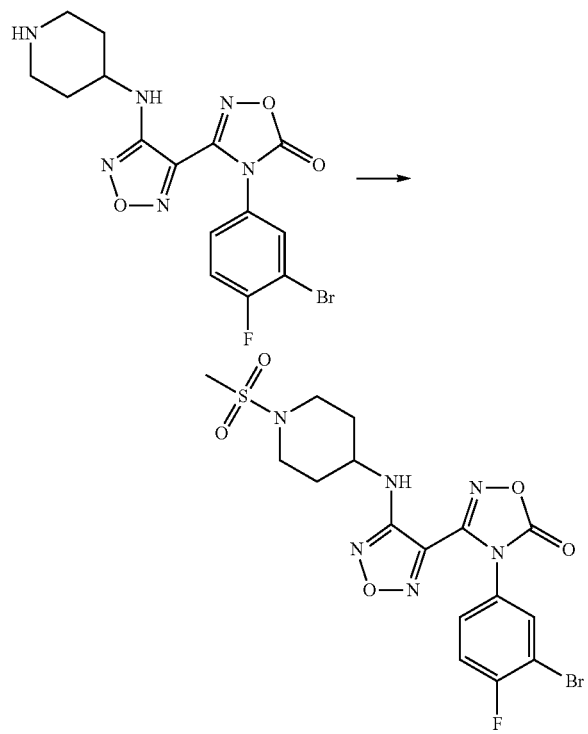

4-(3-bromo-4-fluorophenyl)-3-(4-(piperidin-4-yl-amino)-1,2,5-oxadiazol-3-yl)-1,2,4-oxadiazole-5(4H)-one (161.9 mg, 0.382 mmol) (obtained in step 2 for preparing compound 4) was dissolved in DCM (3 mL), added with triethylamine (116.0 mg, 1.146 mmol, 3.0 eq) and added dropwise with methanesulfonyl chloride (62.3 mg, 0.573 mmol, 1.5 eq). The mixture was reacted for 1 h. The reaction was monitored by TLC until it was complete. The resulting mixture was added with water (10 mL), and EA (3×15 mL) for extraction, and the resulting organic phase was combined. The resulting mixture was dried over anhydrous magnesium sulfate, filtered, concentrated on a rotary evaporator to obtain a crude product of 4-(3-bromo-4-fluorophenyl)-3-(4-((1-(methylsulfonyl)piperidin-4-yl)amino)-1,2,5-oxadiazole-3-yl)-1,2,4-oxadiazol-5(4H)-one (170.0 mg, yield: 88.5%).

Step 2: Synthesis of N-(3-bromo-4-fluorophenyl)-N'-hydroxy-4-((1-(methylsulfonyl)piperidin-4-yl)amino)-1,2,5-oxadiazol-3-formamidine

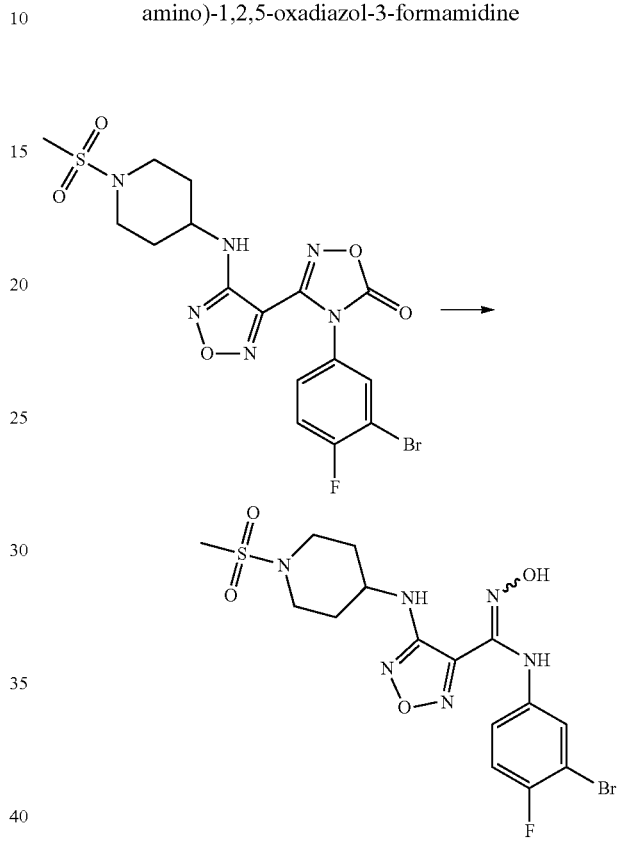

4-(3-bromo-4-fluorophenyl)-3-(4-((1-(methyl sulfonyl)piperidin-4-yl)amino)-1,2,5-oxadiazole-3-yl)-1,2,4-oxadiazol-5(4H)-one (160.0 mg, 0.32 mmol, 1.0 eq) was dissolved in THF (2 mL), added with sodium hydroxide aqueous solution (10%) (3 mL), and reacted with stirring for 30 min at room temperature. The reaction was monitored by TLC until it was complete. The reaction mixture was neutralized with saturated ammonium chloride aqueous solution, added with EA (20 mL×3) for extraction, and the resulting organic phase was combined. The resulting mixture was dried over anhydrous magnesium sulfate, filtered, the filtrate was concentrated to obtain a crude product, which was subjected to silica gel column chromatography (eluent: DCM:MeOH=80:1, 60:1) to give N-(3-bromo-4-fluorophenyl)-N'-hydroxy-4-((1-(methylsulfonyl)piperidin-4-yl)amino)-1,2,5-oxadiazol-3-formamidine (35.0 mg, yield: 23%).

$^1$HNMR (400 MHz, DMSO-$d_6$) δ (ppm): 11.47 (s, 1H), 8.90 (s, 1H), 7.16-7.21 (t, 2H), 6.76-6.78 (d, 1H), 6.19-6.21 (d, 1H), 5.32 (s, 1H), 3.49-3.52 (d, 3H), 3.44 (s, 2H), 3.07 (s, 3H), 2.87 (s, 6H), 1.98-2.05 (m, 4H) 1.52-1.58 (t, 3H).

Molecular Formula: $C_{15}H_{18}BrFN_6O_4S$, Molecular weight: 477.31, LC-MS (Pos, m/z)=477.1 [M+H$^+$].

Example 4: Synthesis of N-(3-bromo-4-fluorophenyl)-N'-hydroxy-4-((1-(sulfamoylpyridin-4-yl)amino)-1,2,5-oxadiazol-3-formamidine (Compound 4)

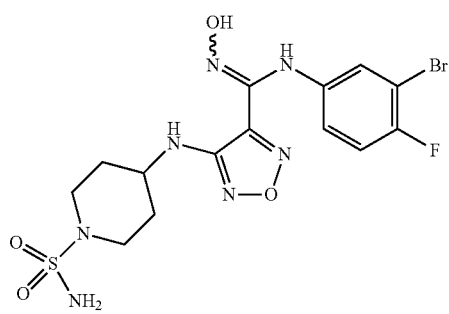 [SMILES: NS(=O)(=O)N1CCC(Nc2nonc2C(=NO)Nc2ccc(F)c(Br)c2)CC1]

Step 1: Synthesis of tert-butyl 4-((4-(4-(3-bromo-4-fluorophenyl)-5-oxo-4,5-dihydro-1,2,4-oxadiazol-3-yl)-1,2,5-oxadiazol-3-yl)amino)piperidine-1-formate

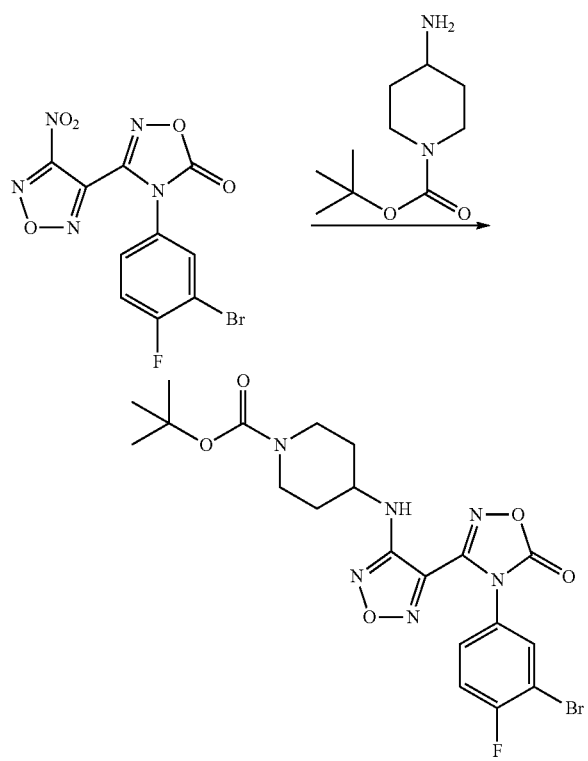

4-(3-bromo-4-fluorophenyl)-3-(4-nitro-1,2,5-oxadiazol-3-yl)-1,2,4-oxadiazol-5 (4H)-one (500.0 mg, 1.34 mmol, 1.0 eq) was dissolved in THF (5 mL), added with tert-butyl 4-aminopiperidine-1-carboxylate (536.4 mg, 2.68 mmol, 2.0 eq) and triethylamine (738.7 mg, 7.3 mmol, 5.4 eq), heated to 75° C. and reacted with stirring overnight. The reaction was monitored by TLC until it was complete. The reaction mixture was added with water (15 mL), and EA (3×20 mL) for extraction, and the resulting organic phase was combined. The resulting mixture was dried over anhydrous magnesium sulfate, filtered, the filtrate was concentrated to obtain a crude product, which was subjected to silica gel column chromatography (PE:EA=10:1 to 1:1), to give tert-butyl 4-((4-(4-(3-bromo-4-fluorophenyl)-5-oxo-4,5-dihydro-1,2,4-oxadiazol-3-yl)-1,2,5-oxadiazol-3-yl)amino)piperidine-1-formate (400.0 mg, yield: 56.9%).

Step 2: Synthesis of 4-(3-bromo-4-fluorophenyl)-3-(4-(piperidin-4-yl-amino)-1,2,5-oxadiazol-3-yl)-1,2,4-oxadiazol-5(4H)-one

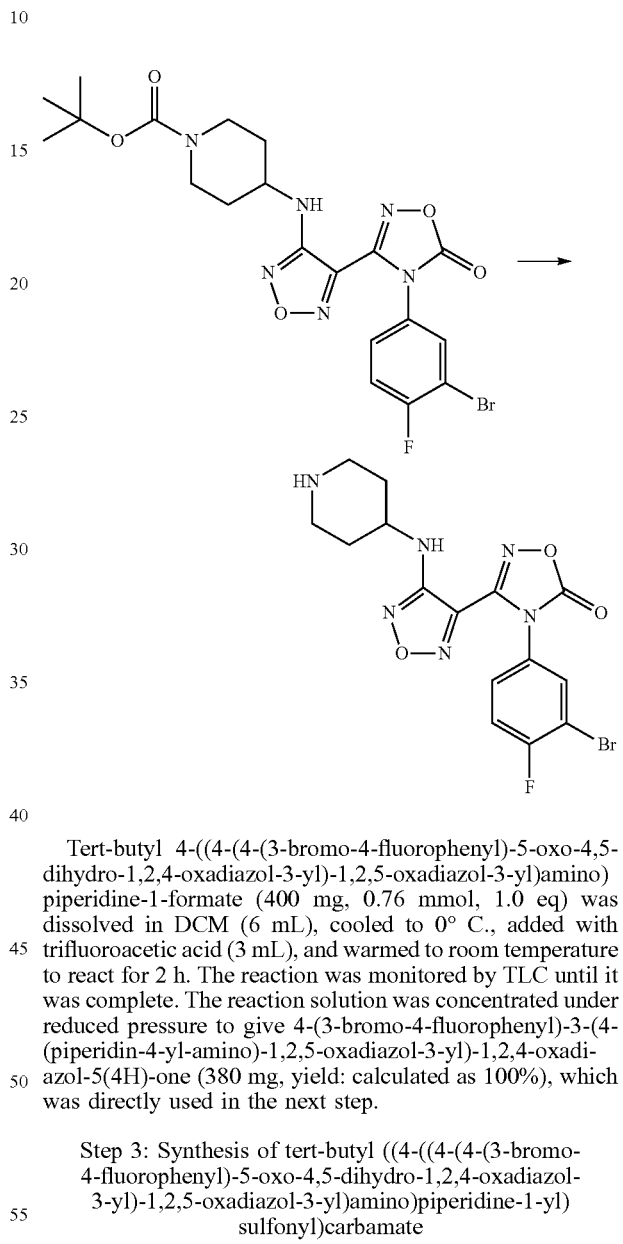

Tert-butyl 4-((4-(4-(3-bromo-4-fluorophenyl)-5-oxo-4,5-dihydro-1,2,4-oxadiazol-3-yl)-1,2,5-oxadiazol-3-yl)amino)piperidine-1-formate (400 mg, 0.76 mmol, 1.0 eq) was dissolved in DCM (6 mL), cooled to 0° C., added with trifluoroacetic acid (3 mL), and warmed to room temperature to react for 2 h. The reaction was monitored by TLC until it was complete. The reaction solution was concentrated under reduced pressure to give 4-(3-bromo-4-fluorophenyl)-3-(4-(piperidin-4-yl-amino)-1,2,5-oxadiazol-3-yl)-1,2,4-oxadiazol-5(4H)-one (380 mg, yield: calculated as 100%), which was directly used in the next step.

Step 3: Synthesis of tert-butyl ((4-((4-(4-(3-bromo-4-fluorophenyl)-5-oxo-4,5-dihydro-1,2,4-oxadiazol-3-yl)-1,2,5-oxadiazol-3-yl)amino)piperidine-1-yl)sulfonyl)carbamate

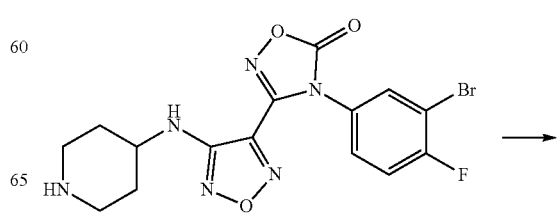

-continued

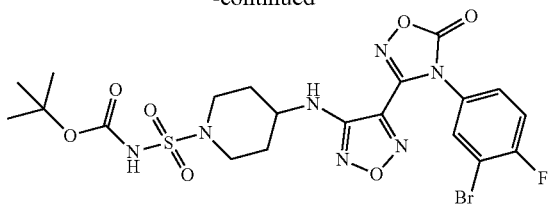

The tert-butanol (34.1 mg, 0.46 mmol, 1.2 eq) was dissolved in DCM (3 mL), cooled to 0° C., chlorosulfonyl isocyanate (65.1 mg, 0.46 mmol) was added dropwise, and reacted at 0° C. for 1.5 hours. The reaction solution was slowly added dropwise to the mixture of 4-(3-bromo-4-fluorophenyl)-3-(4-(piperidin-4-yl-amino)-1,2,5-oxadiazol-3-yl)-1,2,4-oxadiazol-5(4H)-one (161.9 mg, 0.382 mmol, 1.0 eq), TEA (116 mg, 3 eq) and DCM (4 mL), previously cooled to below 0° C. The resulting mixture was stirred for 2 hours at 0° C. for reaction. The reaction was monitored by TLC until it was complete. The reaction mixture was added with water (20 mL) with stirring, ethyl acetate (20 mL×3) for extraction. The organic phase was separated, combined, dried over anhydrous magnesium sulfate, and filtered, the filtrate was concentrated to obtain the crude product of tert-butyl ((4-((4-(4-(3-bromo-4-fluorophenyl)-5-oxo-4,5-dihydro-1,2,4-oxadiazol-3-yl)-1,2,5-oxadiazol-3-yl)amino)piperidin-1-yl) sulfonyl)carbamate (240 mg, yield: calculated as 100%).

Step 4: Synthesis of 4-((4-(4-(3-bromo-4-fluorophenyl)-5-oxo-4,5-dihydro-1,2,4-oxadiazol-3-yl)-1,2,5-oxadiazol-3-yl)amino)piperidine-1-sulfamide

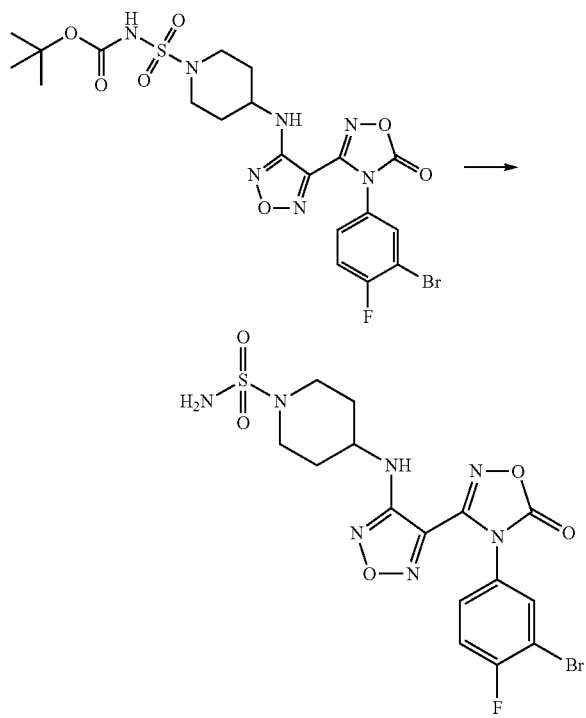

Tert-butyl ((4-((4-(4-(3-bromo-4-fluorophenyl)-5-oxo-4,5-dihydro-1,2,4-oxadiazol-3-yl)-1,2,5-oxadiazol-5-yl)amino)piperidin-1-yl) sulfonyl)carbamate (230.3 mg) was dissolved in DCM (4 mL), cooled to 0° C. in an ice bath, added with TFA (2 mL), and warmed to room temperature to react for 2 h with stirring. The reaction was monitored by TLC until it was complete. The reaction solution was concentrated under reduced pressure to give 4-((4-(4-(3-bromo-4-fluorophenyl)-5-oxo-4,5-dihydro-1,2,4-oxadiazol-3-yl)-1,2,5-oxadiazol-3-yl)amino)piperidine-1-sulfonamide (200 mg crude, yield: calculated as 100%), which was directly used in the next step without purification.

Step 5: Synthesis of N-(3-bromo-4-fluorophenyl)-N'-hydroxy-4-((1-(sulfamoylpiperidin-4-yl)amino)-1,2,5-oxadiazol-3-formamidine

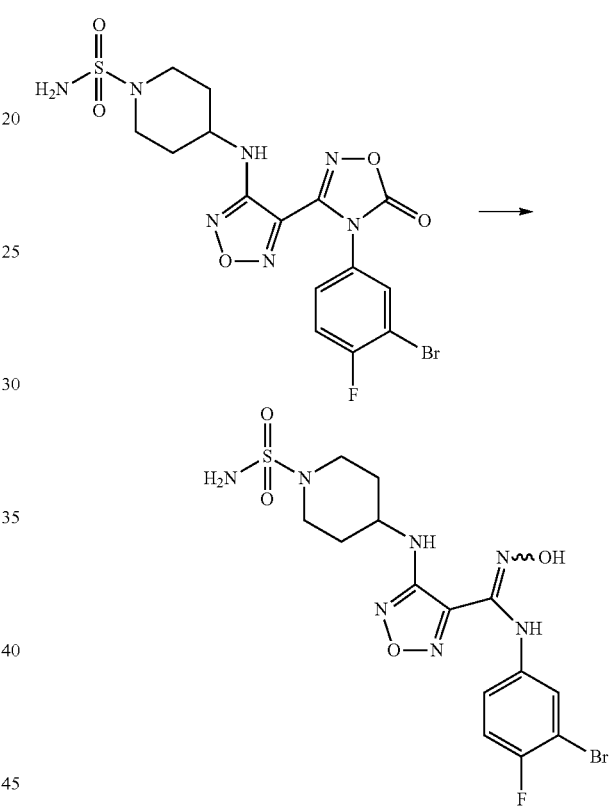

4-((4-(4-(3-bromo-4-fluorophenyl)-5-oxo-4,5-dihydro-1,2,4-oxadiazol-3-yl)-1,2,5-oxadiazol-3-yl)amino)piperidine-1-sulfonamide (192.15 mg, crude) was dissolved in THF (3 mL), added with sodium hydroxide aqueous solution (10%) (6 mL), and reacted with stirring for 1 hour at room temperature. The reaction was monitored by TLC until it was complete. The reaction mixture was neutralized with saturated ammonium chloride aqueous solution, added with EA (20 mL×3) for extraction, and the resulting organic phase was separated and combined. The resulting mixture was dried over anhydrous magnesium sulfate, filtered, the filtrate was concentrated to obtain a crude product, which was subjected to silica gel column chromatography (eluent: DCM:MeOH=100:1 to 80:1) to give N-(3-bromo-4-fluorophenyl)-N'-hydroxy-4-((1-(sulfamoylpiperidin-4-yl)amino)-1,2,5-oxadiazol-3-formamidine (30.0 mg, yield: 16.5%).

$^1$HNMR (400 MHz, DMSO-$d_6$) δ (ppm): 11.48 (s, 1H), 8.89 (s, 1H), 7.11-7.21 (m, 2H), 6.74-6.81 (m, 3H), 3.37-3.45 (m, 3H), 2.66-2.73 (m, 2H), 2.04-2.06 (d, 2H), 1.57-1.60 (t, 2H).

Molecular Formula: $C_{14}H_{17}BrFN_7O_4S$, Molecular weight: 478.30, LC-MS (Pos, m/z)=478.0 [M+H$^+$].

Example 5: Synthesis of N-(3-bromo-4-fluorophenyl)-N'-hydroxy-4-(piperidin-4-yl-amino)-1,2,5-oxadiazol-3-formamidine (Compound 5)

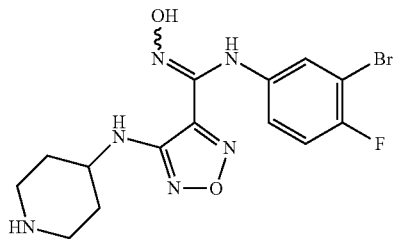 [SMILES: ON=C(Nc1ccc(F)c(Br)c1)c1nonc1NC1CCNCC1]

Step 1: Synthesis of tert-butyl 4-((4-(N-(3-bromo-4-fluorophenyl)-N'-hydroxyamidino)-1,2,5-oxadiazol-3-yl)amino)piperidine-1-formate

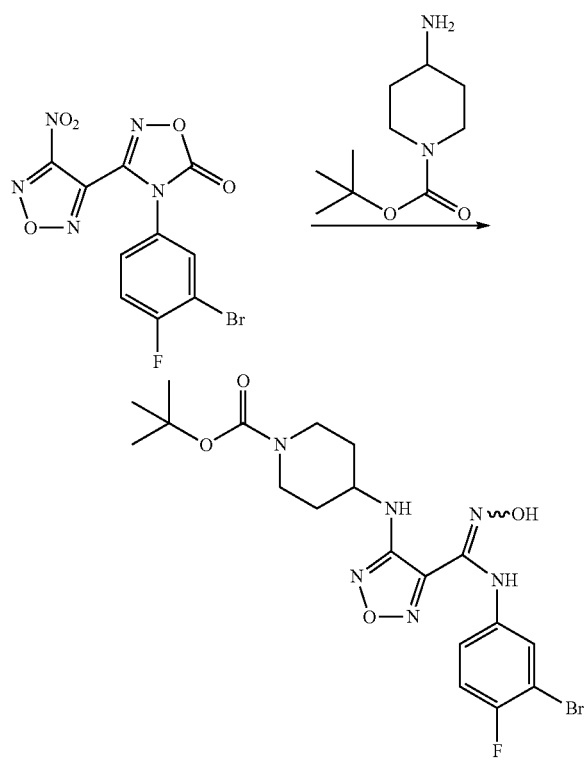

4-(3-bromo-4-fluorophenyl)-3-(4-nitro-1,2,5-oxadiazol-3-yl)-1,2,4-oxadiazol-5(4H)-one (500.0 mg, 1.34 mmol, 1.0 eq) was dissolved in THF (5 mL), added with tert-butyl 4-aminopiperidine-1-carboxylate (536.4 mg, 2.68 mmol, 2.0 eq) and triethylamine (738.7 mg, 7.3 mmol, 5.4 eq), heated to 75° C. and reacted with stirring overnight. The reaction was monitored by TLC until it was complete. The reaction mixture was added with water (15 mL), and EA (3×20 mL) for extraction, and the resulting organic phase was combined. The resulting mixture was dried over anhydrous magnesium sulfate, filtered, concentrated to obtain a crude product, which was subjected to silica gel column chromatography (PE:EA=10:1 to 1:1), to give tert-butyl 4-((4-(N-(3-bromo-4-fluorophenyl)-N'-hydroxyamidino)-1,2,5-oxadiazol-3-yl)amino)piperidine-1-formate (226.0 mg, yield: 33.9%).

Step 2: Synthesis of N-(3-bromo-4-fluorophenyl)-N'-hydroxy-4-(piperidin-4-yl-amino)-1,2,5-oxadiazol-3-formamidine

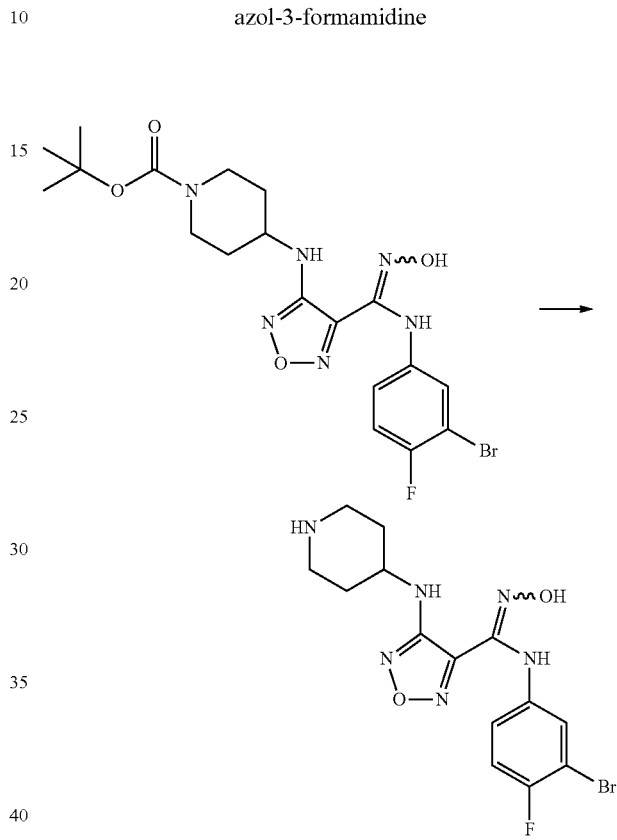

Tert-butyl 4-((4-(N-(3-bromo-4-fluorophenyl)-N'-hydroxyamidino)-1,2,5-oxadiazol-3-yl)amino)piperidine-1-formate (100.0 mg, 0.2 mmol, 1.0 eq) was dissolved in DCM (2 mL), cooled to 0° C., added with trifluoroacetic acid (1 mL), and then warmed to room temperature for 2 h. The reaction was monitored by TLC until it was complete. The reaction mixture was adjusted to pH of 7 with saturated sodium bicarbonate solution, added with EA (3×10 mL) for extraction, and the resulting organic phase was combined. The resulting mixture was dried over anhydrous sodium sulfate to obtain a crude product, which was subjected to silica gel column chromatography (EA:MeOH=30:1, 20:1, 10:1), to give N-(3-bromo-4-fluorophenyl)-N'-hydroxy-4-(piperidin-4-yl-amino)-1,2,5-oxadiazole-3-formamidine (20.0 mg, yield: 25.0%).

$^1$HNMR (400 MHz, DMSO-d$_6$) δ (ppm): 11.49 (s, 1H), 8.91 (s, 1H), 8.64 (s, 1H), 8.44 (s, 1H), 7.16-7.20 (t, 1H), 7.09 (s, 1H), 6.79 (s, 1H), 6.13-6.33 (d, 1H), 5.32 (s, 1H), 4.01-4.03 (d, 1H), 2.08-2.11 (d, 3H), 1.98 (s, 3H), 1.63-1.65 (d, 3H).

Molecular Formula: $C_{14}H_{16}BrFN_6O_2$: Molecular weight: 399.22, LC-MS (Pos, m/z)=399.0 [M+H$^+$].

Example 6: Synthesis of N-(3-bromo-4-fluorophenyl)-N'-hydroxy-4-((2-(methylsulfonypoctahydrocyclopenta[c]pyrrole-5-yl)amino)-1,2,5-oxadiazol-3-formamidine (Compound 8)

Step 1: Synthesis of tert-butyl 5-((4-(4-(3-bromo-4-fluorophenyl)-5-oxo-4,5-dihydro-1,2,4-oxadiazol-3-yl)-1,2,5-oxadiazol-3-yl)amino)hexahydrocyclopenta[c]pyrrole-2(1H)-carboxylate

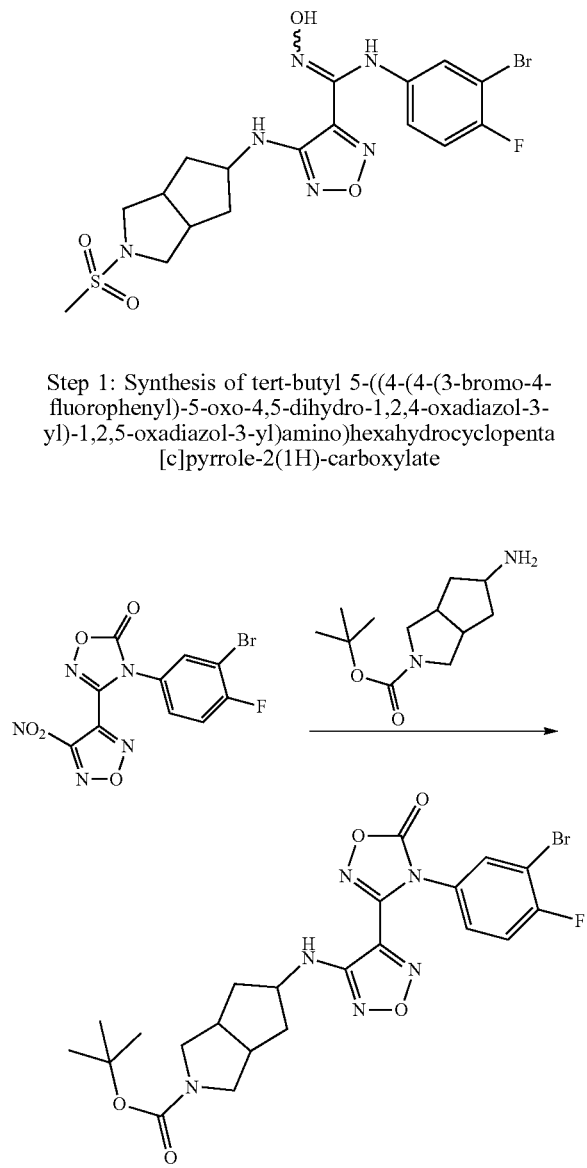

4-(3-bromo-4-fluorophenyl)-3-(4-nitro-1,2,5-oxadiazol-3-yl)-1,2,4-oxadiazol-5(4H)-ketone (543.0 mg, 1.5 mmol, 1.0 eq) was dissolved in THF (6.0 mL), and added with tert-butyl 5-aminohexahydrocyclopenta[c]pyrrole-2(1H)-carboxylate (575.3 mg, 2.2 mmol, 1.5 eq) and triethylamine (819.6 mg, 8.1 mmol, 5.4 eq), reacted with stirring for 1.0 h. The reaction was monitored by TLC until it was complete. The reaction mixture was added with 15.0 mL of water and 6.0 mL of ethyl acetate, and separated. The aqueous phase was extracted with ethyl acetate (2×6.0 mL). The organic phase was combined and washed with saturated brine (15.0 mL), dried over anhydrous sodium sulfate, filtered, concentrated to obtain tert-butyl 5-((4-(4-(3-bromo-4-fluorophenyl)-5-oxo-4,5-dihydro-1,2,4-oxadiazol-3-yl)-1,2,5-oxadiazol-3-yl)amino)hexahydrocyclopenta[c]pyrrole-2 (1H)-carboxylate (810.6 mg, yield: 100%).

Step 2: Synthesis of 4-(3-bromo-4-fluorophenyl)-3-(4-((octahydrocyclopenta[c]pyrrole-5-yl)amino)-1,2,5-oxadiazole-3-yl)-1,2,4-oxadiazol-5(4H)-one

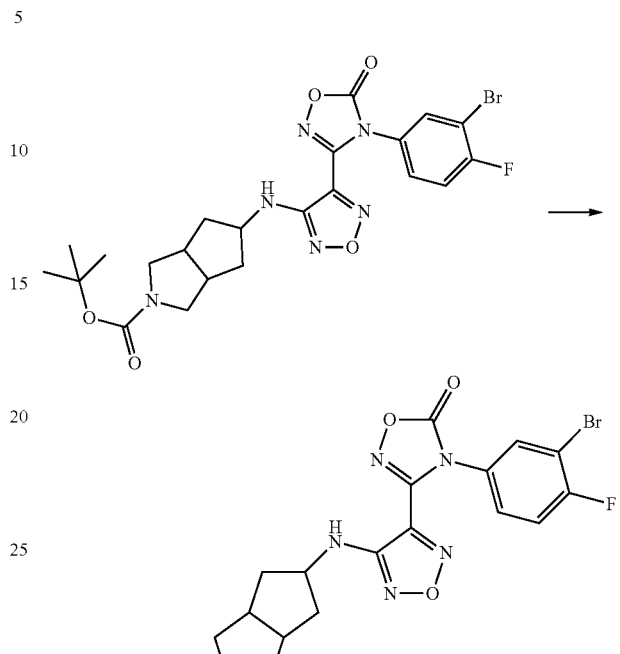

Tert-butyl 5-((4-(4-(3-bromo-4-fluorophenyl)-5-oxo-4,5-dihydro-1,2,4-oxadiazol-3-yl)-1,2,5-oxadiazol-3-yl)amino)hexahydrocyclopenta[c]pyrrole-2 (1H)-carboxylate (581.0 mg, 1.1 mmol, 1.0 eq) dissolved in DCM (6.0 mL), added with trifluoroacetic acid (3.0 mL), and stirred at room temperature for 2.0 h. The reaction was monitored by TLC until it was complete. The reaction solution was concentrated to dryness, added with saturated sodium bicarbonate (10.0 mL) to a neutral pH, added with ethyl acetate (3×5.0 mL) for extraction. The organic phase was combined and washed with saturated brine, dried over anhydrous sodium sulfate, filtered, concentrated to obtain 4-(3-bromo-4-fluorophenyl)-3-(4-((octahydrocyclopenta[c]pyrrole-5-yl)amino)-1,2,5-oxadiazol-3-yl)-1,2,4-oxadiazol-5(4H)-one (278.9 mg, yield: 56.2%).

Step 3: Synthesis of 4-(3-bromo-4-fluorophenyl)-3-(4-((2-(methylsulfonyl) octahydrocyclopenta[c]pyrrole-5-yl)amino)-1,2,5-oxadiazol-3-yl)-1,2,4-oxadiazol-5(4H)-one

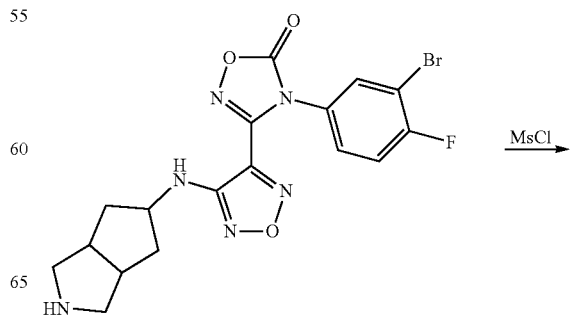

39

-continued

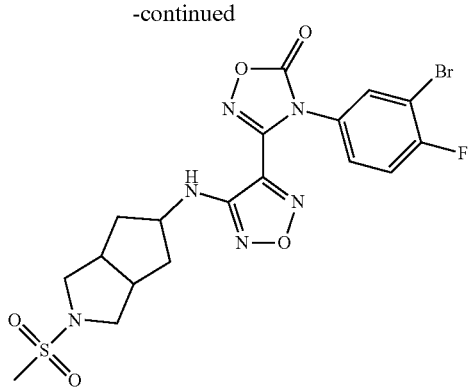

4-(3-bromo-4-fluorophenyl)-3-(4-((octahydrocyclopenta[c]pyrrol-5-yl)amino)-1,2,5-oxadiazol-3-yl)-1,2,4-oxadiazol-5(4H)-one (230.1 mg, 0.51 mmol, 1.0 eq) was dissolved in dichloromethane (4.0 mL), added with triethylamine (154.8 mg, 1.53 mmol, 3.0 eq), slowly added dropwise with methanesulfonyl chloride (87.2 mg, 0.76 mmol, 1.5 eq), and stirred at room temperature for 2.0 h. The reaction was monitored by TLC until it was complete. The reaction solution was added with 10.0 mL of water and extracted with ethyl acetate (5.0 mL×3). The organic phase was washed with saturated brine (15.0 mL), dried over anhydrous sodium sulfate and filtered to give 4-(3-bromo-4-fluorophenyl)-3-(4-((2-(methylsulfonyl) octahydrocyclopenta[c]pyrrole-5-yl)amino)-1,2,5-oxadiazol-3-yl)-1,2,4-oxadiazol-5(4H)-one (250.7 mg, yield: 92.9%).

Step 4: Synthesis of N-(3-bromo-4-fluorophenyl)-N'-hydroxy-4-((2-(methylsulfonyl)octahydrocyclopenta[c]pyrrole-5-yl)amino)-1,2,5-oxadiazol-3-formamidine

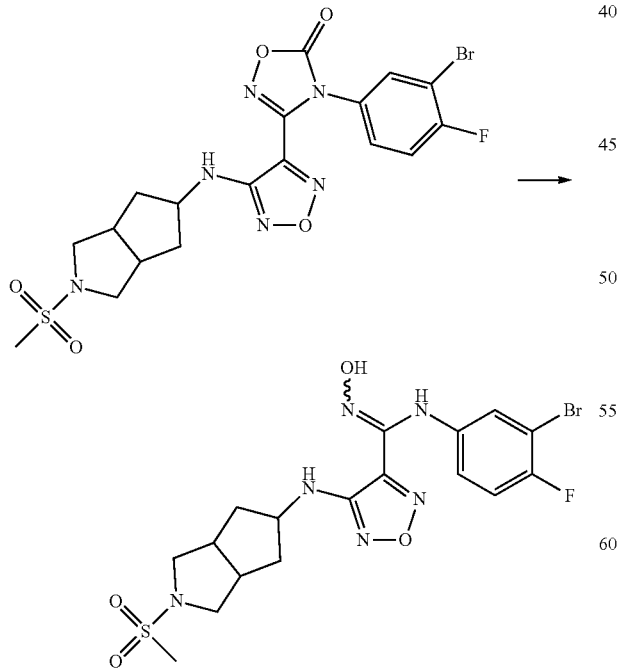

4-(3-bromo-4-fluorophenyl)-3-(4-((2-(methylsulfonypoctahydrocyclopenta[c]pyrrole-5-yl)amino)-1,2,5-oxadiazol-3-yl)-1,2,4-oxadiazol-5(4H)-one (250.7 mg, 0.47 mmol, 1.0 eq) was dissolved in THF (6.0 mL), added with sodium hydroxide solution (10%, 3 mL), and reacted with stirring for 30 min at room temperature. The reaction was monitored by TLC until it was complete. The reaction mixture was added with saturated ammonium chloride solution 15.0 mL, added with EA (8.0 mL×3) for extraction. The resulting organic phase was combined and washed with saturated brine (15.0 mL), and dried over anhydrous sodium sulfate, filtered, concentrated and precipitated to obtain a crude product, which was subjected to silica gel column chromatography (DCM:MeOH=200:1 to 100:1) to give N-(3-bromo-4-fluorophenyl)-N'-hydroxy-4-((2-(methylsulfonyl) octahydrocyclopenta[c]pyrrol-5-yl)amino)-1,2,5-oxadiazol-3-formamidine (65.7 mg, yield: 27.8%).

$^1$HNMR (400 MHz, DMSO-d$_6$) δ (ppm): 11.44 (s, 1H), 8.87 (s, 1H), 7.11-7.21 (m, 2H), 6.76-6.80 (m, 1H), 6.27 (d, 1H), 3.73-3.76 (m, 1H), 3.20-3.22 (m, 2H), 3.07-3.10 (m, 2H), 2.80 (s, 3H), 2.68 (m, 2H), 2.33-2.37 (m, 2H) 1.28-1.35 (m, 2H).

Molecular Formula: $C_{17}H_{20}BrFN_6O_4S$ Molecular weight: 503.35 LC-MS (Neg, m/z)=501.55 [M+H$^+$].

Example 7: Synthesis of N-(3-bromo-4-fluorophenyl)-N'-hydroxy-4-((2-sulfamidooctahydrocyclopenta[c]pyrrol-5-yl)amino)-1,2,5-oxadiazol-3-formamidine (Compound 9)

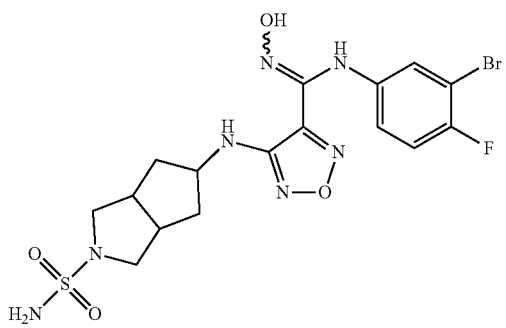 [SMILES: NS(=O)(=O)N1CC2CC(Nc3nonc3C(=NO)Nc3ccc(F)c(Br)c3)CC2C1]

Step 1: Synthesis of tert-butyl ((5-((4-(4-(3-bromo-4-fluorophenyl)-5-oxo-4,5-dihydro-1,2,4-oxadiazol-3-yl)-1,2,5-oxadiazol-3-yl)amino)hexahydrocyclopenta[c]pyrrole-2(1H)-yl)sulfonyl)carbamate

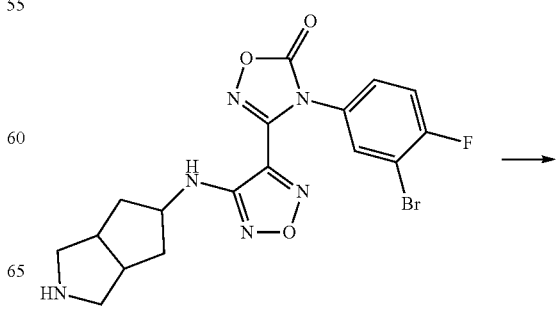

-continued

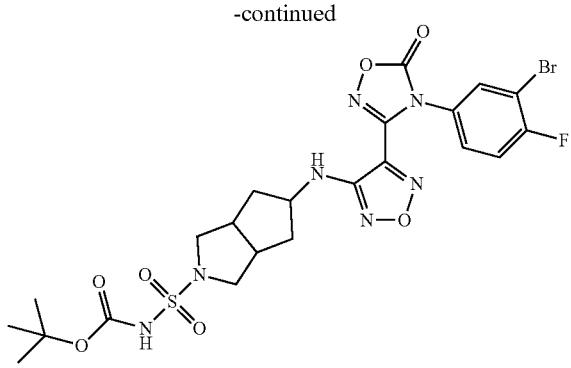

Sulfonyl chloride isocyanate (104.7 mg, 0.74 mmol, 1.2 eq) and tert-butanol (54.8 mg, 0.74 mmol, 1.2 eq) were dissolved in dichloromethane (8.0 mL), cooled to 0° C. in an ice bath, added with triethylamine (154.8 mg, 1.53 mmol, 3.0 eq), stirred at this temperature for 1.0 h, slowly added dropwise with 2.0 mL of 4-(3-bromo-4-fluorophenyl)-3-(4-((octahydrocyclopenta[c]pyrrole-5-yl)amino)-1,2,5-oxadiazol-3-yl)-1,2,4-oxadiazol-5(4H)-one (278.9 mg, 0.62 mmol, 1.0 eq) dissolved in dichloromethane, stirred at room temperature for 1.5 h. The reaction was monitored by TLC until it was complete. The reaction solution was added with saturated ammonium chloride solution (15.0 mL) and extract with ethyl acetate (8.0 mL×3). The organic phase was washed with saturated brine (15.0 mL), dried over anhydrous sodium sulfate, filtered and concentrated to give tert-butyl ((5-((4-(4-(3-bromo-4-fluorophenyl)-5-oxo-4,5-dihydro-1,2,4-oxadiazol-3-yl)-1,2,5-oxadiazol-3-yl)amino) hexahydrocyclopenta[c]pyrrole-2(1H)-yl)sulfonyl)carbamate (234.2 mg, yield: 59.9%).

Step 2: Synthesis of 5-((4-(4-(3-bromo-4-fluorophenyl)-5-oxo-4,5-dihydro-1,2,4-oxadiazol-3-yl)-1,2,5-oxadiazol-3-yl)amino)hexahydrocyclopenta[c]pyrrole-2(1H)-sulfamide

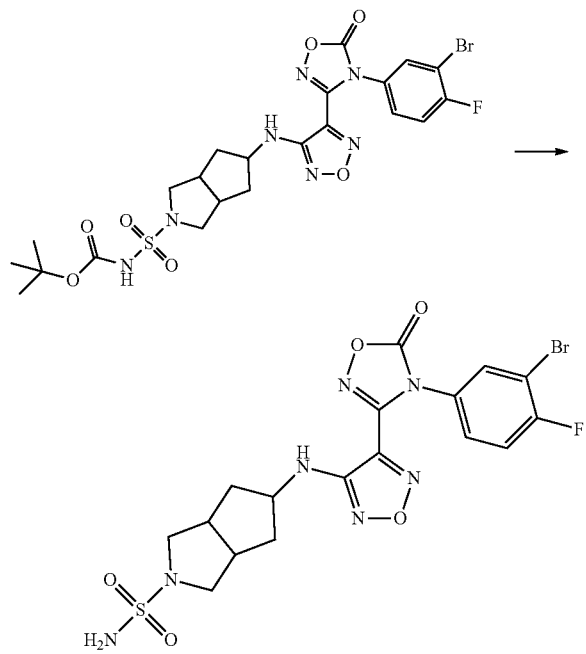

Tert-butyl 5-((4-(4-(3-bromo-4-fluorophenyl)-5-oxo-4,5-dihydro-1,2,4-oxadiazol-3-yl)-1,2,5-oxadiazol-3-yl)amino) hexahydrocyclopenta[c]pyrrole-2(1H)-carbamate (234.2 mg, 0.37 mmol, 1.0 eq) was dissolved in DCM (4.0 mL), added with trifluoroacetic acid (3.0 mL), and stirred at room temperature for 2.0 h. The reaction solution was monitored by TLC until it was complete. The reaction solution was concentrated to give crude 250.0 mg, yield 100%.

Step 3 Synthesis of N-(3-bromo-4-fluorophenyl)-N'-hydroxy-4-((2-(sulfinyloctahydrocyclopenta[c]pyrrole-5-yl)amino)-1,2,5-oxadiazol-3-formamidine

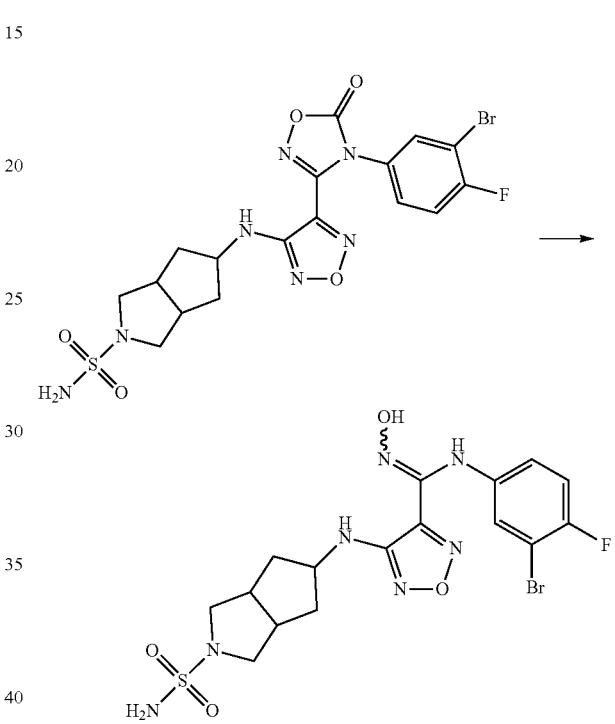

5-((4-(4-(3-bromo-4-fluorophenyl)-5-oxo-4,5-dihydro-1,2,4-oxadiazol-3-yl)-1,2,5-oxadiazol-3-yl)amino)hexahydrocyclopenta[c]pyrrole-2(1H)-sulfamide (250.0 mg, 0.47 mmol, 1.0 eq) was dissolved in THF (10.0 mL), added with sodium hydroxide solution (10%, 5 mL), and reacted with stirring for 40 min at room temperature. The reaction was monitored by TLC until it was complete. The reaction mixture was added with saturated ammonium chloride solution 20.0 mL, added with EA (8.0 mL×3) for extraction. The resulting organic phase was combined and washed with saturated brine (15.0 mL), and dried over anhydrous sodium sulfate, filtered, and concentrated to obtain a crude product, which was subjected to silica gel column chromatography (DCM:MeOH=200:1 to 100:1) to give N-(3-bromo-4-fluorophenyl)-N'-hydroxy-4-((2-(sulfamidooctahydrocyclopenta[c]pyrrole-5-yl)amino)-1,2,5-oxadiazol-3-formamidine (30.2 mg, yield: 12.7%).

¹HNMR (400 MHz, DMSO-$d_6$) δ (ppm): 11.44 (s, 1H), 8.87 (s, 1H), 7.11-7.21 (m, 2H), 6.76-6.80 (m, 1H), 6.27 (d, 1H), 3.73-3.76 (m, 1H), 3.20-3.22 (m, 2H), 2.67-2.69 (m, 2H), 2.33-2.37 (m, 2H), 1.24-1.30 (m, 2H).

Molecular Formula: $C_{16}H_{19}BrFN_7O_4S$ Molecular weight: 504.34 LC-MS (Neg, m/z)=502.67 [M+H⁺].

Example 8: Synthesis of 4-((2-oxaspiro[3.3]heptan-6-yl)amino)-N-(3-bromo-4-fluorophenyl)-N'-hydroxy-1,2,5-oxadiazol-3-carboxamidine (Compound 12)

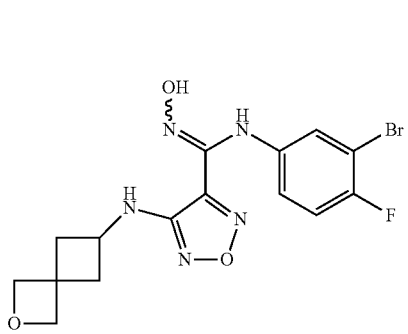 [SMILES: ON=C(Nc1ccc(F)c(Br)c1)c1nonc1NC1CC2(COC2)C1]

Step 1: Synthesis of 3-(4-((2-oxaspiro[3.3]heptan-6-yl)amino)-1,2,5-oxadiazol-3-yl)-4-(3-bromo-4-fluorophenyl)-1,2,4-oxadiazol-5(4H)-one

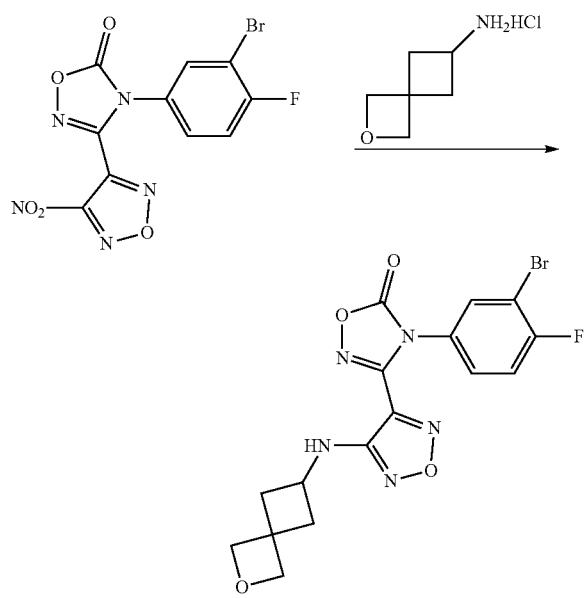

4-(3-bromo-4-fluorophenyl)-3-(4-nitro-1,2,5-oxadiazol-3-yl)-1,2,4-oxadiazol-5 (4H)-one (329.9 mg, 0.88 mmol, 1.0 eq) was dissolved in tetrahydrofuran (8 mL), added with triethylamine (538.3 mg, 5.32 mmol, 6.0 eq) and 2-oxaspiro[3.3] heptane-6-amine hydrochloride (265.3 mg, 1.77 mmol, 2.0 eq) at room temperature, then heated to 75° C. to reflux with stirring overnight. The reaction was monitored by TLC until it was complete. The reaction mixture was cooled and added with saturated ammonium chloride solution (50.0 mL), added with dichloromethane (150 mL×3) for extraction. The resulting organic phase was dried over anhydrous sodium sulfate, filtered, and concentrated to obtain a crude product, which was subjected to silica gel column chromatography (200-300 mesh silica gel; petroleum ether:ethyl acetate=10:1 to 8:1 to 6:1) to give 3-(4-((2-oxaspiro[3.3]heptan-6-yl)amino)-1,2,5-oxadiazol-3-yl)-4-(3-bromo-4-fluorophenyl)-1,2,4-oxadiazol-5(4H)-one (170.4 mg, yield: 44.1%).

Step 2: Synthesis of 4-((2-oxaspiro[3.3]heptan-6-yl)amino)-N-(3-bromo-4-fluorophenyl)-N'-hydroxy-1,2,5-oxadiazol-3-formamidine

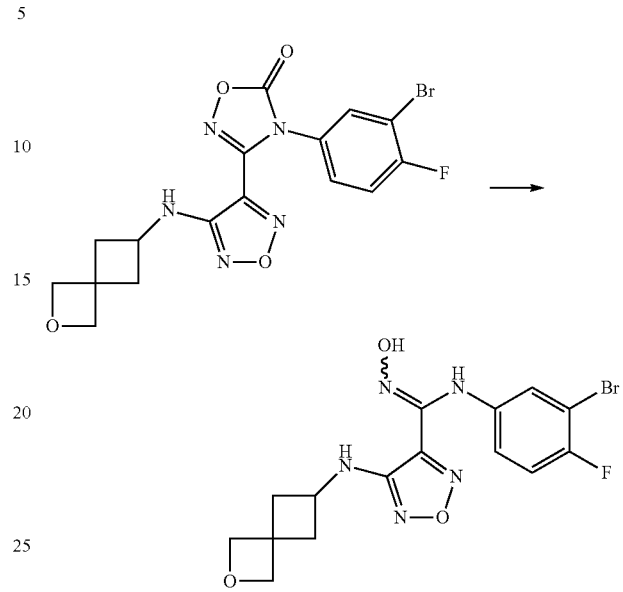

3-(4-((2-oxaspiro[3.3]heptan-6-yl)amino)-1,2,5-oxadiazol-3-yl)-4-(3-bromo-4-fluorophenyl)-1,2,4-oxadiazol-5 (4H)-one (169.4 mg, 0.38 mmol, 1.0 eq) was dissolved in tetrahydrofuran (4 mL), and 10% sodium hydroxide solution (2.5 mL) was added dropwise with stirring at room temperature and then stirred at room temperature for 1 hour. The reaction was monitored by TLC until it was complete. The reaction mixture was added with water (40 mL), extracted with dichloromethane (100 mL×3). The resulting organic phase was dried over anhydrous sodium sulfate to obtain a crude product, which was subjected to silica gel column chromatography (200-300 mesh silica gel; petroleum ether:ethyl acetate=10:1 to 1:1) to give 4-((2-oxaspiro[3.3]heptan-6-yl)amino)-N-(3-bromo-4-fluorophenyl)-N'-hydroxy-1,2,5-oxadiazol-3-formamidine (80.3 mg, yield: 51.2%).

$^1$HNMR (400 MHz, DMSO-$d_6$) δ (ppm): 11.40 (s, 1H), 8.80 (s, 1H), 7.11-7.19 (m, 2H), 6.74 (s, 1H), 6.35 (s, 1H), 4.48-4.59 (m, 4H), 3.76-3.78 (s, 1H), 2.49-2.60 (m, 2H), 2.11 (m, 2H).

Molecular Formula: $C_{15}H_{15}BrFN_5O_3$ Molecular weight: 412.22 LC-MS (Neg, m/z)=412.0 [M+H$^+$].

Example 9: Synthesis of N-(3-bromo-4-fluorophenyl)-4-((2,2-dioxo-2-thiaspiro[3.3]heptan-6-yl)amino)-N'-hydroxy-1,2,5-oxadiazol-3-formamidine (Compound 13)

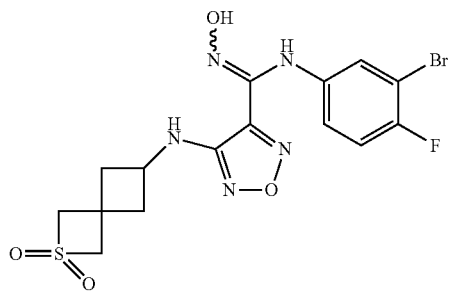 [SMILES: O=S1(=O)CC2(CC(Nc3nonc3C(=NO)Nc3ccc(F)c(Br)c3)C2)C1]

Step 1: Synthesis of 4-(3-bromo-4-fluorophenyl)-3-(4-((2,2-dioxo-2-thiaspiro[3.3]heptan-6-yl)amino)-1,2,5-oxadiazol-3-yl)-1,2,4-oxadiazol-5(4H)-one

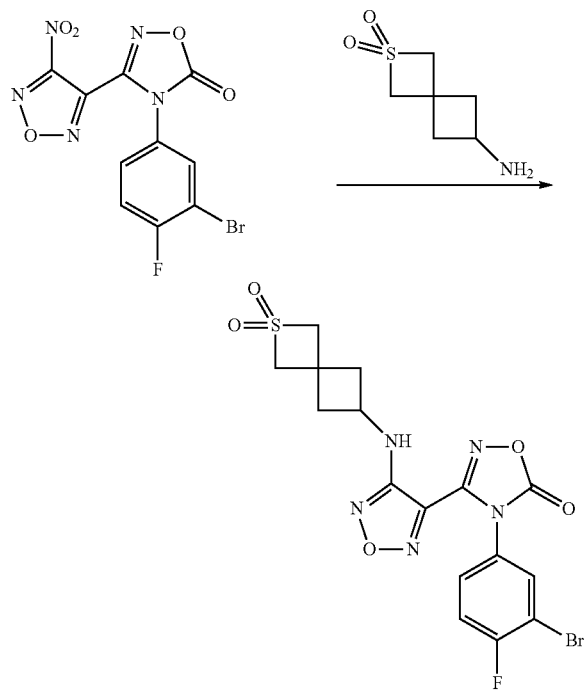

4-(3-bromo-4-fluorophenyl)-3-(4-nitro-1,2,5-oxadiazol-3-yl)-1,2,4-oxadiazol-5(4H)-one (200.0 mg, 0.54 mmol, 1.0 eq) was dissolved in THF (2 mL), added with 6-amino-2-thiaspiro[3.3]heptane-2,2-dioxide (174.1 mg, 1.08 mmol, 2.0 eq) and diisopropylethylamine (209.4 mg, 1.62 mmol, 3.0 eq), stirred at 0° C. for 2 hours. The reaction was monitored by TLC until it was complete. The resulting mixture was added with water (15 mL), and EA (3×20 mL) for extraction, and the resulting organic phase was combined. The resulting mixture was dried over anhydrous magnesium sulfate, filtered, concentrated to obtain a crude product, which was subjected to silica gel column chromatography (DCM:MeOH=200:1 to 100:1) to give 4-(3-bromo-4-fluorophenyl)-3-(4-((2,2-dioxo-2-thiaspiro[3.3]heptan-6-yl)amino)-1,2,5-oxadiazol-3-yl)-1,2,4-oxadiazol-5(4H)-one (240.0 mg, yield: 92.3%).

Step 2: Synthesis of N-(3-bromo-4-fluorophenyl)-4-((2,2-dioxo-2-thiaspiro[3.3]heptan-6-yl)amino)-N'-hydroxy-1,2,5-oxadiazol-3-formamidine

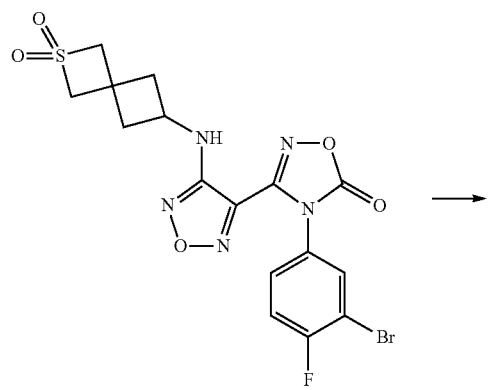

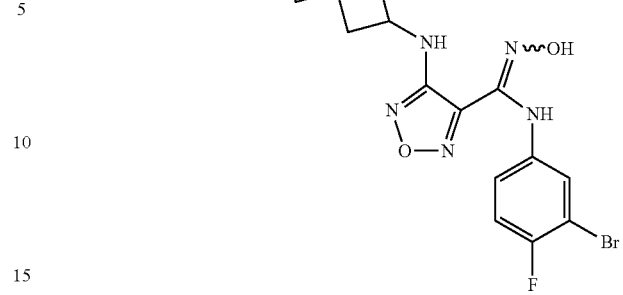

4-(3-bromo-4-fluorophenyl)-3-(4-((2,2-dioxo-2-thiaspiro[3.3]heptan-6-yl)amino)-1,2,5-oxadiazol-3-yl)-1,2,4-oxadiazol-5(4H)-one (230.0 mg, 0.47 mmol) was dissolved in THF (2 mL), added with sodium hydroxide aqueous solution (10%) (3 mL), and reacted with stirring for 40 min at room temperature. The reaction was monitored by TLC until it was complete. The reaction mixture was added with water, and extracted with EA (20 mL×3), and the resulting organic phase was separated and combined. The resulting mixture was dried over anhydrous sodium sulfate, filtered, the filtrate was concentrated to obtain a crude product, which was subjected to silica gel column chromatography (eluent: DCM:MeOH=200:1, 100:1, 80:1) to give N-(3-bromo-4-fluorophenyl)-4-((2,2-dioxo-2-thiaspiro[3.3]heptan-6-yl)amino)-N'-hydroxy-1,2,5-oxadiazol-3-formamidine (110.0 mg, yield: 50.8%).

$^1$HNMR (400 MHz, DMSO-d$_6$) δ (ppm): 11.42 (s, 1H), 8.90 (s, 1H), 7.12-7.21 (t, 1H), 7.10-7.12 (t, 1H), 6.74-6.77 (m, 1H), 6.47-6.49 (d, 1H), 4.01-4.29 (m, 4H), 3.91-3.97 (m, 1H), 2.65-2.69 (m, 2H) 2.30-2.50 (m, 2H).

Molecular Formula: C$_{15}$H$_{15}$BrFN$_5$O$_4$S, Molecular weight: 460.28, LC-MS (Pos, m/z)=460.0 [M+H$^+$].

Example 10: Synthesis of N-(3-bromo-4-fluorophenyl)-N'-hydroxy-4-((tetrahydrofuran-3-yl)amino)-1,2,5-oxadiazol-3-formamidine (Compound 14)

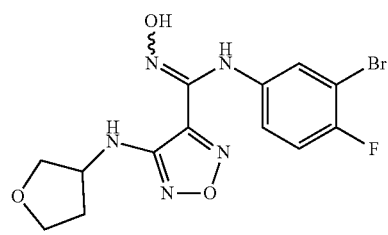 [SMILES: ON=C(Nc1ccc(F)c(Br)c1)c1nonc1NC1CCOC1]

Step 1: Synthesis of 4-(3-bromo-4-fluorophenyl)-3-(4-(tetrahydrofuran-3-yl)amino)-1,2,5-oxadiazole-3-yl)-1,2,4-oxadiazol-5(4H)-one

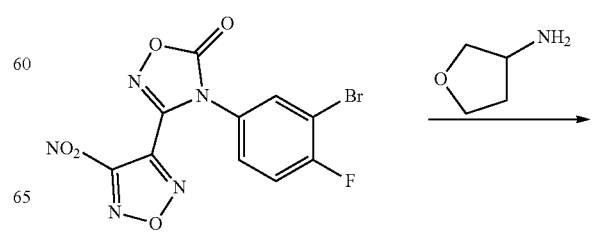

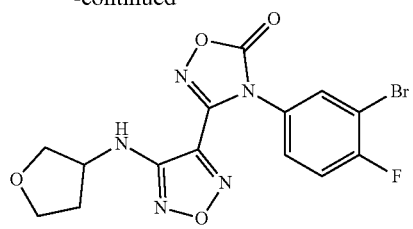

4-(3-bromo-4-fluorophenyl)-3-(4-nitro-1,2,5-oxadiazol-3-yl)-1,2,4-oxadiazol-5(4H)-one (213.9 mg, 0.58 mmol, 1.0 eq) was dissolved in THF (2.0 mL), adding tetrahydrofuran-3-amine (100.0 mg, 1.15 mmol, 2.0 eq) and triethylamine (314.2 mg, 3.1 mmol, 5.4 eq), refluxing at 75° C. overnight. The reaction was monitored by TLC until it was complete. Water (8 mL) and ethyl acetate (4 mL) were added to the reaction solution. The aqueous phase was separated and extracted with EA (2×4.0 mL). The resulting organic phase was separated, combined and washed with saturated brine (10.0 mL). The resulting mixture was dried over anhydrous sodium sulfate, filtered, concentrated to obtain a crude product, which was subjected to silica gel column chromatography (PE:EA=10:1) to give 4-(3-bromo-4-fluorophenyl)-3-(4-(tetrahydrofuran-3-yl)amino)-1,2,5-oxadiazol-3-yl)-1,2,4-oxadiazol-5(4H)-one (102.0 mg, yield: 42.7%).

Step 2: Synthesis of N-(3-bromo-4-fluorophenyl)-N'-hydroxy-4-((tetrahydrofuran-3-yl)amino)-1,2,5-oxadiazol-3-formamidine

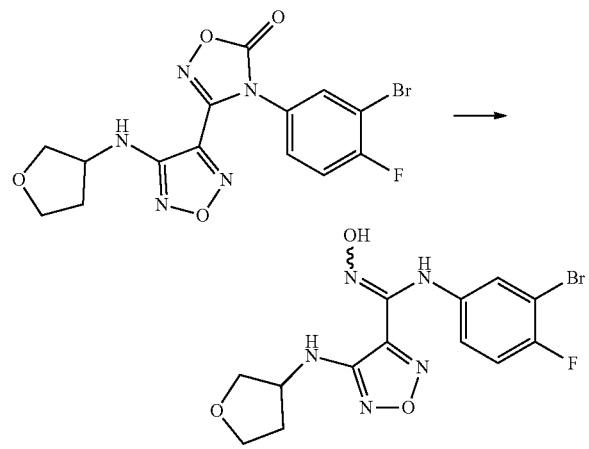

4-(3-bromo-4-fluorophenyl)-3-(4-(tetrahydrofuran-3-yl) amino)-1,2,5-oxadiazol-3-yl)-1,2,4-oxadiazol-5(4H)-one (102.0 mg, 0.24 mmol, 1.0 eq) was dissolved in THF (3.0 mL), added with sodium hydroxide solution (10%, 1.5 mL), and reacted with stirring for 30 min at room temperature. The reaction was monitored by TLC until it was complete. The reaction mixture was added with saturated ammonium chloride solution 10.0 mL, added with EA (4 mL×3) for extraction. The resulting organic phase was combined and washed with saturated brine (10.0 mL), and dried over anhydrous sodium sulfate, filtered, and concentrated to obtain a crude product, which was subjected to silica gel column chromatography (DCM:MeOH=200:1 to 100:1) to give N-(3-bromo-4-fluorophenyl)-N'-hydroxy-4-((tetrahydrofuran-3-yl)amino)-1,2,5-oxadiazol-3-formamidine (29.6 mg, yield: 32.0%).

$^1$HNMR (400 MHz, DMSO-d$_6$) δ (ppm): 11.48 (s, 1H), 8.88 (s, 1H), 6.80-7.18 (m, 2H), 6.77 (m, 1H), 6.30 (d, 1H), 4.04-4.10 (m, 1H), 3.80 (m, 2H) 3.73 (m, 1H), 3.60 (m, 1H), 2.22 (m, 1H), 1.87 (m, 1H).

Molecular Formula: C$_{13}$H$_{13}$BrFN$_5$O$_3$ Molecular weight 386.18 LC-MS (Neg, m/z)=384.51 [M+H$^+$].

Example 11: Synthesis of N-(3-bromo-4-fluorophenyl)-4-((1,1-dioxo-tetrahydrothiophen-3-yl)amino)-N'-hydroxy-1,2,5-oxadiazol-3-formamidine (Compound 15)

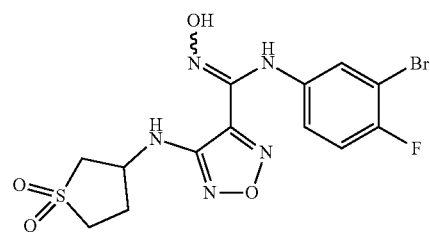 [SMILES: O=S1(=O)CCC(Nc2nonc2C(=NO)Nc2ccc(F)c(Br)c2)C1]

Step 1: Synthesis of 4-(3-bromo-4-fluorophenyl)-3-(4-((1,1-dioxo-tetrahydrothiophen-3-yl)amino)-1,2,5-oxadiazole-3-yl)-1,2,4-oxadiazol-5(4H)-one

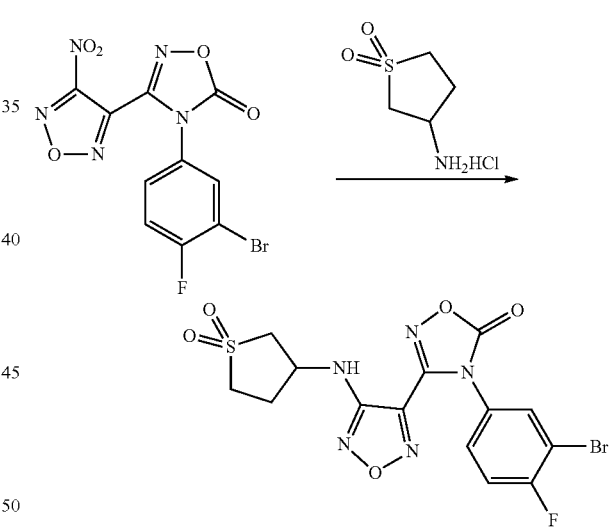

4-(3-bromo-4-fluorophenyl)-3-(4-nitro-1,2,5-oxadiazol-3-yl)-1,2,4-oxadiazol-5(4H)-one (300.0 mg, 0.81 mmol, 1.0 eq) was dissolved in DMA (4 mL), and added with 3-aminotetrahydrothiophene-1,1-dioxide hydrochloride (276.7 mg, 1.61 mmol, 2.0 eq), reacted with stirring for 1 h in an ice-bath. The reaction was monitored by TLC until it was complete. The resulting mixture was added with water (30 mL), and EA (3×30 mL) for extraction, and the resulting organic phase was combined. The resulting mixture was dried over anhydrous magnesium sulfate, filtered, concentrated to obtain a crude product, which was subjected to silica gel column chromatography (PE:EA=10:1 to 1:1) to give 4-(3-bromo-4-fluorophenyl)-3-(4-((1,1-dioxo-tetrahydrothiophen-3-yl)amino)-1,2,5-oxadiazol-3-yl)-1,2,4-oxadiazol-5(4H)one (165.1 mg, yield: 44.6%).

Step 2: Synthesis of N-(3-bromo-4-fluorophenyl)-4-((1,1-dioxo-tetrahydrothiophen-3-yl)amino)-N'-hydroxy-1,2,5-oxadiazol-3-formamidine

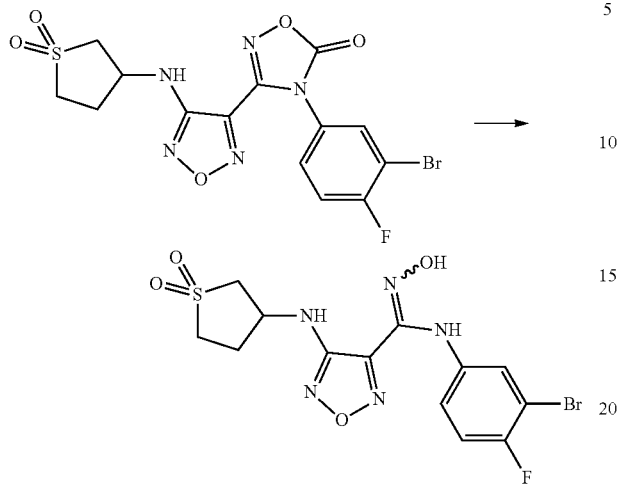

4-(3-bromo-4-fluorophenyl)-3-(4-((1,1-dioxo-tetrahydrothiophen-3-yl)amino)-1,2,5-oxadiazol-3-yl)-1,2,4-oxadiazol-5(4H)one (165.1 mg, 0.36 mmol, 1.0 eq) was dissolved in THF (15 mL), added with sodium hydroxide solution (2 mol/L, 2 mL), and reacted with stirring for 30 min. The reaction was monitored by TLC until it was complete. The solution was adjusted to a pH of 2-3 with 1 mol/L hydrochloric acid solution, added with EA (3×20 mL) for extraction, and the resulting organic phase was combined. The resulting mixture was dried over anhydrous magnesium sulfate, filtered, concentrated to obtain a crude product, which was subjected to silica gel column chromatography (PE:EA=10:1 to 1:1) to give N-(3-bromo-4-fluorophenyl)-4-((1,1-dioxo-tetrahydrothiophen-3-yl)amino)-N'-hydroxy-1,2,5-oxadiazol-3-formamidine (48.5 mg, yield: 31%).

$^1$HNMR (400 MHz, DMSO-$d_6$) δ (ppm): 11.48 (s, 1H), 8.93 (s, 1H), 7.11-7.20 (m, 2H), 6.75-6.78 (m, 1H), 6.63-6.65 (m, 1H), 4.29-4.34 (m, 1H), 3.51-3.53 (m, 1H), 3.48-3.49 (m, 1H), 2.20 (3, 3H), 3.21-3.31-2.05 (m, 1H), 3.07-3.19 (m, 1H), 2.45-2.50 (m, 1H), 2.17-2.19 (m, 1H).

Molecular Formula: $C_{13}H_{13}BrFN_5O_4S$ Molecular weight: 434.24 LC-MS (m/z)=434.0 [M–H$^+$].

Compound 15 of N-(3-bromo-4-fluorophenyl)-4-((1,1-dioxo-tetrahydrothiophen-3-yl)amino)-N'-hydroxy-1,2,5-oxadiazol-3-formamidine (30 mg) was subjected to resolution by a chiral HPLC column. The fraction at the first peak was collected and lyophilized to give a white solid (8.3 mg, ee value 100%), hereinafter referred to as 15-P1. The fraction at the second peak was collected and lyophilized to give a white solid (9.66 mg, ee value 99.7%), hereinafter referred to as 15-P2. The structures of 15-P1 and 15-P2 independently correspond to compounds 24 and 25.

(Compound 24)

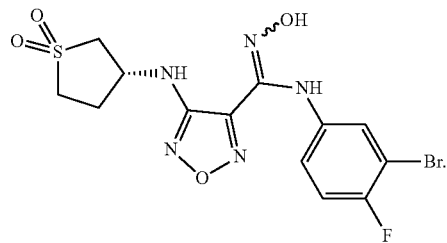

and (Compound 25)

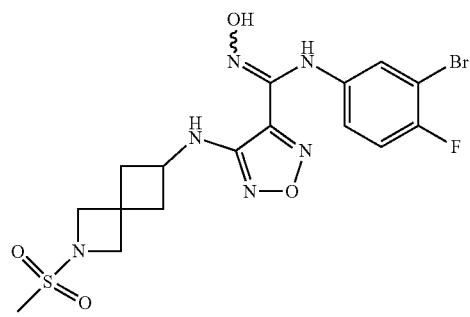 [SMILES: CS(=O)(=O)N1CC2(CC(Nc3nonc3C(=NO)Nc3ccc(F)c(Br)c3)C2)C1]

Example 12: Synthesis of N-(3-bromo-4-fluorophenyl)-N'-hydroxy-4-((2-(methylsulfonyl)-2-azaspiro[3.3]heptan-6-yl)amino)-1,2,5-oxadiazol-3-formamidine (Compound 16)

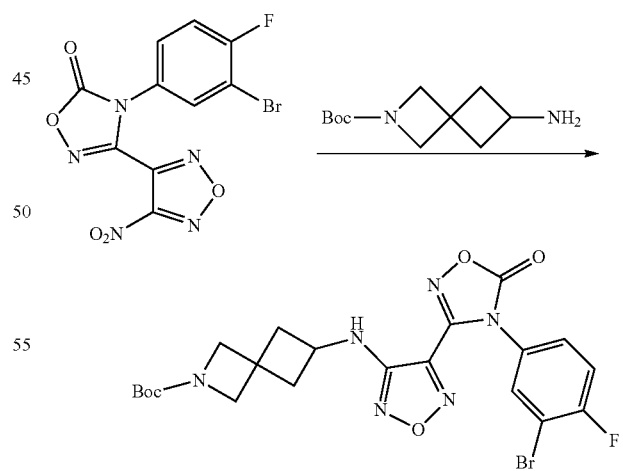

Step 1: Synthesis of tert-butyl 6-((4-(4-(3-bromo-4-fluorophenyl)-5-oxo-4,5-dihydro-1,2,4-oxadiazol-3-yl)-1,2,5-oxadiazol-3-yl)amino)-2-azaspiro[3.3]heptan-2-carboxylate 4-(3-bromo-4-fluorophenyl)-3-(4-nitro-1,2,5-oxadiazol-3-yl)-1,2,4-oxadiazol-5(4H)-one (372 mg, 1 mmol, 1.0 eq) and tert-butyl 6-amino-2-azaspiro[3.3]heptan-2-carboxylate (448 mg, 2.11 mmol, 2.0 eq) were dissolved in THF (20 mL), triethylamine (303 mg, 3 mmol. 3.0 eq) was added and the mixture was warmed to 75° C. to react for 2 h. The reaction was monitored by TLC (PE:EA=2:1) until it was complete. The reaction was stopped by adding water (50 mL), and the mixture was extracted with EA (50 mL×2). The resulting organic phase was combined, dried over anhydrous sodium sulfate, filtered and concentrated to obtain a crude product, which was subjected to silica gel column chromatography (PE:EA=10:1 to 2:1) to give the target compound (500 mg, yield: 93%).

Step 2: Synthesis of 3-(4-((2-azaspiro[3.3]heptan-6-yl)amino)-1,2,5-oxodiazol-3-yl)-4-(3-bromo-4-fluorophenyl)-1,2,4-oxadiazol-5(4H)-one

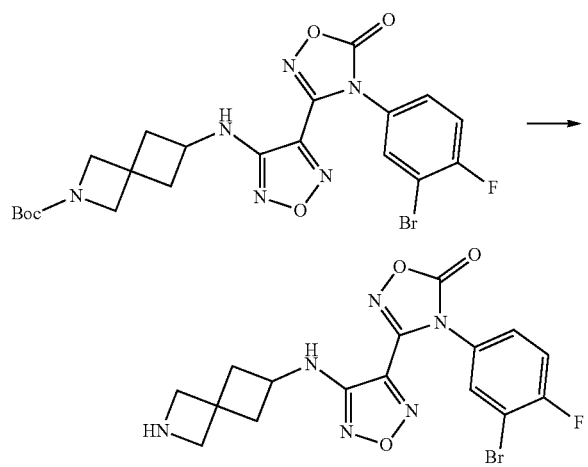

Tert-butyl 6-((4-(4-(3-bromo-4-fluorophenyl)-5-oxo-4,5-dihydro-1,2,4-oxadiazol-3-yl)-1,2,5-oxadiazol-3-yl)amino)-2-azaspiro[3.3]heptan-2-carboxylate (500 mg, 0.93 mmol) was dissolved in DCM (10 mL), added with TFA (2 mL), reacted with stirring at room temperature for 2 h. The reaction was monitored by TLC (DCM:MeOH=10:1) until it was complete. The reaction solution was concentrated directly, and dissolved into DCM (50 mL). The dissolved mixture was concentrated under vacuum. The steps were repeated twice to give the target compound (790 mg crude, yield 100%).

Step 3: Synthesis of 4-(3-bromo-4-fluorophenyl)-3-(4-((2-(methylsulfonyl)-2-azaspiro[3.3]heptan-6-yl)amino)-1,2,5-oxadiazol-3-yl)-1,2,4-oxadiazol-5(4H)-one

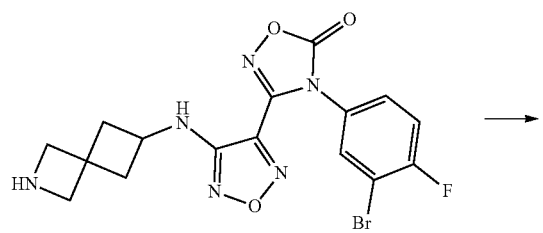

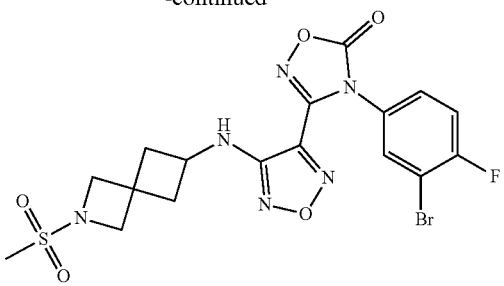

3-(4-((2-azaspiro[3.3]heptan-6-yl)amino)-1,2,5-oxadiazol-3-yl)-4-(3-bromo-4-fluorophenyl)-1,2,4-oxadiazol-5(4H)-one (200 mg, crude) was dissolved in DCM (5 mL), added with triethylamine (162 mg, 0.16 mmol). Methanesulfonyl chloride (71 mg, 0.532 mmol) was added slowly and stirred at room temperature for two hours. The reaction was monitored by TLC (DCM:MeOH=10:1) until the raw material was completely reacted. The mixture was concentrated to obtain a crude, which was subjected to silica gel column chromatography (DCM:MeOH=10:1) to give a product (90 mg, yield: 74.2%).

Step 4: Synthesis of N-(3-bromo-4-fluorophenyl)-N'-hydroxy-4-((2-(methylsulfonyl)-2-azaspiro[3.3]heptan-6-yl)amino)-1,2,5-oxadiazol-3-formamidine

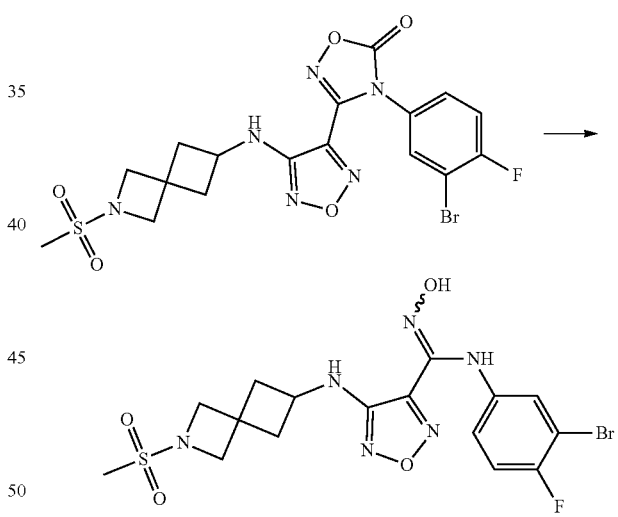

4-(3-bromo-4-fluorophenyl)-3-(4-((2-(methylsulfonyl)-2-azaspiro[3.3]heptan-6-yl)amino)-1,2,5-oxadiazol-3-yl)-1,2,4-oxadiazol-5(4H)-one (90 mg, 0.175 mmol, 1.0 eq) was dissolved in THF (2 mL), added with NaOH aqueous solution (2 mol/L, 0.5 mL) to react for 2 hours at room temperature. The reaction was monitored by TLC (DCM:MeOH=10:1) until the raw material was completely reacted. The reaction mixture was poured into water (10 mL), and extracted with DCM (30 mL×3). The resulting organic phase was combined, filtered, concentrated and dried to give a crude product (80 mg), which was added with DCM (3 mL) and slurried for 1 hour. The resulting mixture was filtered and dried to give N-(3-bromo-4-fluorophenyl)-N'-hydroxy-4-((2-(methylsulfonyl)-2-azaspiro[3.3]heptan-6-yl)amino)-1,2,5-oxadiazol-3-formamidine (53 mg, yield: 62%).

¹HNMR (400 MHz, DMSO-d₆) δ (ppm): 11.42 (s, 1H), 8.89 (s, 1H), 7.10-7.21 (m, 1H), 6.74-6.78 (m, 2H), 6.39-6.41 (m, 1H), 3.92 (s, 2H), 3.83-3.89 (m, 1H), 3.81 (s, 2H), 2.96 (s, 3H), 2.16-2.56 (m, 2H), 2.13-2.15 (m, 2H).

Molecular Formula: $C_{16}H_{18}BrFN_6O_4S$ Molecular weight: 488.03 LC-MS (Pos, m/z)=489.0 [M+H⁺].

Example 13: Synthesis of N-(3-bromo-4-fluorophenyl)-N'-hydroxy-4-((2-sulfamoyl-2-azaspiro[3.3]heptan-6-yl)amino)-1,2,5-oxadiazol-3-formamidine (Compound 17)

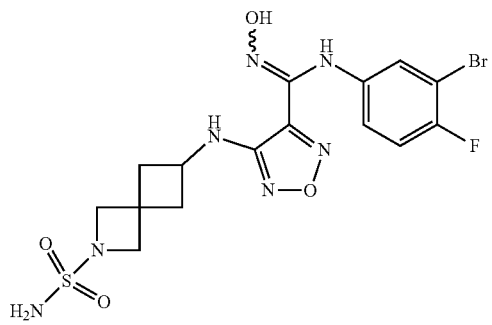 [SMILES: NS(=O)(=O)N1CC2(CC(Nc3nonc3C(=NO)Nc3ccc(F)c(Br)c3)C2)C1]

Step 1: Synthesis of tert-butyl ((6-((4-(4-(3-bromo-4-fluorophenyl)-5-oxo-4,5-dihydro-1,2,4-oxadiazol-3-yl)-1,2,5-oxadiazol-3-yl)amino)-2-azaspiro[3.3]heptan-2-yl)sulfonyl)carbamate

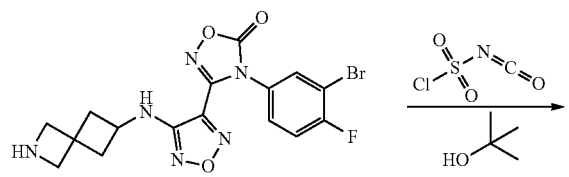

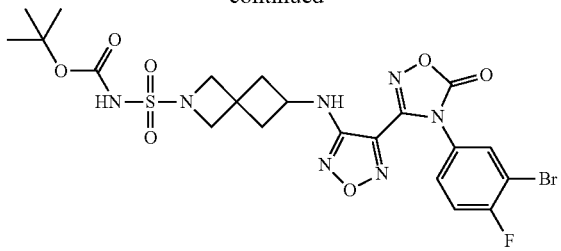

Tert-butanol (45 mg, 0.6 mmol, 1.2 eq) was dissolved in DCM (10 mL), cooled to 0° C., chlorosulfonyl isocyanate (77.8 mg, 0.55 mmol, 1.1 eq) was added dropwise, and reacted at 0° C. for 1.5 hours. The reaction solution (1.15 mL) was slowly added dropwise to a mixture of 3-(4-((2-azaspiro[3.3]heptan-6-yl)amino)-1,2,5-oxodiazol-3-yl)-4-(3-bromo-4-fluorophenyl)-1,2,4-oxadiazol-5(4H)-one (obtained in Step 2 for preparing compound 16, 218 mg, 0.50 mmol, 1.0 eq), TEA (125 mg, 1.5 mmol, 3 eq) and DCM (5 mL), previously cooled to below 0° C. The resulting mixture was stirred for 2 hours below 0° C. for reaction. The reaction was monitored by TLC until it was complete. The reaction mixture was added with water with stirring, DCM (20 mL×3) for extraction. The organic phase was separated, combined, dried over anhydrous magnesium sulfate, and filtered, the filtrate was concentrated to obtain a crude product, which was subjected to silica gel column chromatography (eluent: DCM:MeOH=10:1) to give tert-butyl 6-((4-(4-(3-bromo-4-fluorophenyl)-5-oxo-4,5-dihydro-1,2,4-oxadiazol-3-yl)-1,2,5-oxadiazol-3-yl)amino)-2-azaspiro[3.3]heptan-2-yl)sulfonyl)carbamate (120 mg, yield: 38.9%).

Step 2: Synthesis of 6-((4-(4-(3-bromo-4-fluorophenyl)-5-oxo-4,5-dihydro-1,2,4-oxadiazol-3-yl)-1,2,5-oxadiazol-3-yl)amino)-2-azaspiro[3.3]heptan-2-sulfonamide

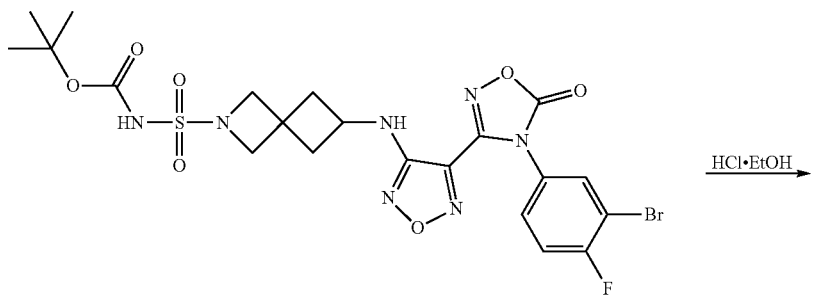

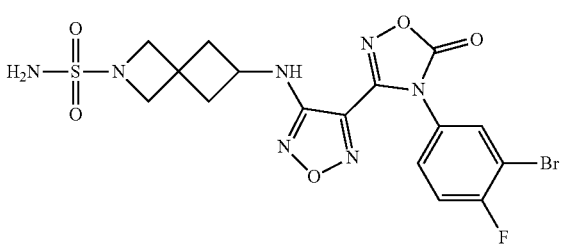

Tert-butyl 6-((4-(4-(3-bromo-4-fluorophenyl)-5-oxo-4,5-dihydro-1,2,4-oxadiazol-3-yl)-1,2,5-oxadiazol-3-yl)amino)-2-azaspiro[3.3]heptan-2-yl)sulfonyl)carbamate (100 mg) was dissolved in DCM (2 mL), added with TFA (0.5 mL) to react at room temperature for 30 min. The reaction was monitored by TLC until it was complete. The reaction solution was concentrated under reduced pressure to dryness to give 6-((4-(4-(3-bromo-4-fluorophenyl)-5-oxo-4,5-dihydro-1,2,4-oxadiazol-3-yl)-1,2,5-oxadiazol-3-yl)amino)-2-azaspiro[3.3]heptan-2-sulfonamide (120 mg crude, yield: 100%), which was directly used in the next step without purification.

Step 3 Synthesis of N-(3-bromo-4-fluorophenyl)-N'-hydroxy-4-((2-sulfamoyl-2-azaspiro[3.3]heptan-6-yl)amino)-1,2,5-oxadiazol-3-formamidine

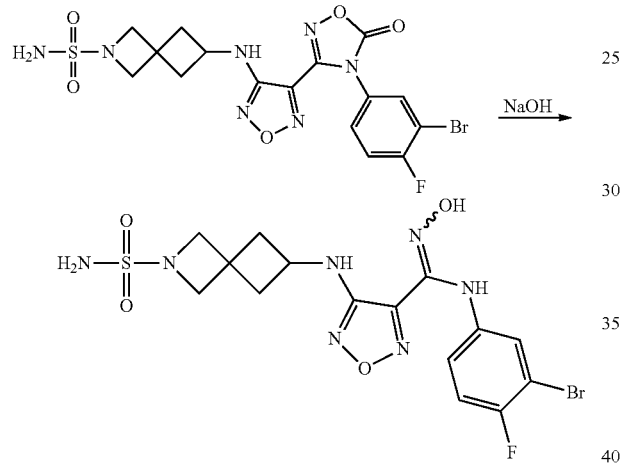

6-((4-(4-(3-bromo-4-fluorophenyl)-5-oxo-4,5-dihydro-1,2,4-oxadiazol-3-yl)-1,2,5-oxadiazol-3-yl)amino)-2-azaspiro[3.3]heptan-2-sulfonamide (120 mg, crude) was dissolved in THF (2 mL), added with NaOH aqueous solution (2 mmol/L, 0.5 mL), and reacted at room temperature for 2 h. The reaction was monitored by TLC (DCM:MeOH=10:1) until the raw material was completely reacted. The reaction solution was poured into water (10 mL), and extracted with DCM (30 mL×3). The resulting organic phase was combined, dried over anhydrous sodium sulfate, filtered, and concentrated to give a crude, which was subjected to silica gel column chromatography (DCM:MeOH=10:1) and purified to give N-(3-bromo-4-fluorophenyl)-N'-hydroxy-4-((2-(sulfamoyl)-2-azaspiro[3.3]heptan-6-yl)amino)-1,2,5-oxadiazol-3-formamidine (25 mg, yield for three steps: 31.4%).

$^1$HNMR (400 MHz, DMSO-$d_6$) δ (ppm) 7.79 (s, 1H), 7.24-7.60 (m, 2H), 6.80-6.83 (m, 1H), 6.58 (s, 2H), 3.81-4.13 (m, 4H), 3.06 (s, 3H) 2.33-2.36 (m, 2H), 1.87-1.89 (dd, 2H).

Molecular Formula: $C_{15}H_{17}BrFN_7O_4S$ Molecular weight: 489.02 LC-MS (Pos, m/z)=489.9 [M+H$^+$].

Example 14: Synthesis of N-(3-bromo-4-fluorophenyl)-N'-hydroxy-4-((2-sulfamoyl-2-azabicyclo[2.2.1]heptan-5-yl)amino)-1,2,5-oxadiazol-3-formamidine (Compound 18)

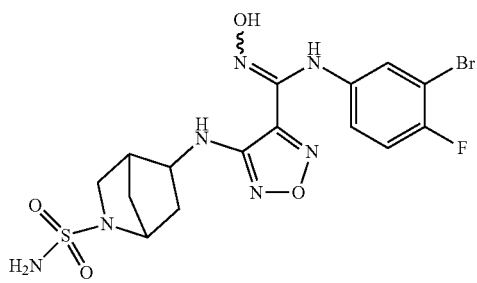 [SMILES: NS(=O)(=O)N1CC2CC1CC2Nc1nonc1C(=NO)Nc1ccc(F)c(Br)c1]

Step 1: Synthesis of tert-butyl 5-((4-(4-(3-bromo-4-fluorophenyl)-5-oxo-4,5-dihydro-1,2,4-oxadiazol-3-yl)-1,2,5-oxadiazol-3-yl)amino)-2-azabicyclo[2.2.1]heptan-2-carboxylate

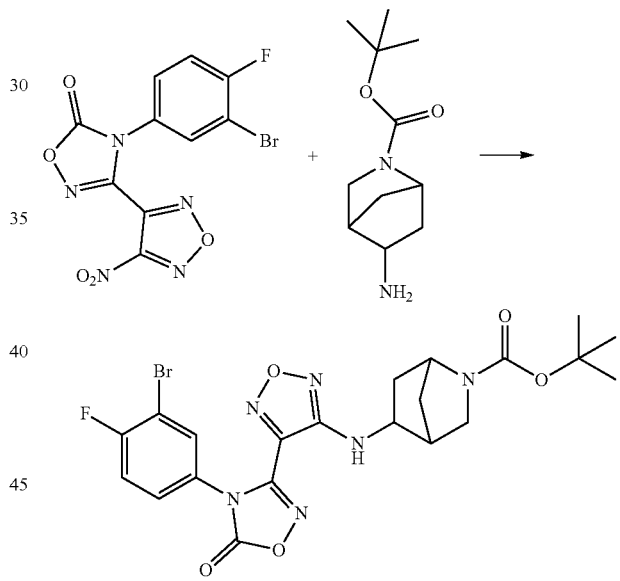

4-(3-bromo-4-fluorophenyl)-3-(4-nitro-1,2,5-oxadiazol-3-yl)-1,2,4-oxadiazol-5(4H)-one (701 mg, 1.884 mmol, 1.0 eq) was dissolved in THF (45 mL), added with tert-butyl 5-amino-2-azabicyclo[2.2.1]heptan-2-carboxylate (780 mg, 3.67 mmol, 2 eq), and TEA (1029 mg, 10.174 mmol, 5.4 eq) was added, and the reaction was heated at 70° C. for 2 h. The reaction was monitored by TLC until it was complete. The reaction solution was cooled to room temperature, adjusted to pH=2 with 1 mol/L hydrochloric acid, and extracted with EA (20 mL×3). The organic phase was separated, combined, dried over anhydrous sodium sulfate, and subjected to suction filtration. The filtrate was concentrated, and subjected to column chromatography (eluent: DCM:MeOH=100:1) to give tert-butyl 5-((4-(4-(3-bromo-4-fluorophenyl)-5-oxo-4,5-dihydro-1,2,4-oxadiazol-3-yl)-1,2,5-oxadiazol-3-yl)amino)-2-azabicyclo[2.2.1]heptan-2-carboxylate (crude, 1072 mg).

Step 2: Synthesis of 3-(4-((2-azabicyclo[2.2.1]heptan-5-yl)amino)-1,2,5-oxadiazol-3-yl)-4-(3-bromo-4-fluorophenyl)-1,2,4-oxadiazol-5 (4H)-one

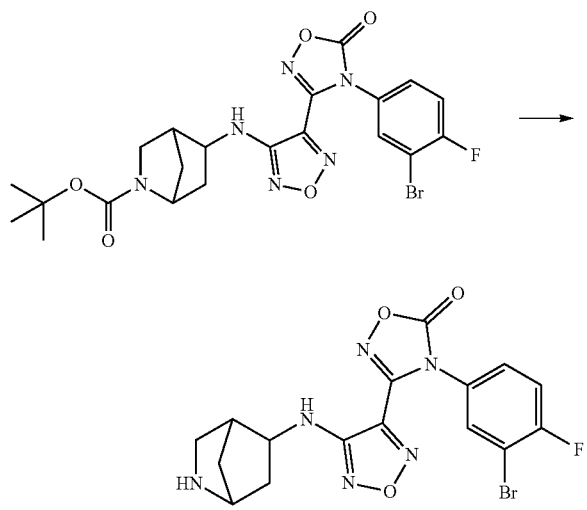

Tert-butyl 5-((4-(4-(3-bromo-4-fluorophenyl)-5-oxo-4,5-dihydro-1,2,4-oxadiazol-3-yl)-1,2,5-oxadiazol-3-yl)amino)-2-azabicyclo[2.2.1]heptan-2-carboxylate (1072 mg, crude) was dissolved in THF (10 mL), cooled to 0° C., added with trifluoroacetic acid (3.5 mL), and warmed to room temperature to react for 30 min. The reaction was monitored by TLC until it was complete. The reaction solution was concentrated under reduced pressure to dryness to give 3-(4-((2-azabicyclo[2.2.1]heptan-5-yl)amino)-1,2,5-oxadiazol-3-yl)-4-(3-bromo-4-fluorophenyl)-1,2,4-oxadiazol-5(4H)-one (872 mg), which was directly used in the next step.

Step 3: Synthesis of tert-butyl ((5-((4-(4-(3-bromo-4-fluorophenyl)-5-oxo-4,5-dihydro-1,2,4-oxadiazol-3-yl)-1,2,5-oxadiazol-3-yl)amino)-2-azabicyclo[2.2.1]heptan-2-yl)sulfonyl)carbamate

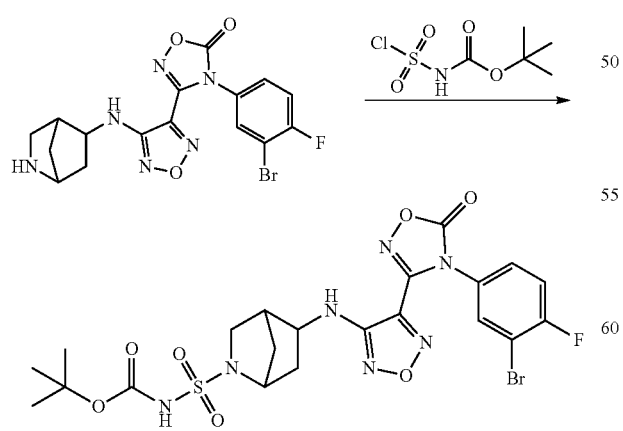

Tert-butanol (1.02 g, 118.0 mmol, 1.2 eq) was dissolved in DCM (10 mL), cooled to 0° C., chlorosulfonyl isocyanate (1.87 g) was added dropwise, and reacted at 0° C. for 1.5 hours. The reaction solution (1.15 mL) was slowly added dropwise to a mixture of intermediate 3-(4-((2-azabicyclo[2.2.1]heptan-5-yl)amino)-1,2,5-oxodiazol-3-yl)-4-(3-bromo-4-fluorophenyl)-1,2,4-oxadiazol-5(4H)-one (580 mg, 1.327 mmol, 1.0 eq), TEA (671.4 mg, 5 eq) and DCM (5 mL), previously cooled to below 0° C. The resulting mixture was stirred for 1 hour below 0° C. for reaction. The reaction was monitored by TLC until it was complete. The reaction mixture was added with water (20 mL) with stirring, DCM (20 mL×3) for extraction. The organic phase was separated, combined, dried over anhydrous magnesium sulfate, and filtered, the filtrate was concentrated to obtain a crude product, which was subjected to silica gel column chromatography (eluent: DCM:MeOH=100:1) to give tert-butyl ((5-((4-(4-(3-bromo-4-fluorophenyl)-5-oxo-4,5-dihydro-1,2,4-oxadiazol-3-yl)-1,2,5-oxadiazol-3-yl)amino)-2-azabicyclo[2.2.1]heptan-2-yl)sulfonyl)carbamate (621 mg, yield: 75.9%).

Step 4: Synthesis of 5-((4-(4-(3-bromo-4-fluorophenyl)-5-oxo-4,5-dihydro-1,2,4-oxadiazol-3-yl)-1,2,5-oxadiazol-3-yl)amino)-2-azabicyclo[2.2.1]heptan-2-sulfonamide

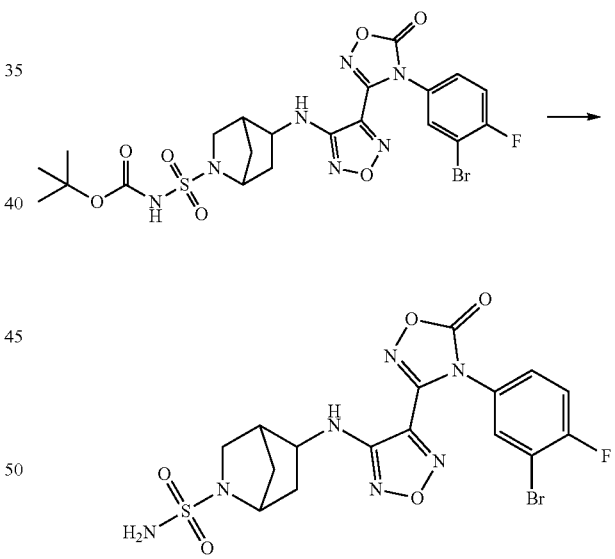

Tert-butyl ((5-((4-(4-(3-bromo-4-fluorophenyl)-5-oxo-4,5-dihydro-1,2,4-oxadiazol-3-yl)-1,2,5-oxadiazol-3-yl)amino)-2-azabicyclo[2.2.1]heptan-2-yl)sulfonyl)carbamate (621 mg) was dissolved in DCM (4 mL), added with TFA (2 mL) to react at room temperature for 30 min. The reaction was monitored by TLC until it was complete. The reaction solution was concentrated under reduced pressure to give 5-((4-(4-(3-bromo-4-fluorophenyl)-5-oxo-4,5-dihydro-1,2,4-oxadiazol-3-yl)-1,2,5-oxadiazol-3-yl)amino)-2-azabicyclo[2.2.1]heptane-2-sulfonamide (600 mg), which was directly used in the next step.

Step 5 Synthesis of N-(3-bromo-4-fluorophenyl)-N'-hydroxy-4-((2-(sulfamoyl)-2-azabicyclo[2.2.1]heptan-5-yl)amino)-1,2,5-oxadiazol-3-formamidine Step 1: Synthesis of 4-(3-bromo-4-fluorophenyl)-3-(4-((2-(methylsulfonyl)-2-azabicyclo[2.2.1]heptan-5-yl)amino)-1,2,5-oxadiazolpyridin-3-yl)-1,2,4-oxadiazol-5(4H)-one

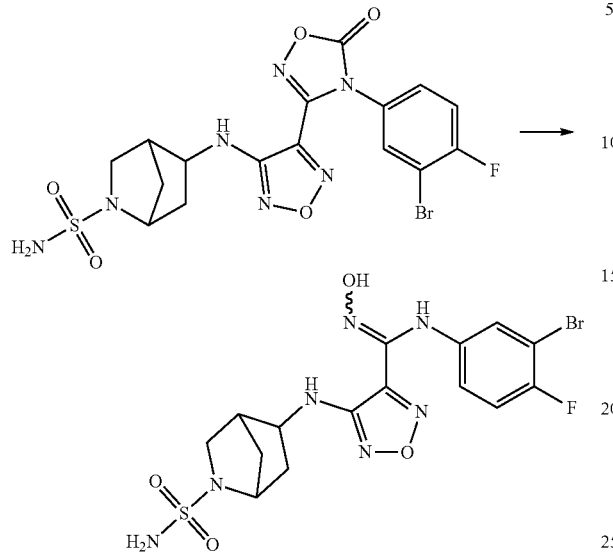

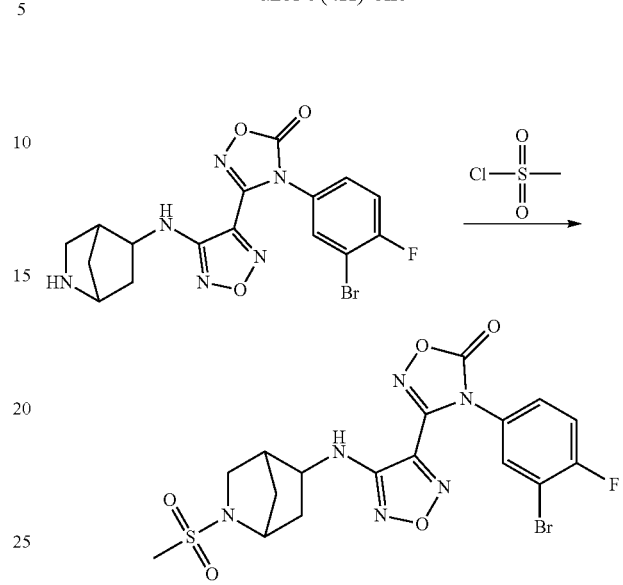

5-((4-(4-(3-bromo-4-fluorophenyl)-5-oxo-4,5-dihydro-1,2,4-oxadiazol-3-yl)-1,2,5-oxadiazol-3-yl)amino)-2-azabicyclo[2.2.1]heptan-2-sulfonamide (400 mg, crude) was dissolved in THF (4 mL), added with 2N sodium hydroxide aqueous solution (4 mL), and reacted with stirring for 30 min at room temperature. The reaction was monitored by TLC until it was complete. The reaction mixture was neutralized with saturated ammonium chloride aqueous solution, added with EA (20 mL×3) for extraction, and the resulting organic phase was separated and combined. The resulting mixture was dried over anhydrous sodium sulfate, filtered, the filtrate was concentrated to obtain a crude product, which was subjected to silica gel column chromatography (eluent: DCM:MeOH=150:1) to give N-(3-bromo-4-fluorophenyl)-N'-hydroxy-4-((2-(sulfamoyl)-2-azabicyclo[2.2.1]heptan-5-yl)amino)-1,2,5-oxadiazol-3-formamidine (49 mg, yield for three steps: 15%).

$^1$HNMR (400 MHz, DMSO-d$_6$) δ (ppm): 11.59 (s, 1H), 8.88 (s, 1H), 7.16-7.21 (m, 2H), 6.85 (s, 1H), 6.75-6.85 (d, 2H), 6.35-6.36 (d, 1H), 3.94 (s, 1H), 3.89 (s, 1H), 3.13-3.16 (d, 2H), 2.88 (s, 1H), 2.20-2.25 (t, 1H), 1.82-1.84 (d, 1H), 1.53-1.55 (d, 1H), 1.40-1.43 (d, 1H).

Molecular Formula: $C_{15}H_{17}BrFN_7O_4S$ Molecular weight: 489.02, LC-MS (Neg, m/z)=488.0 [M−H$^+$].

3-(4-((2-azabicyclo[2.2.1]heptan-5-yl)amino)-1,2,5-oxadiazol-3-yl)-4-(3-bromo-4-fluorophenyl)-1,2,4-oxadiazol-5(4H)-one (obtained in step 2 for preparing compound 18) (290 mg, 0.663 mmol, 1.0 eq) was dissolved in dichloromethane (2 mL), TEA (268 mg, 2.653 mmol, 4 eq) and methanesulfonyl chloride (75.9 mg, 0.663 mmol, 1.0 eq) were added. The resulting mixture was added with water and stirred, and extracted with DCM (20 mL×3). The organic phase was separated and combined. The resulting mixture was dried over anhydrous sodium sulfate and filtered, the filtrate was concentrated to obtain a crude product, which was subjected to thin-layer chromatography (DCM:MeOH=15:1) to give 4-(3-bromo-4-fluorophenyl)-3-(4-((2-(methylsulfonyl)-2-azabicyclo[2.2.1]heptan-5-yl)amino)-1,2,5-oxadiazolpyridin-3-yl)-1,2,4-oxadiazol-5 (4H)-one (267 mg, yield: 78.1%).

Example 15: Synthesis of N-(3-bromo-4-fluorophenyl)-N'-hydroxy-4-((2-(methylsulfonyl)-2-azabicyclo[2.2.1]heptan-5-yl)amino)-1,2,5-oxadiazol-3-formamidine (Compound 19)

Step 2: Synthesis of N-(3-bromo-4-fluorophenyl)-N'-hydroxy-4-((2-(methylsulfonyl)-2-azabicyclo[2.2.1]heptan-5-yl)amino)-1,2,5-oxadiazol-3-formamidine

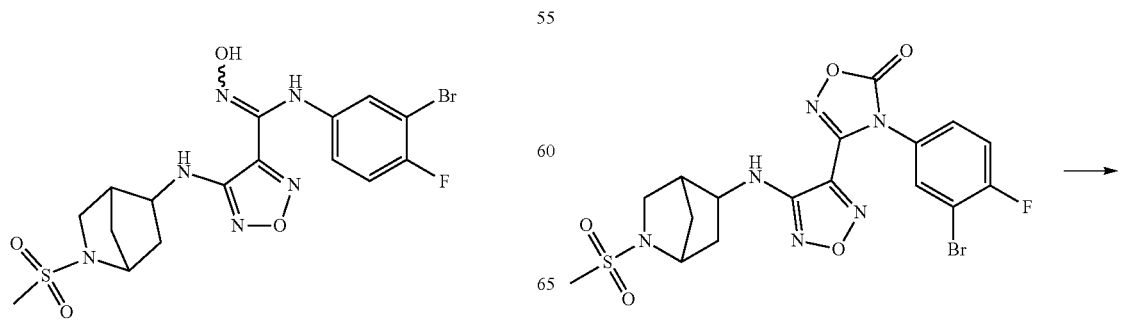

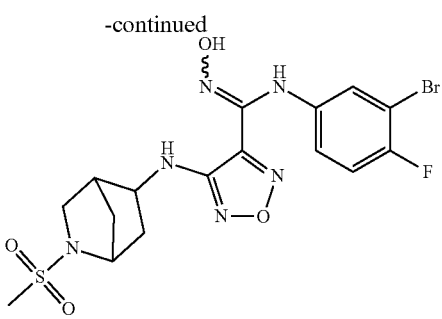

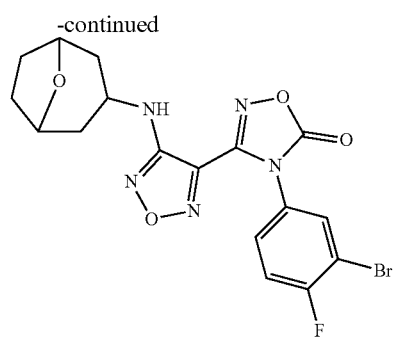

4-(3-bromo-4-fluorophenyl)-3-(4-((2-(methylsulfonyl)-2-azabicyclo[2.2.1]heptan-5-yl)amino)-1,2,5-oxadiazolpyridin-3-yl)-1,2,4-oxadiazol-5 (4H)-one (257 mg) was dissolved in THF (2 mL), added with 2N sodium hydroxide aqueous solution (2 mL), and reacted with stirring for 30 min at room temperature. The reaction was monitored by TLC until it was complete. The reaction mixture was neutralized with saturated ammonium chloride aqueous solution, added with DCM (20 mL×3) for extraction, and the resulting organic phase was separated and combined. The resulting mixture was dried over anhydrous sodium sulfate, filtered, the filtrate was concentrated to obtain a crude product, which was subjected to silica gel preparation column chromatography (eluent: DCM:MeOH=20:1) to give N-(3-bromo-4-fluorophenyl)-N'-hydroxy-4-((2-(methylsulfonyl)-2-azabicyclo[2.2.1]heptan-5-yl)amino)-1,2,5-oxadiazol-3-formamidine (110 mg, yield: 45%).

$^1$HNMR (400 MHz, DMSO-$d_6$) δ (ppm): 11.57 (s, 1H), 8.89 (s, 1H), 7.14-7.21 (m, 2H), 6.82-6.89 (m, 1H), 6.42-6.43 (d, 1H), 4.04 (s, 1H), 3.87-3.91 (m, 1H), 3.15-3.23 (m, 2H), 2.95 (s, 1H), 2.91 (s, 3H), 2.23-2.30 (t, 1H), 1.62-1.74 (t, 2H), 1.39-1.43 (d, 1H).

Molecular Formula: $C_{16}H_{18}BrFN_6O_4S$, Molecular weight: 488.03 LC-MS (Neg, m/z)=487.0 [M–H$^+$].

Example 16: Synthesis of 4-((8-oxabicyclo[3.2.1]octan-3-yl)amino)-N-(3-bromo-4-fluorophenyl)-N'-hydroxy-1,2,5-oxadiazol-3-formamidine (Compound 22)

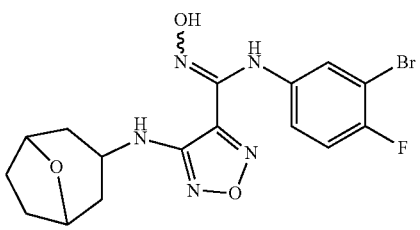 [SMILES: ON=C(Nc1ccc(F)c(Br)c1)c1nonc1NC1CC2CCC(C1)O2]

Step 1: Synthesis of 3-(4-((8-oxabicyclo[3.2.1]octan-3-yl)amino)-1,2,5-oxadiazol-3-yl)-4-(3-bromo-4-fluorophenyl)-1,2,4-oxadiazol-5(4H)-one

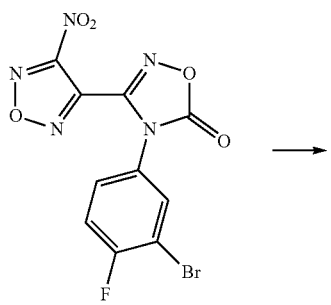

4-(3-bromo-4-fluorophenyl)-3-(4-nitro-1,2,5-oxadiazol-3-yl)-1,2,4-oxadiazol-5(4H)-one (200 mg, 0.538 mmol, 1.0 eq) was dissolved in THF (15 mL), added with 8-oxabicyclo[3.2.1]octan-3-amine hydrochloride (175.9 mg, 1.075 mmol, 2.0 eq) and triethylamine (293.7 mg, 2.903 mmol, 5.4 eq), heated to 70° C. and reacted for 2 hours. The reaction was monitored by TLC until it was complete. The mixture was adjusted to a pH of 2 with 1 mol/L HCl, added with water (10 mL) and EA (20 mL) with stirring. The organic phase was separated, dried over anhydrous sodium sulfate and concentrated to obtain a crude product, which was subjected to silica gel column chromatography (PE:EA=5:1) to give (8-oxabicyclo[3.2.1]octan-3-yl)amino)-1,2,5-oxadiazol-3-yl)-4-(3-bromo-4-fluorophenyl)-1,2,4-oxadiazol-5(4H)-one (120 mg, yield: 49%).

Step 2: Synthesis of 4-((8-oxaspiro[3.2.1]octan-3-yl)amino)-N-(3-bromo-4-fluorophenyl)-N'-hydroxy-1,2,5-oxadiazol-3-formamidine

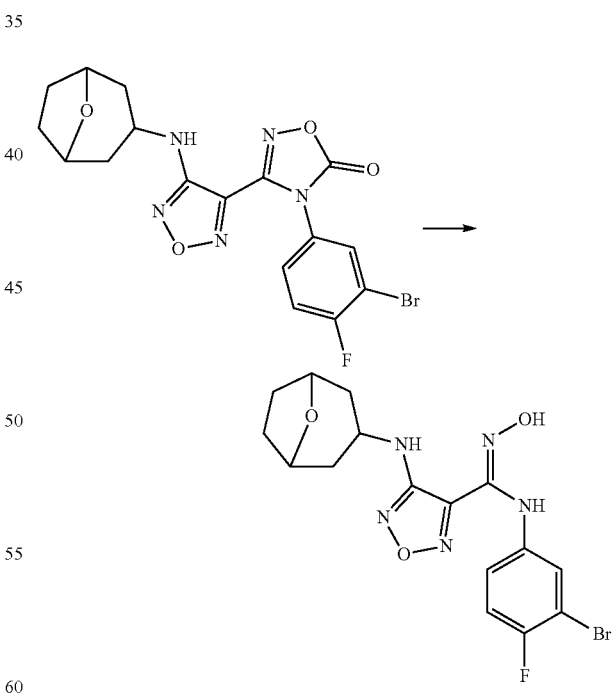

3-(4-((8-oxabicyclo[3.2.1]octan-3-yl)amino)-1,2,5-oxadiazol-3-yl)-4-(3-bromo-4-fluorophenyl)-1,2,4-oxadiazol-5(4H)-one (120 mg, 0.265 mmol, 1.0 eq) was dissolved in THF (1 mL) and 2 mol/L NaOH solution was added. After stirring for 2 h, TLC showed that the reaction was complete. The reaction mixture was added with saturated NH$_4$Cl solution (4 mL), extracted with DCM (20 mL). TLC showed that no product was presented in aqueous phase. The organic phase was combined, dried, concentrated and purified with thin-layer chromatography (DCM:MeOH=20:1) to give 4-((8-oxabicyclo[3.2.1]octan-3-yl)amino)-N-(3-bromo-4-fluorophenyl)-N'-hydroxy-1,2,5-oxadiazol-3-formamidine (80 mg, yield: 71%).

$^1$HNMR (400 MHz, DMSO-$d_6$) δ (ppm): 11.56 (s, 1H), 11.46 (s, 1H), 8.87 (s, 2H), 7.14-7.19 (m, 3H), 6.80 (m, 2H), 6.45 (m, 1H), 6.00 (m, 1H), 4.30-4.35 (m, 3H), 3.70 (m, 1H), 1.75-2.10 (m, 12H) 1.48-1.54 (m, 2H).

Molecular Formula: $C_{16}H_{17}BrFN_5O_3$ Molecular weight: 426.25 LC-MS (Neg, m/z)=426.0 [M–H$^+$].

Example 17: Synthesis of N-(3-bromo-4-fluorophenyl)-4-((1,1-dioxothietan-3-yl)amino)-N'-hydroxy-1,2,5-oxadiazol-3-formamidine (Compound 26)

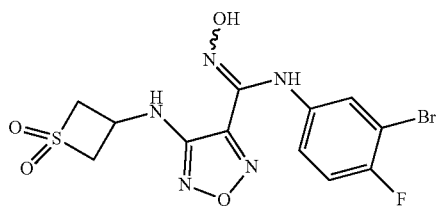 [SMILES: O=S1(=O)CC(Nc2nonc2C(=NO)Nc2ccc(F)c(Br)c2)C1]

Compound 26 was prepared by the preparation method of Example 2.

$^1$HNMR (400 MHz, CDCl$_3$) δ (ppm): 7.56-7.54 (d, 1H), 7.07-7.02 (t, 1H), 7.00-6.91 (m, 1H), 6.47-6.42 (t, 1H), 4.65-4.59 (m, 2H), 4.55-4.50 (m, 1H), 4.17-4.13 (m, 2H).

Molecular Formula: $C_{12}H_{11}BrFN_5O_4S$ Molecular weight: 420.21 LC-MS (Pos, LC-MS (Pos, m/z)=420.0 [M+H$^+$].

BIO-EXPERIMENTAL EXAMPLES

Experimental Example 1

Hela Cell Evaluation Method

Test Sample: Compounds Prepared in the Corresponding Examples of the Present Invention I. Materials and Instruments for the Experiment Helacell strain (Purchased from ATCC, Cat. No. CCL-2, 4965442)

Recombinant Human IFN-γ (rhIFN-γ, Purchased from Peprotech, Cat. No. 300-02)

MEM cell culture medium (Purchased from Invitrogen, Cat. No. 11095098)

Fetal calf serum (Purchased from Invitrogen, Cat. No. 10099-141, Lot. No. 8153379)

6.1 N trichloroacetic acid (Purchased from Sigma, Cat. No. T0699)

II. Test Procedures

Cell plating: Hela cell suspension was prepared from fresh MEM cell culture medium, added to a 96-well cell culture plate at 5000 cells/well, and cultured at 5% carbon dioxide at 37° C. overnight.

Preparation of compound: The compound was formulated into 2 mM in DMSO, and the compound was diluted 5-fold in DMSO to obtain a compound dilution mother solution (200×) of 6 to 9 concentration gradients, and a 10× dilution solution was prepared in proportion with cell culture medium or liquid.

Dosing incubation: After the cells were plated overnight, 10 μL of the corresponding compound dilution mother solution (10×) and 10 μL of 500 ng/mL rhIFN-γ were added to each well, and the final volume of each well was 100 μL. The negative control wells contained 100 μL of 0.5% DMSO cell culture medium and Hela cells. 50 ng/mL of rhIFN-γ were filled into negative control wells, which are used as positive control. Background control wells contained 100 μL of cell culture medium. Incubation was performed for 48 hours in a 37° C. incubator and cell morphology was observed under an inverted microscope.

Detection: 80 μL of the supernatant was added to a Corning 3894 plate, and 10 μL of 6.1 N trichloroacetic acid was added to each well. The plate was shaken for 2 minutes, placed in a 50° C. incubator to react for 30 minutes, centrifuged at 2500 rpm for 10 minutes. 70 μL of the supernatant was transferred to a Corning 3635 UV plate, added with 70 μL of the reaction solution and the mixture was shaken for 2 minutes to make the reaction mixture uniform. The OD value at 480 nm was measured using EnSpire (PE).

III. Test Results

TABLE 1

| Cytological test for the compounds of the invention | |
|---|---|
| Test sample | Hela (nM) |
| Compound 1 | 109 |
| Compound 2 | 39.73 |
| Compound 3 | 70.97 |
| Compound 4 | 78.78 |
| Compound 16 | 78.27 |
| Compound 12 | 104.63 |
| Compound 13 | 68.63 |
| Compound 15 | 51.61 |
| Compound 15-P1 | 19.4 |
| Compound 15-P2 | 119 |
| Compound 26 | 76 |

It can be seen that the compounds of the invention have excellent Hela cell activity.

Experimental Example 2

IDO1 Enzymology Evaluation Method

Test Sample: Compounds Prepared in the Corresponding Examples of the Present Invention I. Materials and Instruments for the Experiment IDO-1 (provided by CP, lot number: 20160706)

Catalase (Purchased From Sigma, Cat. No. C9322-5G)

L-tryptophan (Purchased From Sigma, Cat. No. 93659-10G)

Ascorbate (Purchased From Sigma, Cat. No. 11140-250G)

Methylene blue (Purchased From Sigma, Cat. No. M9140-100G)

DMSO (Purchased From Sigma, Cat. No. D2650)

96-well plate (Purchased From Sigma, Cat. No. 3635)

II. Test Procedures

Preparation of compound: The compound was formulated into 1 mM compound mother liquor in DMSO, and the compound was diluted 3-fold in DMSO to obtain a compound concentration dilution mother solution (100×) of 9 concentration gradients.

Dosing inhibition: 2 μL of 100× compound dilution mother solution was added to a 96-well plate, added with 100 μL of enzyme solution (IDO-1), and incubated for 10 min at room temperature. 100% DMSO was used as a negative control and NLG-919 was used as a positive control. Incubation was performed with 100 μL of substrate mixture (L-tryptophan, ascorbate, methylene blue, and catalase).

Detection: Dynamic OD data at 321 nm was detected using Spectramax.

Calculation: The inhibition rate was calculated according to the following formula.

The curve slope was fitted using the Spectramax program, and IC50 was fitted using GraphPad Prism 5.0.

$$\text{Inhibition rate}(\%) = \frac{OD\text{negative control} - OD\text{compound}}{OD\text{negative control} - OD\text{ Background}} \times 100\%$$

III. Test Results

TABLE 2

Enzymology test for the compounds of the invention

| Test sample | IDO1(nM) |
|---|---|
| Compound 13 | 220 |
| Compound 15 | 220 |
| Compound 15-P1 | 200 |
| Compound 15-P2 | 240 |
| Compound 16 | 170 |

It can be seen that the compounds of the invention have excellent IDO enzymology activity.

Example 3: Rat PK Evaluation of the Compounds

Solutol: Polyethylene glycol 15-hydroxylstearate
DMA: N,N-Dimethylacetamide
Test Sample: Compounds Prepared in the Corresponding Examples of the Present Invention Animal administration and sample collection: intragastric administration: Compounds 2 and 13 were dissolved in 10% DMA+10% (30% Solutol)+80% physiological saline to prepare a solution. Compound 15 was dissolved in 10% DMA+10% PEG400+80% physiological saline to prepare a solution. The SD rats were intragastrically administered at a dose of 5.0 mg/kg. The time of blood collection was: 15 min, 30 min, 1 h, 2 h, 4 h, 6 h, 8 h and 24 h.

Intravenous administration: Compounds 2 and 13 were dissolved in 10% DMA+10% (30% Solutol)+80% physiological saline to prepare a solution. Compound 15 was dissolved in 10% DMA+10% PEG400+80% physiological saline to prepare a solution. The SD rats were intravenous administered at a dose of 1 mg/kg. The time of blood collection was: 5 min, 15 min, 30 min, 1 h, 2 h, 4 h, 6 h, 8 h and 24 h.

The animals were fixed, the tail was heated in a water bath 10 min before each time point, and about 100 μL of blood was collected through the tail vein, and the blood was then placed in an anti-coagulation tube containing EDTA-K2. Blood samples were centrifuged at 8000 rpm for 6 min at 4° C. to obtain plasma samples, which must be prepared within 30 min of blood collection. The plasma samples were stored at −80° C. in a freezer before test.

Sample Analysis Method:

Take the sample to be tested from the refrigerator (−80° C.), melted at room temperature and vortexed for 5 min. 20 μL of plasma sample was accurately pipetted into a 1.5 mL centrifuge tube; added with 200 μL of internal standard working solution at a concentration of 50 ng/mL and mixed well. The mixture was vortexed for 5 min (12000 rpm) and centrifuge for 5 min (12000 rpm). 50 μL of supernatant was accurately pipetted into 96-well plates pre-filled with 150 μL/well of water; vortexed for 5 min to mix well. The inject volume was 20 μL and LC-MS/MS was performed.

Data Processing Method:

The concentration of the test sample was output by using Analyst 1.6.3 from AB. The mean, standard deviation, coefficient of variation and other parameters were calculated by Microsoft Excel (direct output from Analyst 1.6.3 is not calculated). PK parameters are calculated by using Pharsight Phoenix 6.1 software NCA (Tmax is the median).

Result:

TABLE 3

PK test in rats of the compound of the present invention

| Test sample | $t_{z1/2}$ iv/ $t_{Z1/2}$ PO (h) | $V_{z\_obs}$ iv (L/kg) | $Cl_{\_obs}$ iv (L/h/kg) | $T_{max}$ PO (h) | $AUC_{inf}$ iv/$AUC_{inf}$ PO (h*ng/mL) | F % |
|---|---|---|---|---|---|---|
| Compound 2 | 1.82/3.81 | 5.02 | 1.97 | 0.25 | 521/1621 | 62.2 |
| Compound 13 | 2.00/1.67 | 9.00 | 3.20 | 0.25 | 336/620 | 36.9 |
| Compound 15 | 1.03/3.40 | 4.03 | 2.73 | 1.00 | 367/516 | 28.1 |

(IV: 1 mg/kg, PO: 5 mg/kg, n = 3)

As can be seen from the above results, the compounds of the present invention have excellent pharmacokinetic properties.

The invention claimed is:

1. A compound of formula II, or a pharmaceutically acceptable salt or a stereoisomer thereof:

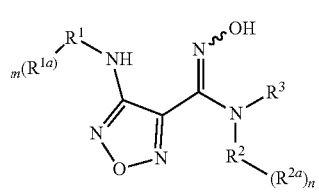

II wherein,

∿∿ represents a cis-isomer, a trans-isomer or a mixture of a cis-isomer and a trans-isomer;

67

R¹ is selected from the group consisting of

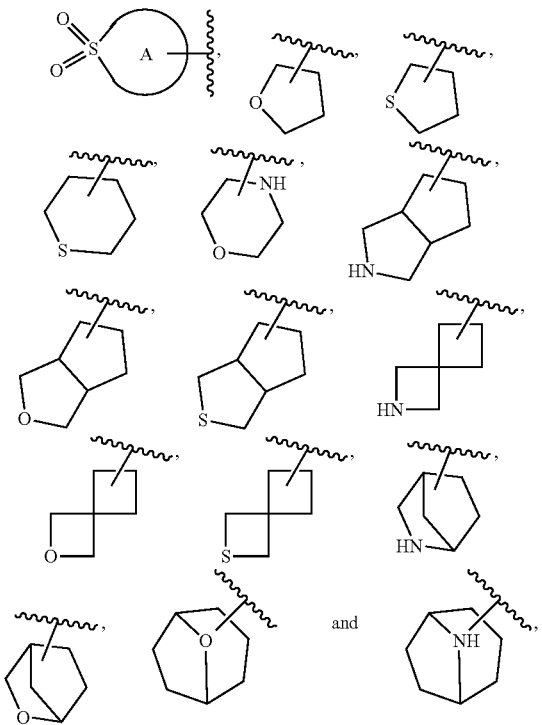

wherein ring A is 4-12 membered mono-, ortho-, spiro-, or bridged heterocyclyl, which is optionally substituted with $R^{1a}$, wherein $R^{1a}$ is selected from the group consisting of hydrogen, halogen, $C_{1-6}$ alkyl, $C_{2-6}$ alkenyl, $C_{2-6}$ alkynyl, halogenated $C_{1-6}$ alkyl, —CN, —NO$_2$, —OR$^b$, —C(O)R$^c$, —C(O)OR$^b$, —OC(O)R$^c$, —C(O)NR$^e$R$^f$, —OC(O)NR$^e$R$^f$, —NR$^e$R$^f$, —NR$^d$C(O)R$^c$, —NR$^d$C(O)NR$^e$R$^f$, —NR$^d$C(O)OR$^b$, —SR$^b$, —S(O)R$^c$, —S(O)NR$^e$R$^f$, —S(O)$_2$R$^c$, —S(O)$_2$NR$^e$R$^f$, 3-8 membered cycloalkyl, 3-8 membered heterocyclyl, 5-8 membered heteroaryl and 6-14 membered aryl;

R² is selected from the group consisting of 6-14 membered aryl and 5-12 membered heteroaryl, which is optionally substituted with $R^{2a}$, wherein $R^{2a}$ is selected from the group consisting of hydrogen, halogen, $C_{1-6}$ alkyl, $C_{2-6}$ alkenyl, $C_{2-6}$ alkynyl, halogenated $C_{1-6}$ alkyl, —CN, —NO$_2$, —OR$^b$, —C(O)R$^c$, —C(O)OR$^b$, —OC(O)R$^c$, —C(O)NR$^e$R$^f$, —OC(O)NR$^e$R$^f$, —NR$^e$R$^f$, —NR$^d$C(O)R$^c$, —NR$^d$C(O)NR$^e$R$^f$, —NR$^d$C(O)OR$^b$, —SR$^b$, —S(O)R$^c$, —S(O)NR$^e$R$^f$, —S(O)$_2$R$^c$, —S(O)$_2$NR$^e$R$^f$, 3-8 membered cycloalkyl, 3-8 membered heterocyclyl, 5-8 membered heteroaryl and 6-14 membered aryl;

R³ is hydrogen or $C_{1-6}$ alkyl;

R$^b$ is selected from the group consisting of hydrogen, $C_{1-6}$ alkyl, halogenated $C_{1-6}$ alkyl and $C_{1-6}$ alkoxy $C_{1-6}$ alkyl;

R$^c$ is selected from the group consisting of hydrogen, $C_{1-6}$ alkyl, halogenated $C_{1-6}$ alkyl and $C_{1-6}$ alkoxy;

R$^d$, R$^e$ and R$^f$ are independently of each other selected from the group consisting of hydrogen, $C_{1-6}$ alkyl and halogenated $C_{1-6}$ alkyl;

m is 0, 1, 2 or 3; and n is 0, 1, 2 or 3.

2. The compound or the pharmaceutically acceptable salt or the stereoisomer thereof according to claim 1, wherein,

68

R¹ is

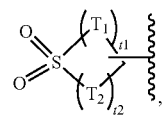

wherein $T_1$ and $T_2$ are independently of each other selected from the group consisting of CR$^4$R$^{4'}$, NR$^4$ and O, $t_1$ and $t_2$ are independently of each other 0, 1, 2 or 3, and $t_1$ and $t_2$ are not equal to 0 at the same time, and the sum of $t_1$ and $t_2$ is more than or equal to 2; R¹ is optionally substituted with $R^{1a}$, wherein $R^{1a}$ is selected from the group consisting of hydrogen, halogen, $C_{1-6}$ alkyl, $C_{2-6}$ alkenyl, $C_{2-6}$ alkynyl, halogenated $C_{1-6}$ alkyl, —CN, —NO$_2$, —OR$^b$, —C(O)R$^c$, —C(O)OR$^b$, —OC(O)R$^c$, —C(O)NR$^e$R$^f$, —OC(O)NR$^e$R$^f$, —NR$^e$R$^f$, —NR$^d$C(O)R$^c$, —NR$^d$C(O)NR$^e$R$^f$, —NR$^d$C(O)OR$^b$, —SR$^b$, —S(O)R$^c$, —S(O)NR$^e$R$^f$, —S(O)$_2$R$^c$, —S(O)$_2$NR$^e$R$^f$, 5-7 membered cycloalkyl, 5-7 membered heterocyclyl, 5-7 membered heteroaryl and phenyl; and R$^4$ and R$^{4'}$ are hydrogen; and R² is phenyl, optionally substituted with $R^{2a}$, wherein $R^{2a}$ is selected from the group consisting of hydrogen, halogen and $C_{1-6}$ alkyl.

3. The compound or the pharmaceutically acceptable salt or the stereoisomer thereof according to claim 2, wherein, R¹ is

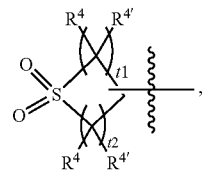

wherein $t_1$ and $t_2$ are independently of each other 0, 1, 2 or 3, and $t_1$ and $t_2$ are not equal to 0 at the same time, and the sum of $t_1$ and $t_2$ is more than or equal to 2; R¹ is optionally substituted with $R^{1a}$, wherein $R^{1a}$ is selected from the group consisting of hydrogen, halogen, $C_{1-6}$ alkyl, $C_{2-6}$ alkenyl, $C_{2-6}$ alkynyl, halogenated $C_{1-6}$ alkyl, —CN, —NO$_2$, —OR$^b$, —C(O)R$^c$, —C(O)OR$^b$, —OC(O)R$^c$, —C(O)NR$^e$R$^f$, —OC(O)NR$^e$R$^f$, —NR$^e$R$^f$, —NR$^d$C(O)R$^c$, —NR$^d$C(O)NR$^e$R$^f$, —NR$^d$C(O)OR$^b$, —SR$^b$, —S(O)R$^c$, —S(O)NR$^e$R$^f$, —S(O)$_2$R$^c$ and —S(O)$_2$NR$^e$R$^f$; and R$^4$ and R$^{4'}$ are hydrogen.

4. The compound or the pharmaceutically acceptable salt or the stereoisomer thereof according to claim 1, wherein, R¹ is

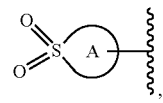

wherein ring A is selected from the group consisting of 6-12 membered ortho-heterocyclyl, 6-12 membered bridged heterocyclyl and 6-12 membered spiro-heterocyclyl, which is optionally substituted with $R^{1a}$, wherein $R^{1a}$ is selected from the group consisting of hydrogen, halogen, $C_{1-6}$ alkyl, $C_{2-6}$ alkenyl, $C_{2-6}$ alkynyl, halogenated $C_{1-6}$ alkyl, —CN, —NO$_2$, —OR$^b$, —C(O)R$^c$, —C(O)OR$^b$, —OC(O)R$^c$, —C(O)NR$^e$R$^f$, —OC(O)NR$^e$R$^f$, —NR$^e$R$^f$, —NR$^d$C(O)R$^c$, —NR$^d$C(O)

NR$^e$R$^f$, —NR$^d$C(O)OR$^b$, —SR$^b$, —S(O)R$^c$, —S(O)NR$^e$R$^f$, —S(O)$_2$R$^c$, —S(O)$_2$NR$^e$R$^f$, 5-7 membered cycloalkyl, 5-7 membered heterocyclyl, 5-7 membered heteroaryl and phenyl; and R$^2$ is phenyl, optionally substituted with R$^{2a}$, wherein R$^{2a}$ is selected from the group consisting of hydrogen, halogen and C$_{1-6}$ alkyl.

5. The compound or the pharmaceutically acceptable salt or the stereoisomer thereof according to claim 4, wherein, R$^1$ is

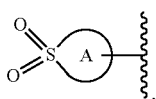

wherein ring A is selected from the group consisting of 6-12 membered saturated ortho-heterocyclyl, 6-12 membered saturated bridged heterocyclyl and 6-12 membered saturated spiro-heterocyclyl, which is optionally substituted with R$^{1a}$, wherein R$^{1a}$ is selected from the group consisting of hydrogen, halogen, C$_{1-6}$ alkyl, C$_{2-6}$ alkenyl, C$_{2-6}$ alkynyl, halogenated C$_{1-6}$ alkyl, —CN, —NO$_2$, —OR$^b$, —C(O)R$^c$, —C(O)OR$^b$, —OC(O)R$^c$, —C(O)NR$^e$R$^f$, —OC(O)NR$^e$R$^f$, —NR$^e$R$^f$, —NR$^d$C(O)R$^c$, —NR$^d$C(O)NR$^e$R$^f$, —NR$^d$C(O)OR$^b$, —SR$^b$, —S(O)R$^c$, —S(O)NR$^e$R$^f$, —S(O)$_2$R$^c$ and —S(O)$_2$NR$^e$R$^f$.

6. The compound or the pharmaceutically acceptable salt or the stereoisomer thereof according to claim 1, wherein R$^2$ is phenyl, optionally substituted with R$^{2a}$, wherein R$^{2a}$ is selected from the group consisting of hydrogen, halogen and C$_{1-4}$ alkyl;

R$^3$ is hydrogen or C$_{1-4}$ alkyl;

R$^b$, R$^c$, R$^d$, R$^e$ and R$^f$ are independently of each other hydrogen or C$_{1-4}$ alkyl; and R$^1$ is selected from the group consisting of

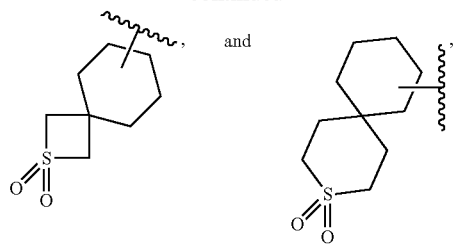

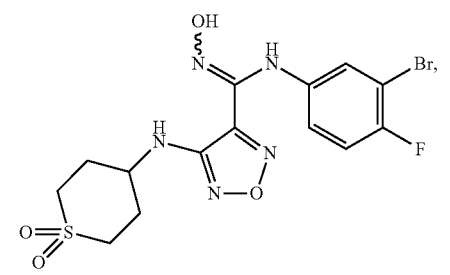

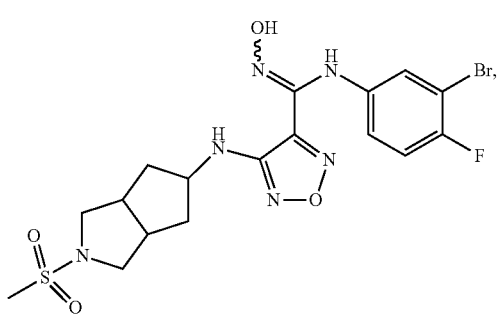

which is optionally substituted with R$^{1a}$, wherein R$^{1a}$ is selected from the group consisting of hydrogen, halogen and C$_{1-4}$ alkyl.

7. The compound or the pharmaceutically acceptable salt or the stereoisomer thereof according to claim 1, wherein the compound is selected from the group consisting of:

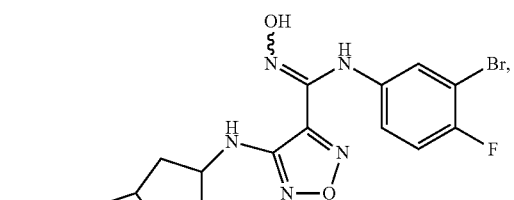

2

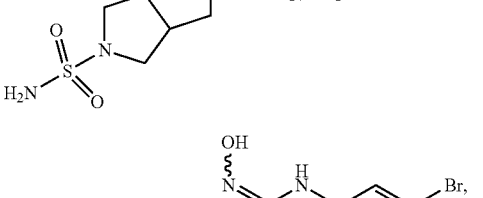

8

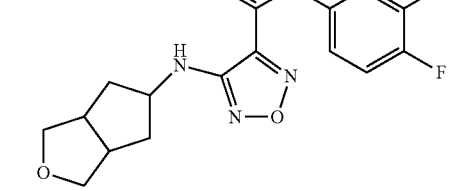

9

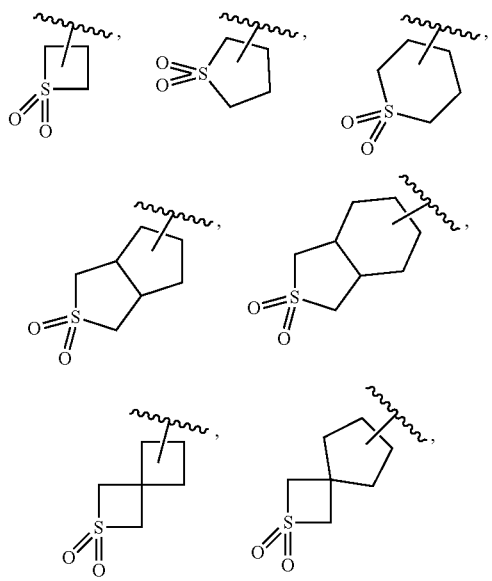

10

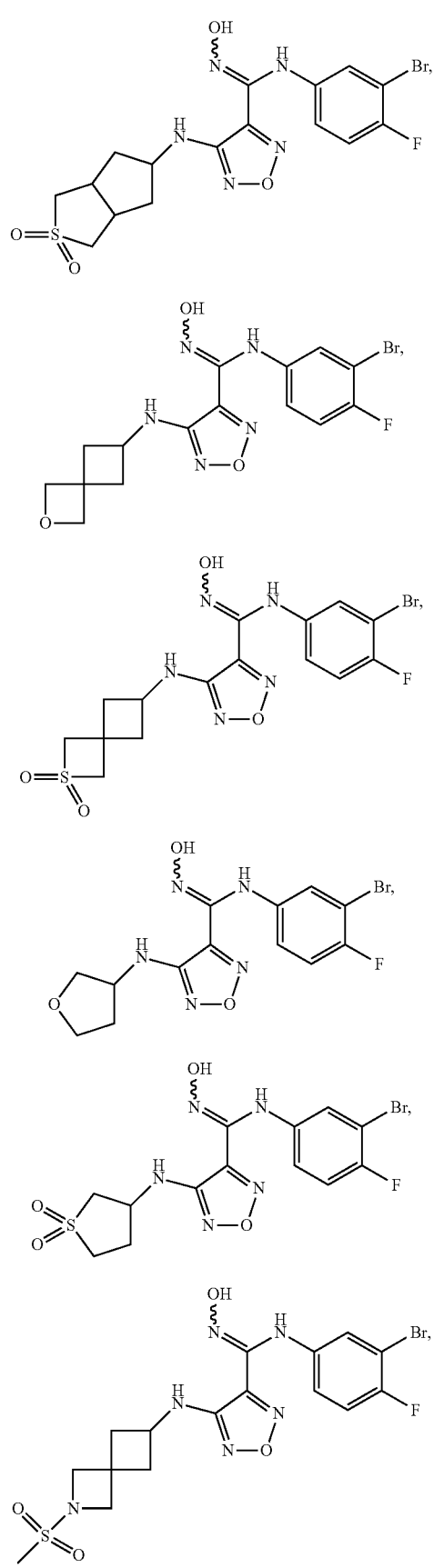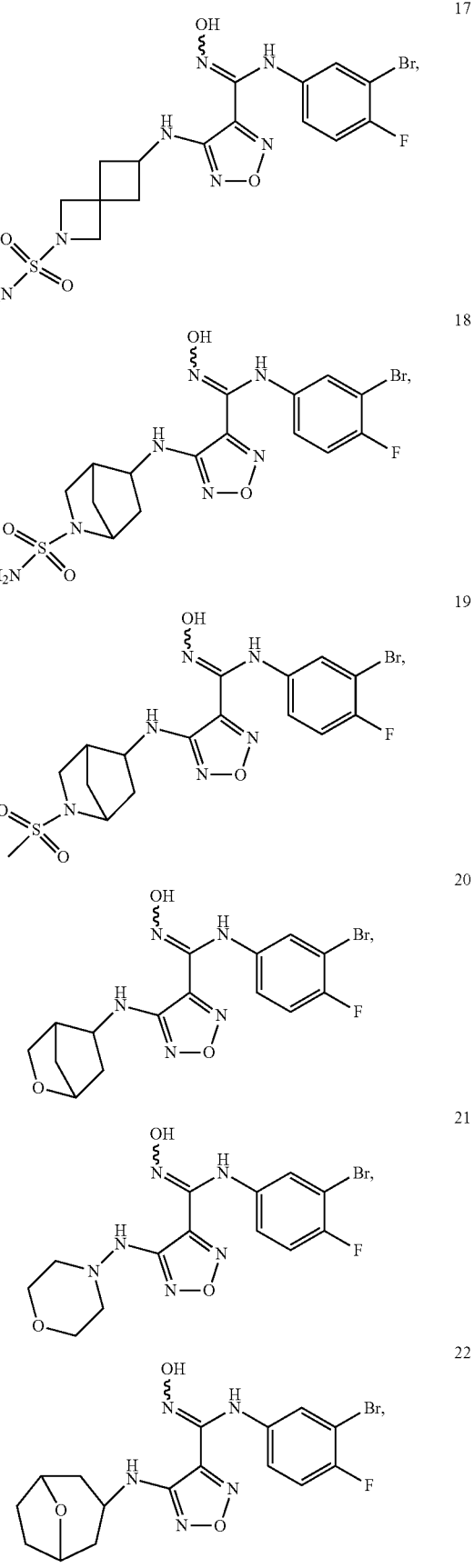

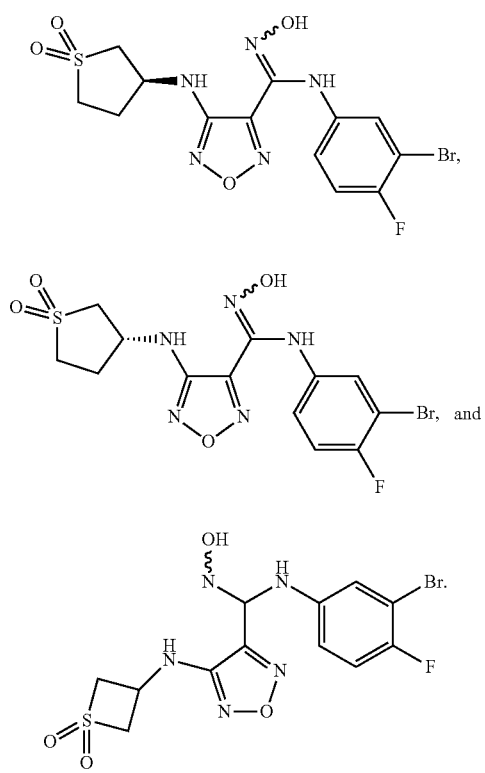

8. A pharmaceutical composition comprising the compound or the pharmaceutically acceptable salt or the stereoisomer thereof according to claim 1, and one or more pharmaceutically acceptable carriers.

9. A method for treating a disease mediated by IDO abnormality, comprising administering a subject in need thereof the compound or the pharmaceutically acceptable salt or the stereoisomer thereof according to claim 1.

10. The method according to claim 9, wherein the disease mediated by IDO abnormality is an infectious disease, a nervous system disease, a cancer or a non-cancerous proliferative disease.

11. The compound or the pharmaceutically acceptable salt or the stereoisomer thereof according to claim 1, wherein $R^1$ is selected from the group consisting of

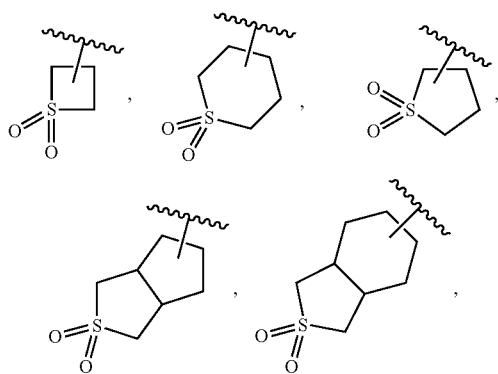

which is optionally substituted with $R^{1a}$, wherein $R^{1a}$ is selected from the group consisting of hydrogen, halogen, $C_{1-4}$ alkyl, halogenated $C_{1-4}$ alkyl, —CN, —NO$_2$, —OR$^b$, —C(O)R$^c$, —C(O)OR$^b$, —OC(O)R$^c$, —C(O)NR$^e$R$^f$, —OC(O)NR$^e$R$^f$, —NR$^e$R$^f$, —NR$^d$C(O)R$^c$, —NR$^d$C(O)NR$^e$R$^f$, —NR$^d$C(O)OR$^b$, —S(O)$_2$R$^c$ and —S(O)$_2$NR$^e$R$^f$.

12. The compound or the pharmaceutically acceptable salt or the stereoisomer thereof according to claim 1, wherein $R^1$ is

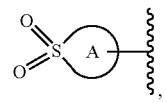

wherein ring A is selected from the group consisting of 4-8 membered mono-heterocyclyl, 6-12 membered ortho-heterocyclyl, 6-12 membered bridged heterocyclyl and 6-12 membered spiro-heterocyclyl; and $R^2$ is phenyl.

13. The compound or the pharmaceutically acceptable salt or the stereoisomer thereof according to claim 3, wherein $R^1$ is

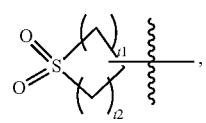

wherein $t_1$ and $t_2$ are independently of each other 0, 1, 2 or 3, and $t_1$ and $t_2$ are not equal to 0 at the same time, and the sum of $t_1$ and $t_2$ is more than or equal to 2; and $R^1$ is optionally substituted with $R^{1a}$, wherein $R^{1a}$ is selected from the group consisting of hydrogen, halogen and $C_{1-6}$ alkyl;

$R^2$ is phenyl, optionally substituted with $R^{2a}$, wherein $R^{2a}$ is selected from the group consisting of hydrogen, halogen and $C_{1-6}$ alkyl; and m is 0, 1 or 2.

14. The compound or the pharmaceutically acceptable salt or the stereoisomer thereof according to claim 6, wherein $R^1$ is selected from the group consisting of

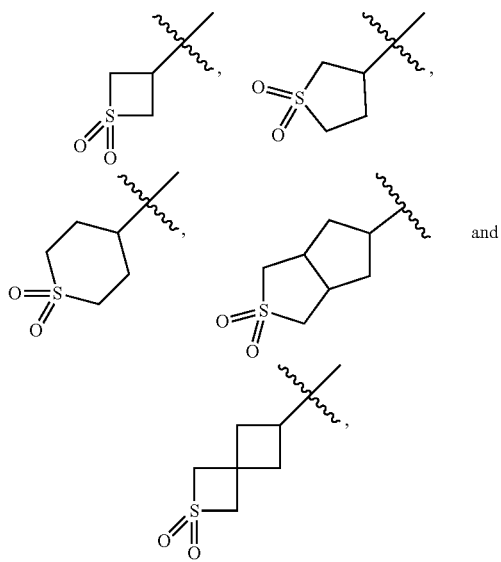

which is optionally substituted with $R^{1a}$, wherein $R^{1a}$ is selected from the group consisting of hydrogen, halogen and $C_{1-4}$ alkyl.

15. The method according to claim 10, wherein the infectious disease is selected from the group consisting of diseases caused by infection of influenza virus, hepatitis C virus, human papillomavirus, cytomegalovirus, E-B virus, poliovirus, varicella zoster virus, Coxsackie virus or human immunodeficiency virus; the nervous system disease is selected from the group consisting of Alzheimer's disease and depression; the cancer is selected from the group consisting of lung cancer, squamous cell carcinoma, bladder cancer, gastric cancer, ovarian cancer, peritoneal cancer, breast cancer, ductal carcinoma of the breast, head and neck cancer, endometrial cancer, uterine body cancer, rectal cancer, liver cancer, kidney cancer, renal pelvic cancer, esophageal cancer, esophageal adenocarcinoma, glioma, prostate cancer, thyroid cancer, female reproductive system cancer, carcinoma in situ, lymphoma, neurofibromatosis, bone cancer, skin cancer, brain cancer, colon cancer, testicular cancer, gastrointestinal stromal tumor, oral cancer, pharyngeal cancer, multiple myeloma, leukemia, non-Hodgkin's lymphoma, large intestine villus adenoma, melanoma, cell tumor, and sarcoma; the non-cancerous proliferative disease is selected from the group consisting of a myeloproliferative disorder and a lymphoproliferative disease.

16. A pharmaceutical composition comprising the compound or the pharmaceutically acceptable salt or the stereoisomer thereof according to claim 7, and one or more pharmaceutically acceptable carriers.

17. A method for treating a disease mediated by IDO abnormality, comprising administering a subject in need thereof the compound or the pharmaceutically acceptable salt or the stereoisomer thereof according to claim 7.

18. The method according to claim 17, wherein the disease mediated by IDO abnormality is an infectious disease, a nervous system disease, a cancer or a non-cancerous proliferative disease.

19. The method according to claim 18, wherein the infectious disease is selected from the group consisting of diseases caused by infection of influenza virus, hepatitis C virus, human papillomavirus, cytomegalovirus, E-B virus, poliovirus, varicella zoster virus, Coxsackie virus or human immunodeficiency virus; the nervous system disease is selected from the group consisting of Alzheimer's disease and depression; the cancer is selected from the group consisting of lung cancer, squamous cell carcinoma, bladder cancer, gastric cancer, ovarian cancer, peritoneal cancer, breast cancer, ductal carcinoma of the breast, head and neck cancer, endometrial cancer, uterine body cancer, rectal cancer, liver cancer, kidney cancer, renal pelvic cancer, esophageal cancer, esophageal adenocarcinoma, glioma, prostate cancer, thyroid cancer, female reproductive system cancer, carcinoma in situ, lymphoma, neurofibromatosis, bone cancer, skin cancer, brain cancer, colon cancer, testicular cancer, gastrointestinal stromal tumor, oral cancer, pharyngeal cancer, multiple myeloma, leukemia, non-Hodgkin's lymphoma, large intestine villus adenoma, melanoma, cell tumor, and sarcoma; the non-cancerous proliferative disease is selected from the group consisting of a myeloproliferative disorder and a lymphoproliferative disease.

20. The method according to claim 19, wherein the disease mediated by IDO abnormality is a cancer, and wherein the cancer is selected from the group consisting of lung cancer, bladder cancer, gastric cancer, ovarian cancer, peritoneal cancer, breast cancer, head and neck cancer, endometrial cancer, rectal cancer, liver cancer, kidney cancer, esophageal cancer, glioma, prostate cancer, female reproductive system cancer, brain cancer, gastrointestinal stromal tumor, pharyngeal cancer, leukemia, melanoma, cell tumor, and sarcoma.

* * * * *